United States Patent
Takeshima

(10) Patent No.: US 9,968,273 B2
(45) Date of Patent: May 15, 2018

(54) ECG WAVEFORM DETECTING APPARATUS AND IMAGING APPARATUS

(71) Applicant: TOSHIBA MEDICAL SYSTEMS CORPORATION, Otawara-Shi, Tochigi-Ken (JP)

(72) Inventor: Hidenori Takeshima, Kanagawa (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 0 days. days.

(21) Appl. No.: 14/978,284

(22) Filed: Dec. 22, 2015

(65) Prior Publication Data
US 2016/0106332 A1 Apr. 21, 2016

Related U.S. Application Data

(63) Continuation of application No. PCT/JP2015/062245, filed on Apr. 22, 2015.

(30) Foreign Application Priority Data

Apr. 25, 2014 (JP) .................................. 2014-091569
May 13, 2014 (JP) .................................. 2014-099914
Jun. 13, 2014 (JP) .................................. 2014-122541

(51) Int. Cl.
*A61B 5/0456* (2006.01)
*A61B 5/04* (2006.01)
(Continued)

(52) U.S. Cl.
CPC ........ *A61B 5/04012* (2013.01); *A61B 5/0428* (2013.01); *A61B 5/0452* (2013.01);
(Continued)

(58) Field of Classification Search
CPC .......................... A61B 5/04525; A61B 5/0456
See application file for complete search history.

(56) References Cited

U.S. PATENT DOCUMENTS 3,543,050 A * 11/1970 Shepard ............... A61B 5/0436
327/28
3,927,663 A * 12/1975 Russell ................ A61B 5/0456
128/901
(Continued)

FOREIGN PATENT DOCUMENTS

JP   H03-000044       1/1991
JP   03026233  A  *  2/1991 ........... A61B 5/0456
(Continued)

OTHER PUBLICATIONS

English Translation of International Preliminary Report on Patentability dated Oct. 25, 2016 for Application No. PCT/JP2015/062245.
(Continued)

*Primary Examiner* — Kennedy Schaetzle
(74) *Attorney, Agent, or Firm* — Nixon & Vanderhye P.C.

(57) ABSTRACT

According to one embodiment, an ECG waveform detecting apparatus includes an input circuit and processing circuitry. The input circuit receives an ECG signal. The processing circuitry performs first detection of a specific waveform included in the ECG signal, performs update processing of a detection parameter for detecting the specific waveform based on a part of the specific waveform or result of the first detection, performs second detection of the specific waveform from the ECG signal by using the detection parameter after the update processing, and generates a synchronization signal based on information on the second detection.

18 Claims, 41 Drawing Sheets

(51) Int. Cl.
*A61B 5/0452* (2006.01)
*A61B 5/0472* (2006.01)
*A61B 5/055* (2006.01)
*A61B 5/0428* (2006.01)

(52) U.S. Cl.
CPC .......... *A61B 5/0456* (2013.01); *A61B 5/0472* (2013.01); *A61B 5/055* (2013.01)

(56) References Cited

U.S. PATENT DOCUMENTS

| | | | |
|---|---|---|---|
| 4,023,564 A * | 5/1977 | Valiquette | A61B 5/04525 600/517 |
| 4,316,249 A * | 2/1982 | Gallant | A61B 5/044 600/515 |
| 7,027,858 B2 | 4/2006 | Cao et al. | |
| 7,113,820 B2 * | 9/2006 | Schlegel | A61B 5/0452 600/509 |
| 7,783,854 B2 | 8/2010 | Gunderson | |
| 7,925,334 B2 | 4/2011 | Farazi | |
| 8,068,901 B2 | 11/2011 | Ghanem et al. | |
| 8,452,387 B2 | 5/2013 | Osorio et al. | |
| 8,571,643 B2 | 10/2013 | Osorio et al. | |
| 8,706,201 B2 | 4/2014 | Beker et al. | |
| 9,002,453 B2 * | 4/2015 | Keel | A61B 5/0422 600/516 |
| 2003/0018248 A1 * | 1/2003 | Kreger | A61B 5/0456 600/413 |
| 2003/0088286 A1 * | 5/2003 | Ostroff | A61N 1/385 607/9 |
| 2003/0120164 A1 * | 6/2003 | Nielsen | A61B 5/02055 600/513 |
| 2003/0161436 A1 * | 8/2003 | Boyd | A61B 6/032 378/8 |
| 2008/0033312 A1 | 2/2008 | Nakai et al. | |
| 2009/0287268 A1 * | 11/2009 | Nabutovsky | A61N 1/3622 607/14 |
| 2012/0184858 A1 | 7/2012 | Harlev et al. | |

FOREIGN PATENT DOCUMENTS

| | | |
|---|---|---|
| JP | H04-322638 | 11/1992 |
| JP | 2004-329669 | 11/2004 |
| JP | 2005-027944 | 2/2005 |
| JP | 2006-075403 | 3/2006 |
| JP | 2006-116207 | 5/2006 |
| JP | 2008-104640 | 5/2008 |
| WO | WO 99/04688 | 2/1999 |

OTHER PUBLICATIONS

International Search Report for PCT/JP2015/050819 dated Apr. 7, 2015, 2 pages.

Ruha et al., "A Real-time Microprocessor QRS Detector System with a 1-ms Timing Accuracy for the Measurement of Ambulatory HRV," *IEEE Transactions on Biomedical Engineering*, 1997; 44: 159-167.

Kohler et al., "The Principles of Software QRS Detection," *IEEE Engineering in Medicine and Biology*, pp. 42-57, Jan./Feb. 2002.

Pan et al., "A Real-time QRS Detection Algorithm," *IEEE Trans. Biomedical Engineering*, vol. 32, No. 3, pp. 230-236, 1985.

Kim et al., "Implementation of Template Matching Based ECG Compression Algorithm for Mobile Application", *2013 International Conference on IT Convergence and Security (ICITCS)*, Dec. 2013.

* cited by examiner

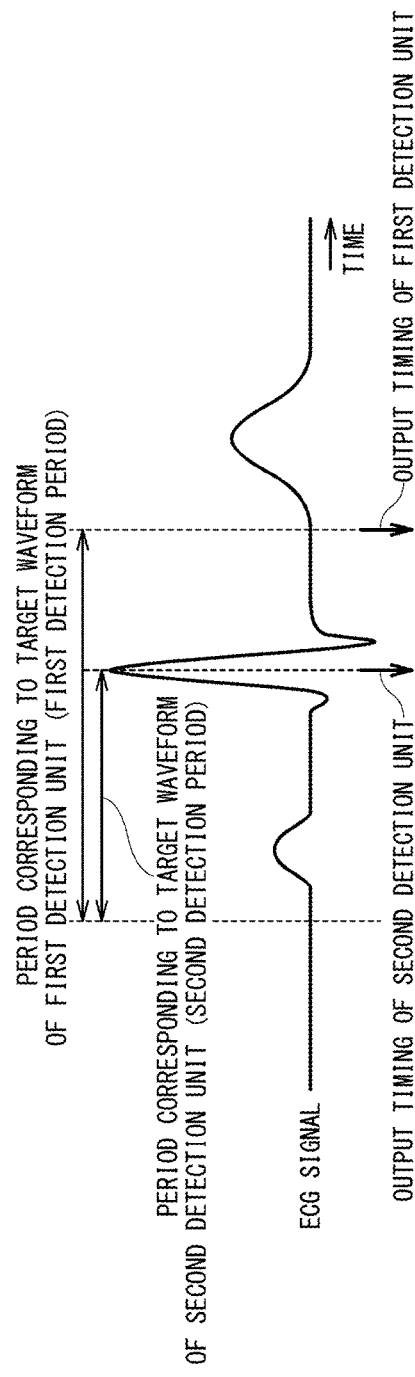
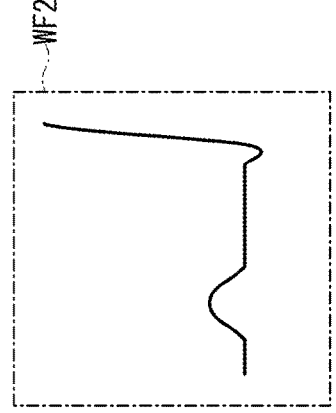
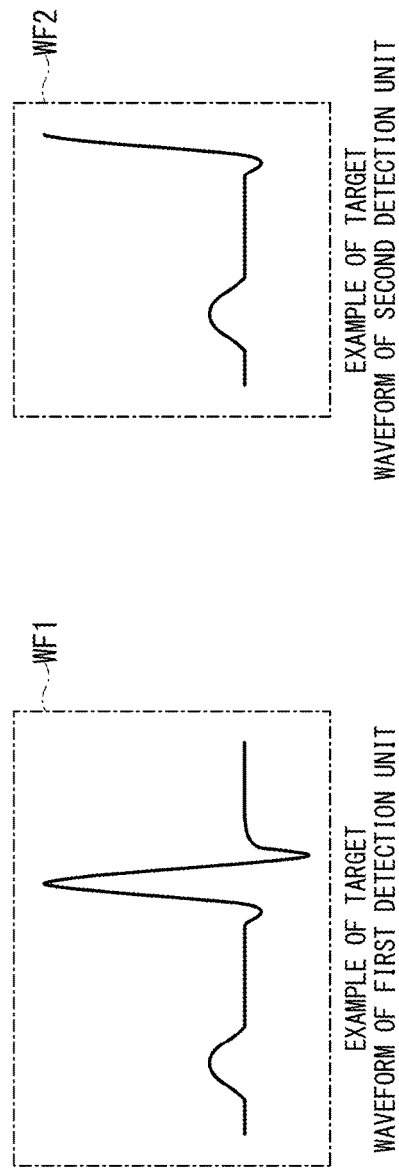
FIG. 4A
FIG. 4B
FIG. 4C

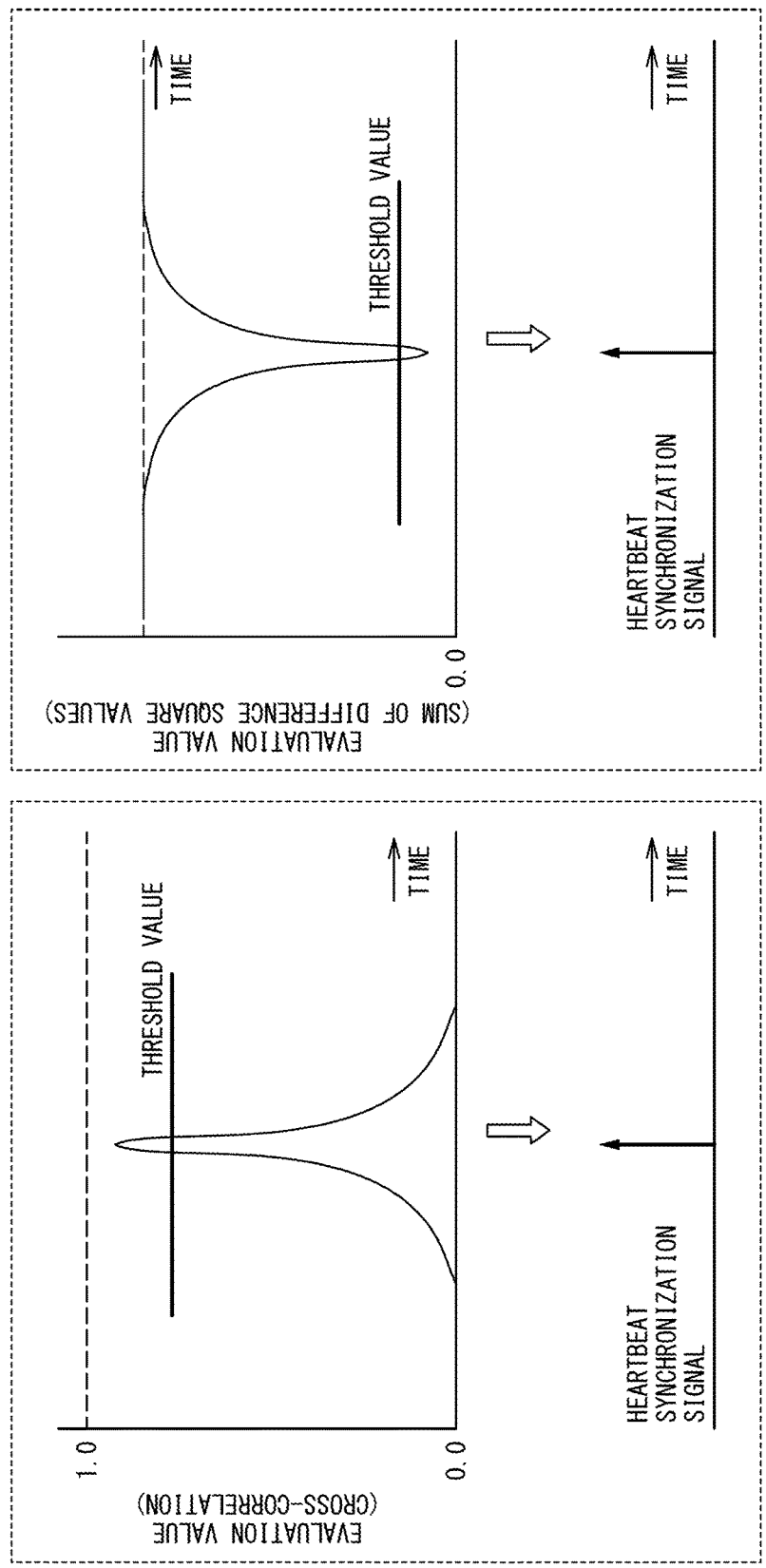

ECG WAVEFORM DETECTING APPARATUS AND IMAGING APPARATUS

CROSS-REFERENCE TO RELATED APPLICATIONS

This application is a Continuation application of No. PCT/JP2015/062245, filed on Apr. 22, 2015, and the PCT application is based upon and claims the benefit of priority from Japanese Patent Applications No. 2014-91569, filed on Apr. 25, 2014, No. 2014-99914, filed on May 13, 2014, and No. 2014-122541, filed on Jun. 13, 2014, the entire contents of each of which are incorporated herein by reference.

FIELD

Embodiments described herein relate generally to an ECG (electrocardiographic) waveform detecting apparatus and an imaging apparatus.

BACKGROUND

An electrocardiograph is a device whose electrodes are set on a biological body to measure an electric potential difference between the electrodes. Information measured by an electrocardiograph is referred to as an electrocardiogram (ECG) and is widely used in the medical field. As information obtained from an electrocardiogram, for example, there are a P-wave, an R-wave, a QRS complex wave, a T-wave and so on. Because these waveforms are used for a synchronization signal of a medical diagnosis device capable of electrocardiographic synchronization imaging in addition to diagnosis of various types of cardiac disease, automatic detection of such waveforms is important in terms of industrial applications.

When a specific waveform such as an R-wave is detected from an ECG signal, time needed for detection becomes longer in the case of enhancing reliability of the detection, which makes a delay time longer. On the other hand, reliability of the detection declines in the case of shortening a delay time. As just described, existing methods are not satisfactory in terms of achieving both high reliability of detection and a short delay time. Here, high reliability of detection means that probability of correctly detecting a specific waveform to be detected is high and probability of incorrectly detecting a waveform except the specific waveform to be detected is low.

Accordingly, an ECG waveform detecting apparatus, an ECG waveform detecting program and an ECG synchronization imaging apparatus which can achieve both high reliability of detection and a short delay time have been desired.

BRIEF DESCRIPTION OF THE DRAWINGS

In the accompanying drawings:

FIG. 4A is a chart showing positional relationship on a time axis between a waveform pattern WF1, a waveform pattern WF2, and an ECG signal;

FIG. 4B is a chart showing the waveform pattern WF1 as an example of a target waveform to be detected by a first detection unit;

FIG. 4C is a chart showing the waveform pattern WF2 as an example of a target waveform to be detected by a second detection unit;

FIG. 21A and FIG. 21B are diagrams explaining the concept of operation of the detection unit of the ECG waveform detecting apparatus of the second embodiment;

DETAILED DESCRIPTION

ECG waveform detecting apparatuses, ECG waveform detecting programs and ECG synchronization imaging apparatuses (imaging apparatuses) according to embodiments of the present invention will be described with reference to the accompanying drawings. Note that components of the same reference number operate or function in the same way in the following embodiments and thus duplicated explanation is omitted.

Figure 1A:
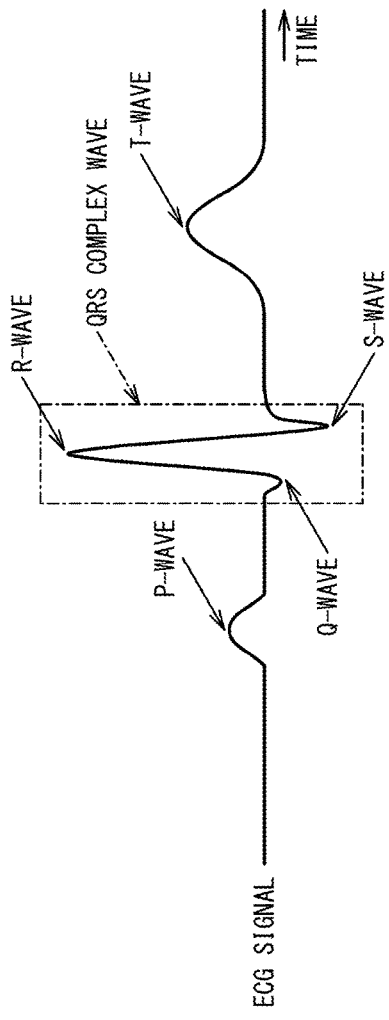
FIG. 1A is a schematic diagram showing an ECG signal which is a detection target of the ECG waveform detecting apparatus of the first embodiment.

FIG. 1A is a schematic diagram showing an ECG signal (a signal corresponding to shape of a cardiac electrogram is referred to as an ECG signal) which is a detection target of the ECG waveform detecting apparatus 1a of the present embodiment. As shown in FIG. 1A, the ECG signal includes specific waves such as a P-wave, an R-wave, a QRS complex wave (a complex wave of a Q-wave, an R-wave and an S-wave), a T-wave and so on.

In each of the following embodiments, examples of detecting an R-wave among the specific waves will be explained. However, examples of detecting an R-wave are only one aspect and the ECG waveform detecting apparatuses 1a to 1e of the following embodiments can detect a waveform other than an R-wave (for example, a P-wave, a QRS complex wave, or a T-wave).

Figure 1B:
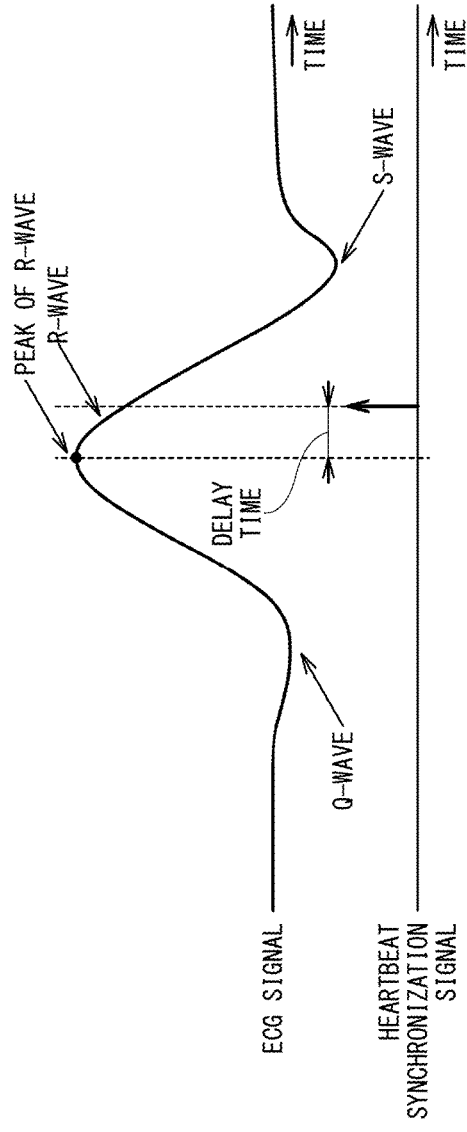
FIG. 1B is a chart obtained by schematically magnifying the vicinity of an R-wave in FIG. 1A.

FIG. 1B is a chart obtained by schematically magnifying the vicinity of the R-wave in FIG. 1A. In FIG. 1B, the time interval from the peak of the R-wave to the heartbeat synchronization signal is defined as a delay time. As an ECG synchronization imaging apparatus (imaging apparatus) 200 capable of imaging in synchronization with heartbeat, for example, there are a CT (Computed Tomography) apparatus, an MRI (Magnetic Resonance Imaging) apparatus, and so on. For example, the ECG synchronization imaging apparatus 200 uses an imaging technique (ECG synchronization imaging technique) in which start timing of data acquisition is determined with reference to a generation position of an R-wave. The ECG synchronization imaging apparatus 200 acquires the heartbeat synchronization signal corresponding to the position of the R-wave, and determines the start timing of data acquisition based on the acquired heartbeat synchronization signal as a reference. Depending on a purpose of imaging, acquisition of imaging data is needed immediately after the R-wave. Therefore, time required for detecting the arrival of an R-wave from an ECG signal and generating a synchronization signal (i.e. a delay time) is needed to be shortened. Thus, it is necessary to detect each R-wave in such a manner that this delay time does not exceed a predetermined value.

For example, a case of an MRI apparatus will be explained below. In an MRI apparatus, various techniques of non-contrast MRA (Magnetic Resonance Angiography) such as an FBI (Fresh Blood Imaging) technique, a Time-SLIP (Time-Spatial Labeling Inversion Pulse) technique are used. An MRI apparatus can obtain vascular images depicting an artery by (a) controlling data acquisition timing with reference to a heartbeat synchronization signal in the data acquisition of the FBI technique so as to obtain diastole images and systole images and (b) calculating subtraction images between the diastole images and the systole images, for example. In addition, an MRI apparatus can obtain blood flow images by, for example, controlling timing of data acquisition and timing of applying a labeling pulse with reference to a heartbeat synchronization signal in the data acquisition of the Time-SLIP technique. As mentioned above, an MRI apparatus controls timing of data acquisition and timing of applying various pulses on the basis of the heartbeat synchronization signal generated from ECG signals as a reference. Since these timings are immediately after an R-wave in many cases, it is desirable that this delay time is as short as possible. Incidentally, the above is only an example. Needless to say, an MRI apparatus acquires imaging data with reference to a heartbeat synchronization signal in other imaging such as various types of imaging whose target is the heart or the like, imaging in which a contrast agent is used.

(The First Embodiment)

Figure 2:
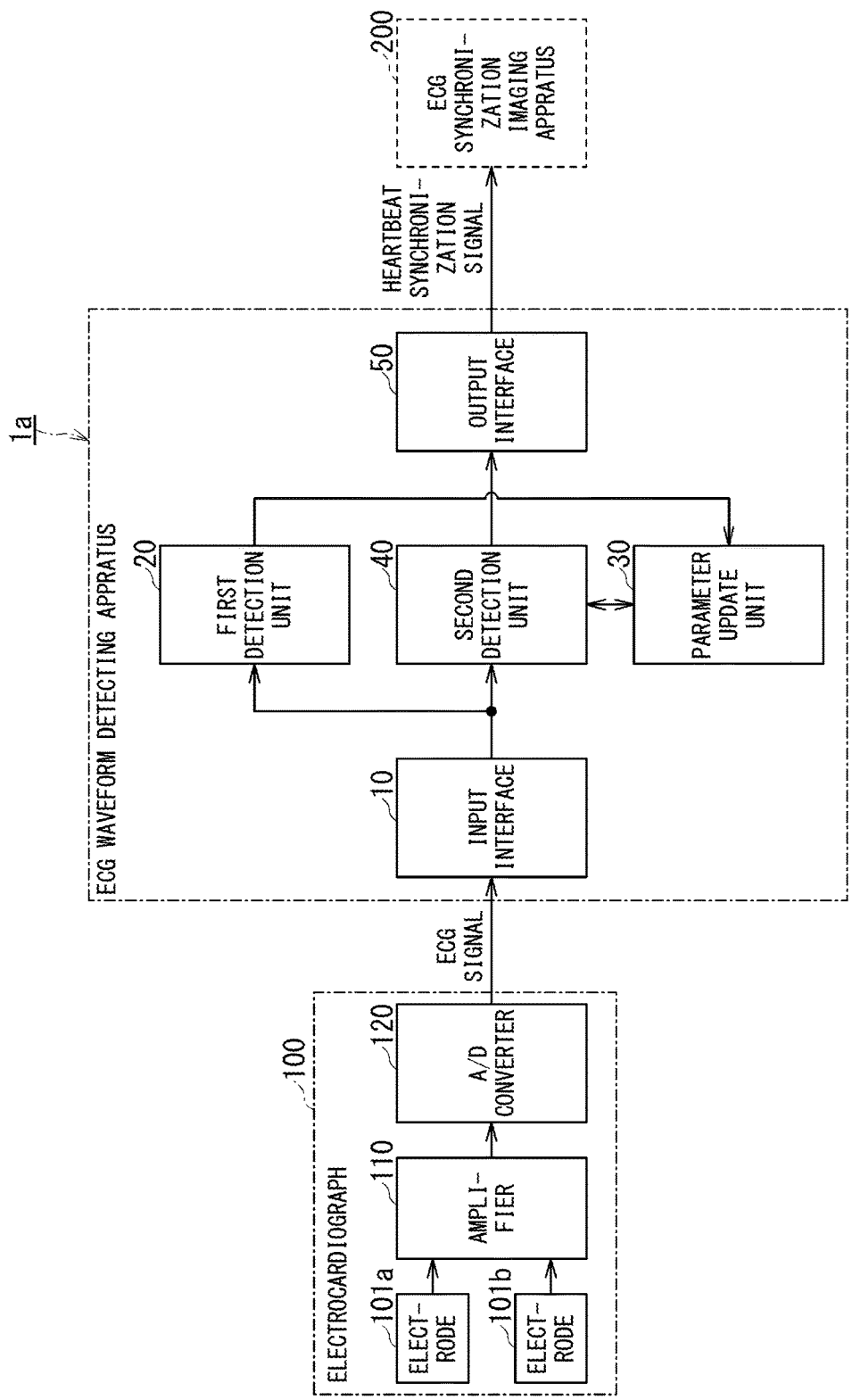
FIG. 2 is a block diagram showing an example of configuration of the ECG waveform detecting apparatus of the first embodiment.

FIG. 2 is a block diagram showing an example of configuration of the ECG waveform detecting apparatus 1a of the first embodiment and configuration of a device/apparatus connected to the ECG waveform detecting apparatus 1a. The electrocardiograph 100 generates ECG signals and transmits the ECG signals to the ECG waveform detecting apparatus 1a. The ECG waveform detecting apparatus 1a generates heartbeat synchronization signals from ECG signals, and transmits the generated heartbeat synchronization signals to the ECG synchronization imaging apparatus 200.

The electrocardiograph 100 includes electrodes 101a and 101b, an amplifier 110, and an A/D (analogue to digital) converter 120. The electrodes 101a and 101b are set on a human body. The amplifier 110 amplifies a weak electrical potential difference between the electrodes 101a and 101b. The A/D converter 120 converts the analogue signal amplified by the amplifier 110 into a digital signal.

Although two electrodes 101a and 101b are illustrated, the number of electrodes of the electrocardiograph 100 is not limited to two. For example, in order to obtain a twelve-lead electrocardiogram, the electrocardiograph 100 may be configured to include four electrodes to be respectively mounted on four limbs and six electrodes to be mounted on the chest part. In addition, instead of the method of obtaining an electrical potential difference between two points of a body, a method of recording an electrical potential difference between a predetermined reference and a mounting point of an electrode may be used.

The ECG waveform detecting apparatus 1a includes an input interface 10, a first detection unit 20, a parameter update unit 30, a second detection unit 40 and an output interface 50.

The input interface 10 acquires ECG signals from the A/D converter 120. The first detection unit 20 detects R-waves included in ECG signals.

The parameter update unit 30 updates the detection parameter by using a part of the waveform used by the first detection unit 20 for detecting R-waves. The second detection unit 40 detects R-waves by using the updated detection parameters, and generates heartbeat synchronization signals. The output interface 50 transmits the generated heartbeat synchronization signals to the ECG synchronization imaging apparatus 200.

Each of functions of the corresponding units of the ECG waveform detecting apparatus 1a may be configured of hardware such as an ASIC (Application Specific Integration Circuit), an FPGA (Field-Programmable Gate Array), may be achieved by using software processing, or may be achieved by combination of hardware and software processing. When the functions of the units are achieved by software processing, they can be realized by causing the computer 300 illustrated in FIG. 3 to execute predetermined programs.

Figure 3:
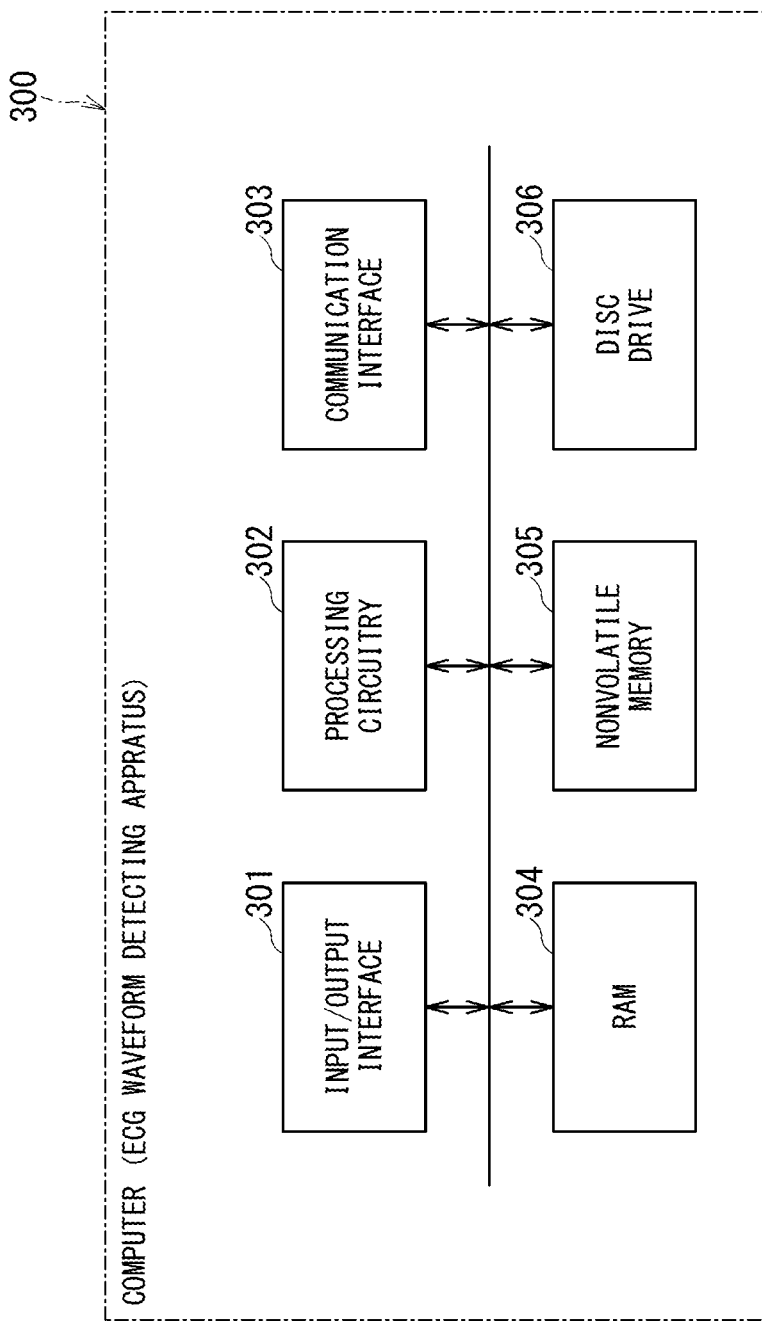
FIG. 3 is a diagram showing the hardware structure of the ECG waveform detecting apparatus of the first embodiment.

The computer 300 illustrated in FIG. 3 includes an input/output interface 301, processing circuitry 302, a communication interface 303, a RAM (Random Access Memory) 304, a nonvolatile memory 305, and a disc drive 306.

The nonvolatile memory 305 is, for example, a storage device such as a hard disc, a flash memory or the like, and stores various programs and data. The processing circuitry 302 reads programs for achieving operation of each component of the ECG waveform detecting apparatus 1a from the nonvolatile memory 305 into the RAM 304, and executes these programs. Other than them, programs stored in a recording medium such as a magnetic disk, an optical disc, a USB memory may be read from the disc drive 306 or the input/output interface 301. In addition, such programs may be downloaded from an external server via the communication interface 303.

The processing or the functions of the respective units (20, 30, and 40) except the input interface 10 and the output interface 50 of the ECG waveform detecting apparatus 1a can be implemented by the processing circuitry 302 in FIG. 3 or the CPU executing one or more programs stored in a nonvolatile memory 305 or a RAM (Random Access Memory) 304 in FIG. 3. The same holds true for the ECG waveform detecting apparatuses 1a, 1b, 1c, and 1d of the other embodiments and their modifications to be explained below.

As shown in FIG. 4, the first detection unit 20 and the second detection unit 40 of the ECG waveform detecting apparatus 1a each detect waveforms different from each other. It is preferable that the waveform detected by the first detection unit 20 is detectable more easily than the waveform detected by the second detection unit 40. The second detection unit 40 is dynamically tuned by using the detection result of the first detection unit 20. In other words, the detection parameter used by the second detection unit 40 is dynamically updated in accordance with the detection result of the first detection unit 20. Even if the target waveform to be detected by the second detection unit 40 is not a waveform with high reliability of detection, the detection reliability of the second detection unit 40 can be enhanced by updating the detection parameter. The heartbeat synchronization signals are generated on the basis of the detection result of the second detection unit 40.

Hereinafter, an example of detecting an R-wave of an ECG signal inputted on mainly a real-time basis will be explained. The ECG waveform detecting apparatus 1a, however, may use an ECG signal which is once stored in an appropriate memory.

FIG. 4B is a chart showing a waveform pattern WF1 as an example of a target waveform to be detected by the first detection unit 20. On the other hand, FIG. 4C is a chart showing a waveform pattern WF2 as an example of a target waveform to be detected by the second detection unit 40. FIG. 4A is a chart showing positional relationship on a time axis between the waveform pattern WF1, the waveform pattern WF2 and an ECG signal.

The first detection unit 20 performs detection during the first detection period corresponding to a waveform within a predetermined range (waveform pattern WF1) including the entire R-wave. The first detection period is a period composed of the following three spans: a span of an R-wave, a span which starts earlier than this R-wave by a predetermined time and ends immediately before this R-wave, and a span which starts immediately after this R-wave and lasts for a predetermined time.

Meanwhile, the second detection unit 40 performs detection during the second detection period which corresponds to the peak of the R-wave and a waveform within a predetermined range (waveform pattern WF2) earlier than this peak by a predetermined time.

The first detection unit 20 detects the target waveform (the waveform pattern WF1) whose time width is wide. Since the result of the detection of the waveform pattern WF1 is outputted at the end of the first detection period (i.e., at the end of WF1), the delay time of detecting an R-wave becomes rather large.

By contrast, the second detection unit 40 can output the result of the detection of the waveform pattern WF2 immediately after the peak of the R-wave. Thus, it is possible for the second detection unit 40 to make the delay time of detecting an R-wave shorter than that of the first detection unit 20. Since the second detection period is shorter than the first detection period, there may be a possibility that detection reliability of the second detection unit 40 is lowered.

However, in the ECG waveform detecting apparatus 1a of the first embodiment, the detection reliability of the second detection unit 40 can be enhanced by dynamically updating the detection parameter used in the second detection unit 40 on the basis of the detection result of the first detection unit 20.

Figure 5:
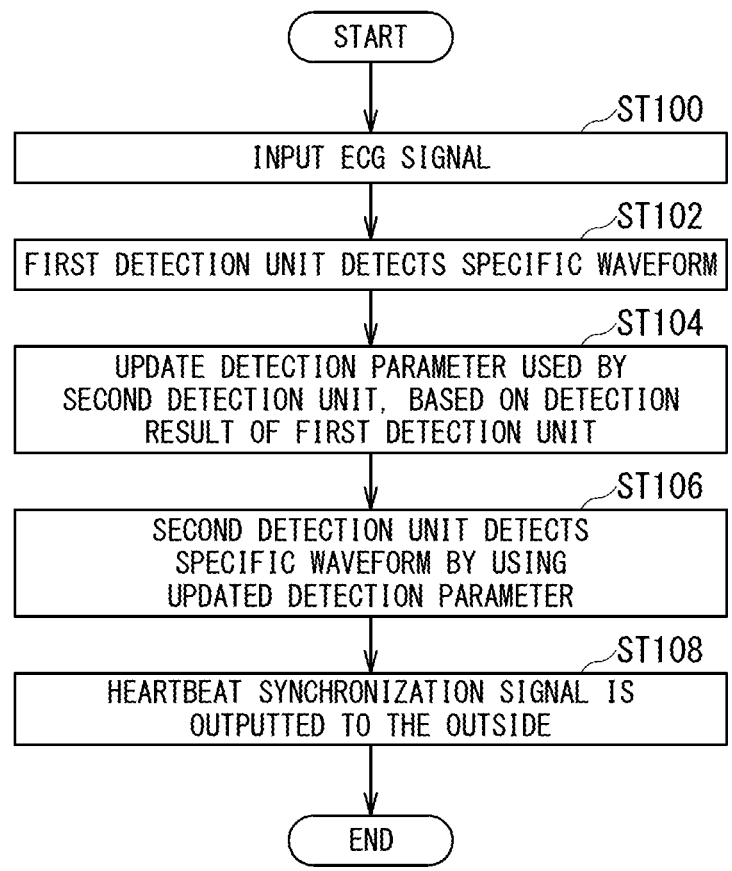
FIG. 5 is a flowchart showing an example of a general outline of processing of the ECG waveform detecting apparatus of the first embodiment.

FIG. 5 is a flowchart showing an example of a general outline of processing of the ECG waveform detecting apparatus 1a. First, in the step ST100, the input interface 10 of the ECG waveform detecting apparatus 1a inputs an ECG signal as a time-series signal. The ECG signal is, for example, a signal sampled at a constant sampling interval, for example, a sampling interval of 1 millisecond.

In the step ST102, the first detection unit 20 detects an R-wave from the inputted ECG signal. Specifically, as mentioned above, the first detection unit 20 detects an arrival timing of the waveform pattern WF1, which includes an R-wave, from the time-sequentially inputted ECG signal, by using the first detection period. The first detection unit 20 may execute the detection processing at the same interval as the sampling period of ECG signals, or at a longer interval than the sampling period. Note that the purpose of the detection performed by the first detection unit 20 is to update the detection parameter used by the second detection unit 40 on the basis of its detection result so as to enhance the detection accuracy of the second detection unit 40. Thus, the execution interval of the detection processing of the first detection unit 20 may be longer than that of the second detection unit 40.

In the step ST104, the parameter update unit 30 updates the detection parameter used in the second detection unit 40, by using detection result obtained by the first detection unit 20. Specifically, for example, when the waveform pattern WF1 shown in FIG. 4B is detected, the detection parameter of the second detection unit 40 is updated by using the detected ECG signal so that the waveform pattern WF2 (FIG. 4C) arriving next is more reliably detected.

Meanwhile, there may be a case where the second detection unit 40 erroneously detects a T-wave as an R-wave, although the first detection unit 20 does not erroneously detects a T-wave as an R-wave. In such case, as an alternative updating method, the detection parameter for the second detection unit 40 may be updated so that the second detection unit 40 never erroneously detects a T-wave as an R-wave.

In the step ST106, the second detection unit 40 detects an R-wave from the inputted ECG signal, by using the updated detection parameter. Specifically, as mentioned above, an arriving timing of the waveform pattern WF2, which includes an R-wave, is detected from the time-sequentially inputted ECG signals, by using the second detection period. Although the execution interval of the detection processing performed by the second detection unit 40 may be the same as the sampling interval of ECG signals, for example, 1 millisecond interval, it may be performed at execution interval longer than the sampling interval, for example, 5 millisecond interval. However, it should be noted that the execution interval of the detection processing of the second detection unit 40 directly influences the delay time from the peak of an R-wave. Thus, the execution interval of the second detection unit 40 should be equal to or shorter than a predetermined maximum acceptable value of a delay time.

In the step ST108, the detection result (i.e. the heartbeat synchronization signal) is outputted to the external ECG synchronization imaging apparatus 200 when the second detection unit 40 detected an R-wave in the step ST106.

For the case where the ECG synchronization imaging apparatus 200 is an MRI apparatus, the ECG synchronization imaging apparatus 200 controls components such as an RF (Radio Frequency) coil configured to transmit RF pulses, a reception unit configured to sample magnetic resonance signals, so that transmission of an RF pulse and a labeling pulse for data acquisition is performed at the timing when a preliminarily determined time elapses from the reception timing of the heartbeat synchronization signal outputted from the ECG waveform detecting apparatus 1a.

Incidentally, the above processing algorithm is only an example. For example, the operation of detecting a specific waveform in the first detection unit 20 so as to update the detection parameter used by the second detection unit 40 and the operation of detecting a specific waveform in the second detection unit 40 do not necessarily need to be performed as a series of operations as shown in FIG. 5. These operations may be respectively performed in parallel with each other.

The first detection unit 20 and the second detection unit 40 can use various types of known detection methods. For example, the first detection unit 20 can use any one of the detection methods listed in the following non-patent document 1.

[Non-patent Document 1] Bert-Uwe Kohler et al., "The Principles of Software QRS Detection", IEEE Engineering in Medicine and Biology, pp. 42-57, January/February 2002.

The above non-patent document discloses a detection method using a detection parameter which can be dynamically updated and a detection method without using a detection parameter which can be dynamically updated are introduced in the non-patent document 1. The first detection unit 20 can use either of the detection methods.

Meanwhile, the second detection unit 40 can use a detection method using the detection parameter which is dynamically updated out of the detection methods listed in the non-patent document 1. As an example of the detection method using the detection parameter which is be dynamically updated, there is an Adaptive Filter that updates coefficients of an FIR (Finite Impulse Response) filter on the basis of an input signal, or a method using a Matched Filter that updates templates on the basis of an input signal. In addition, a neural network that updates its internal state by using an input signal can also be used. The second detection unit 40 can use any one of these methods.

In the detection processing of the first embodiment, plural detection methods are used cooperatively. Specifically, a detection method that has a shorter delay time is used in the second detection unit 40, while a detection method that has a longer delay time but has high detection reliability is used in the first detection unit 20. Because the second detection unit 40 performs the detection processing by using the detection parameter which is dynamically updated, highly reliable detection is achieved with a short delay time.

Hereinafter, configuration of a Matched Filter type ECG waveform detecting apparatus 1a detecting an R-wave with a Matched Filter which uses a template and its operation will be explained.

Figure 6:
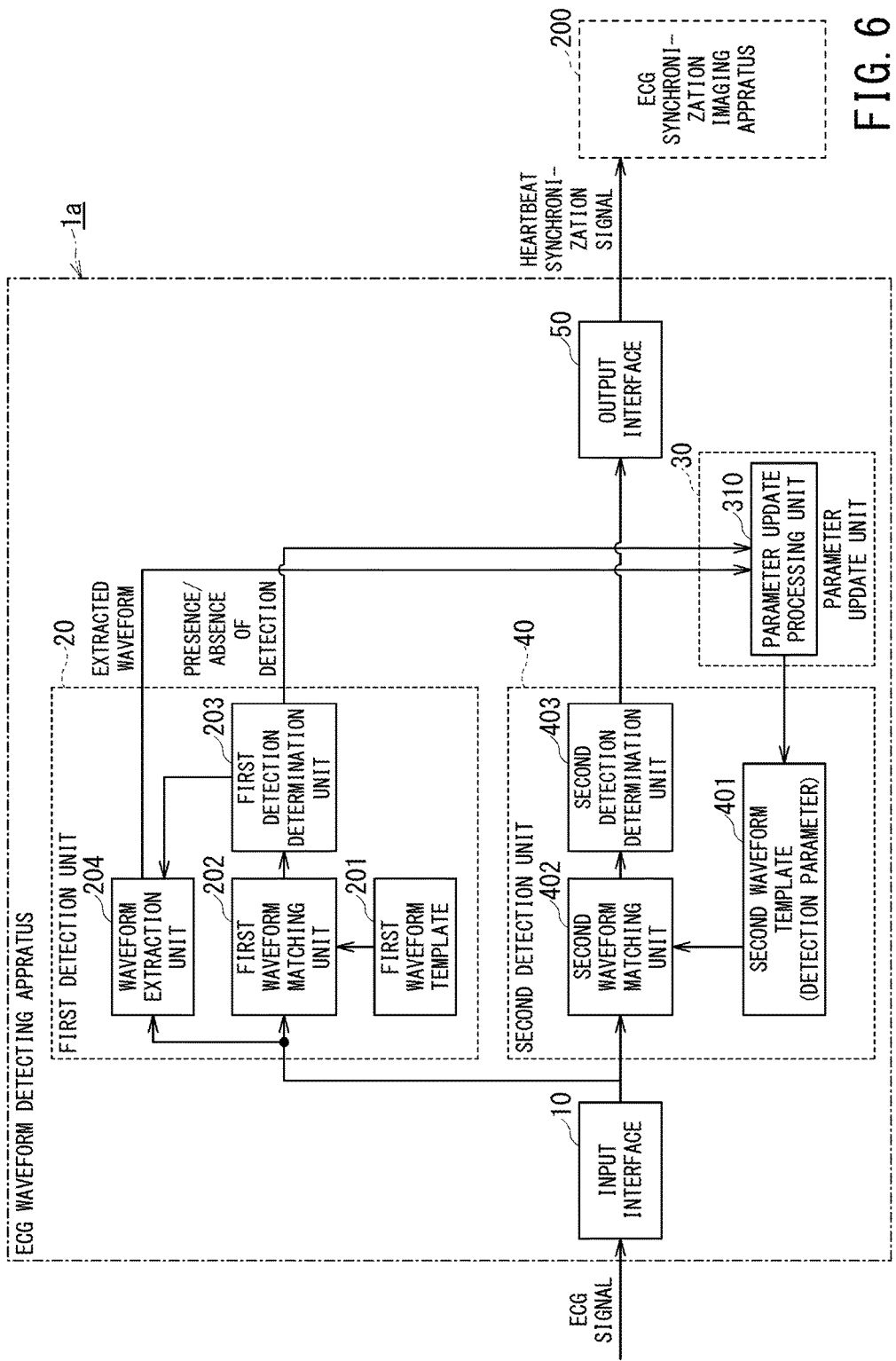
FIG. 6 is a block diagram showing an example of configuration of the ECG waveform detecting apparatus of a Matched Filter type in the first embodiment.

FIG. 6 is a block diagram showing an example of configuration of the ECG waveform detecting apparatus 1*a* of Matched Filter type in the first embodiment.

As shown in FIG. 6, the first detection unit 20 of the ECG waveform detecting apparatus 1*a* includes a first waveform template 201, a first waveform matching unit 202, a first detection determination unit 203 and a waveform extraction unit 204. Meanwhile, the second detection unit 40 includes a second waveform template 401, a second waveform matching unit 402 and a second detection determination unit 403.

Here, the first waveform template 201 is a template corresponding to the waveform pattern WF1 shown in FIG. 4B and is a template of a waveform composed of the following three spans: a span of an R-wave, a span which starts earlier than the R-wave by a predetermined time and ends immediately before the R-wave, and a span which starts immediately after the R-wave and lasts for a predetermined time.

On the other hand, the second waveform template 401 is a template corresponding to the waveform pattern WF2 shown in FIG. 4C and is a template of a waveform of the peak of the R-wave and a waveform within a predetermined range temporally earlier than this peak by a predetermined time. Precisely, the second waveform template 401 includes a range which is temporally slightly later than the peak of the R-wave, and this temporally subsequent range is equal to the delay time (FIG. 1B). For example, when the peak position of the R-wave is defined as zero millisecond (reference) and the range of the second waveform template 401 is assumed to be from −200 millisecond to +10 millisecond, 10 millisecond corresponds to the delay time. When the acceptable delay time is α millisecond, the period of the second waveform template 401 is set to a period from −β millisecond to +α millisecond. Thereby, the second detection unit 40 can detect an R-wave with a delay time of α millisecond from the peak of an R-wave. Incidentally, α or β does not necessarily need to be a positive value but may be zero or a negative value.

In addition, the position of the front end of the second waveform template 401 (−β millisecond in the above example) can be set to a large value, because it is irrelevant to a delay time. For example, like the waveform pattern WF2 shown in FIG. 4C, the span prior to the P-wave may be included.

Figure 7:
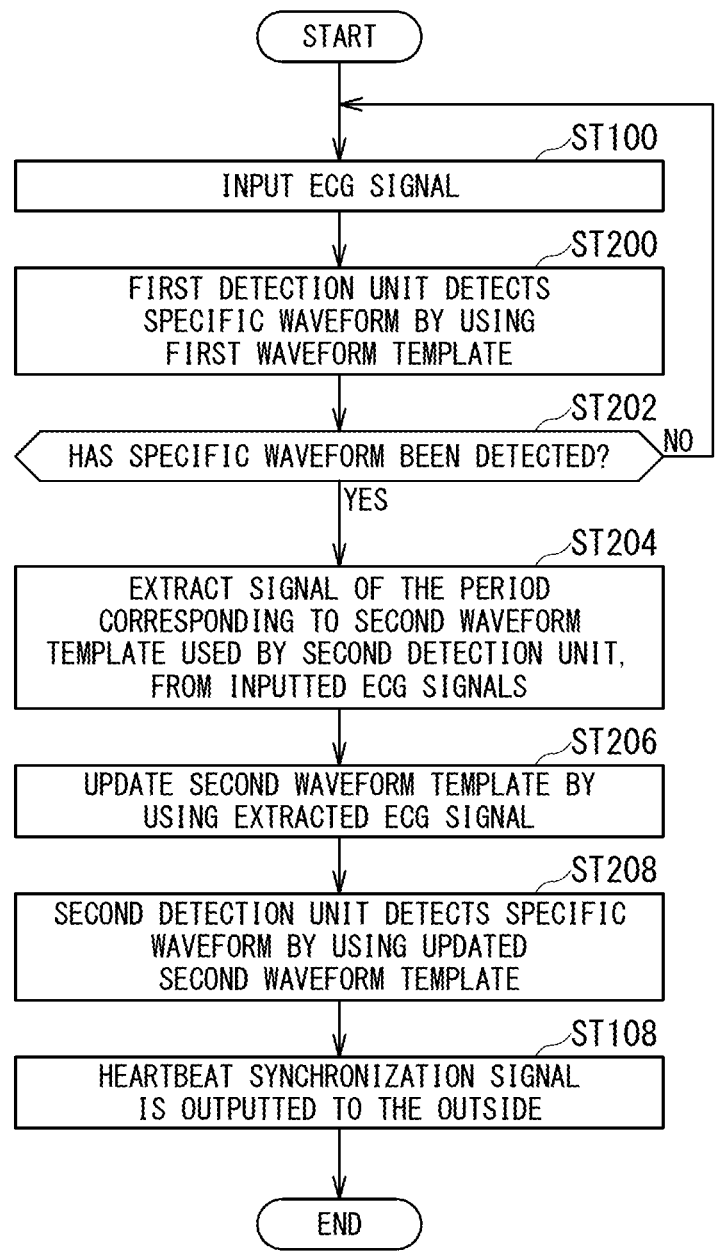
FIG. 7 is a flowchart showing an example of processing performed by the ECG waveform detecting apparatus of the first embodiment shown in FIG. 6.

FIG. 7 is a flowchart showing an example of processing performed by the ECG waveform detecting apparatus 1*a* of Matched Filter type. The flowchart of FIG. 7 adapts the flowchart FIG. 5 to the ECG waveform detecting apparatus 1*a* of Matched Filter type and more concretely describes its flow.

In the step ST100, on reception of an ECG signal, this ECG signal is outputted to the first detection unit 20 and the second detection unit 40.

In the step ST200, the first detection unit 20 detects an R-wave by using the first waveform template 201 corresponding to the waveform pattern WF1. The first waveform matching unit 202 matches the ECG signal, which is time-sequentially outputted from the input interface 10, with the first waveform template 201 by using matching processing. The first waveform matching unit 202 transmits a matched result to the first detection determination unit 203. The first detection determination unit 203 detects arrival of the waveform pattern WF1 and the position of an R-wave included in the waveform pattern WF1 on the basis of the matched result. By detecting timing when a similarity between a preliminarily prepared waveform pattern and a waveform of an ECG signal becomes higher than a predetermined reference, the arrival of the waveform pattern WF1 can be detected, and thus the position of an R-wave also can be detected. In the following embodiment, an example of applying a threshold value to the matched result, i.e., to the similarity, will be explained.

One example of the matching processing is processing of calculating a cross-correlation function between the ECG signal and the first waveform template 201. In this case, the cross-correlation function is outputted in time series from the first waveform matching unit 202 to the first detection determination unit 203. When the ECG signal matches with the first waveform template 201, the cross-correlation function becomes large. The first detection determination unit 203 determines that an R-wave is detected, when the cross-correlation function is larger than a threshold value, for example.

Another example of the matching processing is processing of calculating a difference between the ECG signal and the first waveform template 201. In this case, the difference is outputted in time series from the first waveform matching unit 202 to the first detection determination unit 203. When the inputted ECG signal matches with the first waveform template 201, the difference becomes small. The first detection determination unit 203 determines that an R-wave is detected, when the difference is smaller than a threshold value, for example.

In the step ST202, the first detection determination unit 203 determines whether it has detected an R-wave or not.

Figure 8:
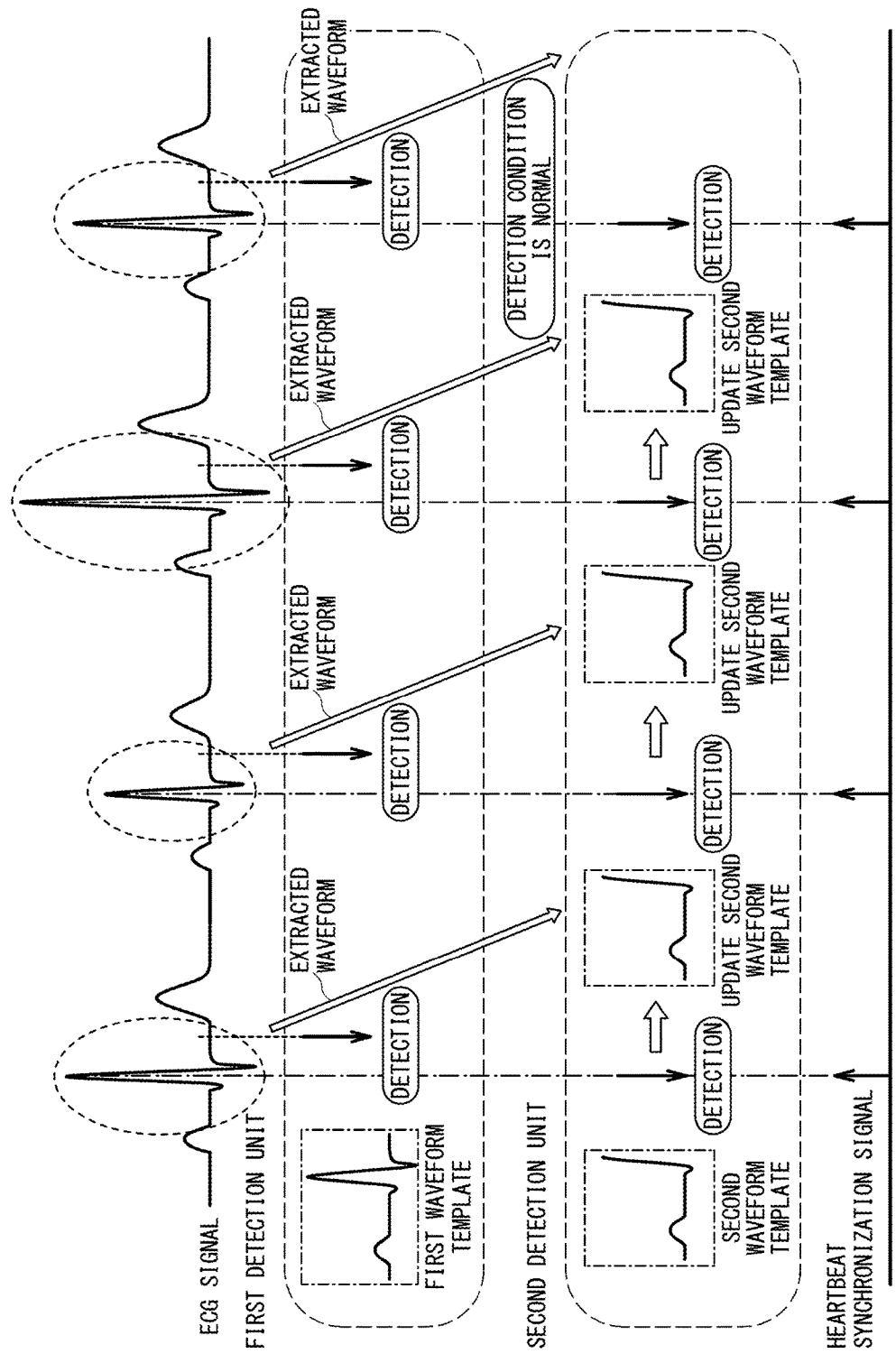
FIG. 8 is an operational timing chart of the ECG waveform detecting apparatus of the first embodiment shown in FIG. 6.

FIG. 8 indicates an operational timing chart of the ECG waveform detecting apparatus 1*a*. In FIG. 8, the top part shows ECG waveforms, the second top part shows the operational outline of the first detection unit 20, the third top part shows the operational outline of the second detection unit 40, and the bottom part shows heartbeat synchronization signals outputted from the second detection unit 40.

FIG. 8 shows an example in which an external disturbance signal is not superimposed on ECG signals. Each time an R-wave arrives, the first detection unit 20 detects the waveform pattern WF1 including an R-wave. The detection of an R-wave by the first detection unit 20 is performed by using a long-span signal including the periods before and after the R-wave. Note that because this detection result is outputted at the back end of the first detection period or the waveform pattern WF1, it is detected with a certain delay time.

In the step ST204 of FIG. 7, the waveform extraction unit 204 extracts a signal of a period, which corresponds to the second waveform template, from the ECG signal. When an acceptable delay time with respect to the peak position of an R-wave is assumed to be α millisecond, the waveform extraction unit 204 extracts the signal of the period between −β millisecond and +α millisecond from the ECG signal, and transmits the extracted signal waveform to the parameter update unit 30.

In the step ST206, the parameter update processing unit 310 updates the second waveform template by using the ECG signal extracted in the step ST204. The parameter update processing unit 310 may update the second waveform template by substituting the extracted ECG signal for the last second waveform template, each time an R-wave is detected by the first detection unit 20.

The parameter update processing unit 310 may update the second waveform template by calculating a weighted sum of the second waveform template one before the current template and the extracted latest ECG signal. For example, the second waveform template may be updated by using the formula below.

$$T_2(n)=W1*T_2(n-1)+W2*Es(n)$$

Here, $T_2(n-1)$ is the second waveform template one before the current template, $T_2(n)$ is the second waveform template 401 immediately after being updated, Es(n) is the extracted latest ECG signal, n is the update number, W1 and W2 are weighting coefficients. The sum of the weighting coefficients W1 and W2 is, for example, 1.0. The ratio between W1 and W2 is determined in terms of which of the past ECG signals and the latest ECG signal is more important to what degree. For example, when greater importance is put on the latest ECG signal than the past ECG signals, W2 is set to a value larger than W1.

On the other hand, when greater importance is put on the past ECG signals than the latest ECG signal, W1 is set to a value larger than W2. In this case, for example, they are set to W1=0. 9 and W2=0. 1. The updated second waveform template 401 is transmitted to the second detection unit 40.

In the step ST208, the second detection unit 40 detects an R-wave by using the updated second waveform template 401 with a short delay time. The method of detecting an R-wave by the second detection unit 40 may be the same as that of the first detection unit 20. The second detection unit 40 and the first detection unit 20 use respective waveform templates which are different from each other.

The second detection unit 40 uses the second waveform template 401 corresponding to the waveform pattern WF2 whose delay time is shortly set. Moreover, the second detection unit 40 uses the second waveform template 401 updated by the latest ECG waveform. Under the above conditions, the second waveform matching unit 402 matches the ECG signal time-sequentially outputted form the input interface 10 with the updated second waveform template 401, by using the matching processing. The second waveform matching unit 402 transmits the matched result to the second detection determination unit 403. The second detection determination unit 403 detects the waveform pattern WF2 by applying a threshold value to the matching result. The second detection determination unit 403 detects an R-wave included in the waveform pattern WF2 by detecting the waveform pattern WF2. The second detection unit 40 may perform any one of (a) processing of calculating a cross-correlation function between the ECG signal and the updated second waveform template 401 and (b) processing of calculating a difference between the ECG signal and the updated second waveform template 401.

In the second waveform template 401, the period after the peak of its R-wave is short. Therefore, as shown in the third top part and the bottom part of FIG. 8, the second detection unit 40 can detect an R-wave with a short delay time. The second detection unit 40 can output a heartbeat synchronization signal with a short delay time from the peak of an R-wave. The time width of the second waveform template 401 used by the second detection unit 40 is shorter than the time width of the first waveform template 201 used by the first detection unit 20. Therefore, from the view point of the length of waveform template, the detection reliability of the second detection unit 40 may be inferior to that of the first detection unit 20. However, as mentioned above, since the second detection unit 40 uses the second waveform template 401 updated with the waveform of the latest ECG signal, deterioration of the detection reliability is avoided, and thus high detection reliability can be assured. FIG. 9A to FIG. 9D are diagrams explaining the effect of updating the second waveform template 401. FIG. 9A to FIG. 9D are an example of a case where subtraction processing is used as the matching processing. The second waveform matching unit 402 calculates a difference value between the second waveform template 401 and an ECG signal. In each graph shown in FIG. 9A to FIG. 9D, the vertical axis indicates a difference value and a horizontal axis indicates time.

Figure 9A:
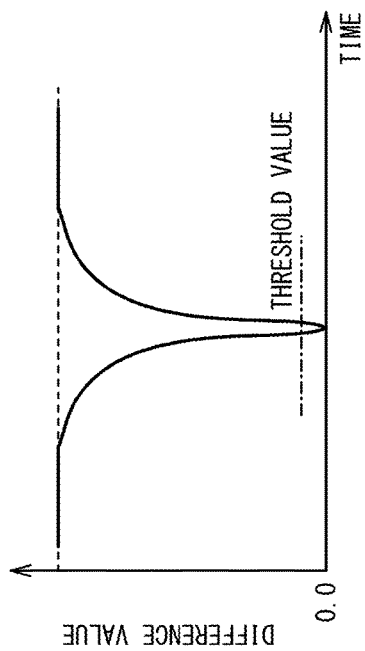
FIG. 9A to FIG. 9D are diagrams conceptually explaining that the detection reliability improves by updating a waveform template.
Figure 9B:
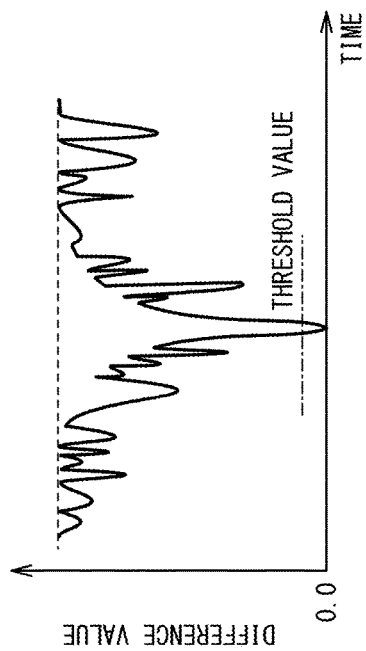

FIG. 9A and FIG. 9B are diagrams each showing the difference value on the assumption that any external disturbance is not superimposed on the ECG signal. FIG. 9A is an example of a case where the second waveform template is not updated, and FIG. 9B is an example of a case where the second waveform template is updated. In both cases, the difference value is minimized at the timing when the waveform of the inputted ECG signal is the most similar to the shape of the waveform template.

However, an ECG signal is not necessarily constant, and the waveform of the ECG signal and the peak height of the R-wave are different for each patient. In addition, even if the same patient is imaged by using a CT apparatus, an MRI apparatus, or the like, the waveform of the ECG signal is not necessarily the same but temporally is changed. Therefore, when the difference value is calculated by using the waveform template of the same shape on a consistent basis, the shape of the waveform template does not accord with the shape of the waveform of the ECG signal to be sequentially inputted. Therefore, as shown in FIG. 9A, at the peak (minimum point) of the difference value, the minimum value does not become zero. In addition, because the peak value of the R-wave in the ECG signal is temporally changed, the peak value (minimum value) of the difference value itself also is temporally changed as shown with the bidirectional arrow in FIG. 9A.

By contrast, the temporal fluctuation can be reflected on the shape of the second waveform template 401 by updating the second waveform template 401 with the use of the ECG signal within the range according to the latest detection result of the first detection unit 20. As a result, even if the ECG signal is temporally changed, the peak value of the difference value between both can be maintained at around zero.

The difference value is transmitted from the second waveform matching unit 402 to the second detection determination unit 403. The second detection determination unit 403 performs determination with the use of the threshold value. The second detection determination unit 403 determines that the waveform has been detected, when the difference value is smaller than the threshold value. By updating the second waveform template 401 in accordance with the detection result of the first detection unit 20, stable determination with the use of the threshold value is achieved. This effect becomes remarkable, especially when external disturbance and/or noise is superimposed on the ECG signal. When external disturbance and noise are superimposed on the ECG signal, the external disturbance and noise are also superimposed on the difference value between the waveform template and an ECG signal, and thus the difference value is significantly changed.

Figure 9C:
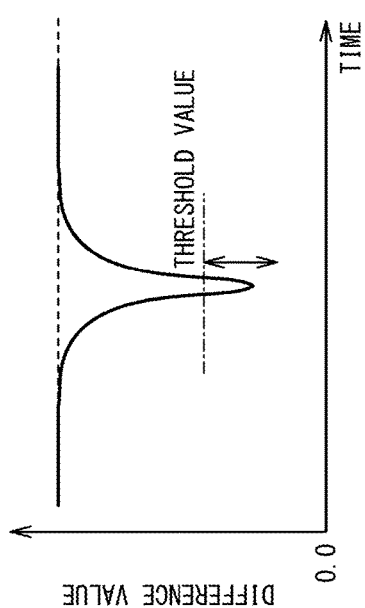
Figure 9D:
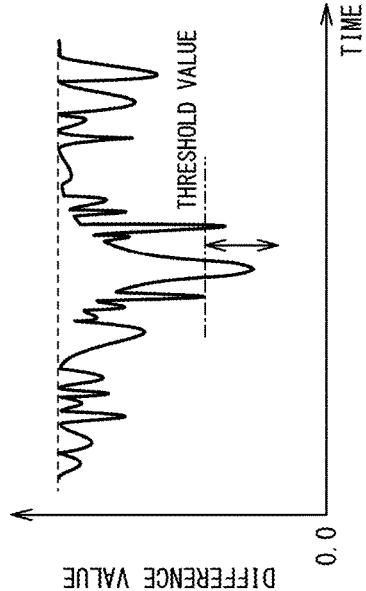

FIG. 9C and FIG. 9D are schematic diagrams showing the states where the external disturbance and noise are superimposed on the waveforms of FIG. 9A and FIG. 9B, respectively.

When the second waveform template is not updated (FIG. 9C), the peak of the difference value becomes larger than zero and the peak value is changed. Therefore, in order to reliably detect the peak, it is inevitable that the threshold value is set to a large value (separated from zero). In this case, the probability of erroneously detecting external disturbance and/or noise becomes higher, which makes it difficult to detect the peak of the difference values with high reliability.

On the other hand, when the second waveform template is updated (FIG. 9D), the peak value of the difference value can be maintained at around zero. Therefore, even if the threshold value is set to a small value, the peak value of the difference value can be detected reliably and stably. By setting the threshold value to a small value, the probability of erroneously detecting external disturbance and/or noise is reduced. As a result, the peak value of difference values can be detected with high reliability.

Incidentally, the second waveform matching unit 402 may calculate the cross-correlation function as the matching processing. In this case, detection of high reliability can be also achieved by updating the second waveform template. Note that, although the peak is made into a downward convex shape in the case of the difference value, the peak is made into an upward convex shape in the case of the cross-correlation function. Therefore, the second detection determination unit 403 determines that the waveform has been detected, when the cross-correlation function is larger than the threshold value.

Returning to FIG. 7, in the step ST208, when the second detection unit 40 detects an R-wave, the output interface 50 outputs a heartbeat synchronization signal to the ECG synchronization imaging apparatus 200 installed outside.

As mentioned above, according to the ECG waveform detecting apparatus 1a of the present embodiment, the second waveform template which is set so as to shorten a delay time is used. Thereby, a specific waveform such as an R-wave can be detected with a short delay time in the second detection unit 40. In addition, by updating the second waveform template (i.e. the detection parameter) used in the second detection unit 40, a specific waveform such as an R-wave can be detected with high reliability.

(The First Modification of the First Embodiment)

Figure 10:
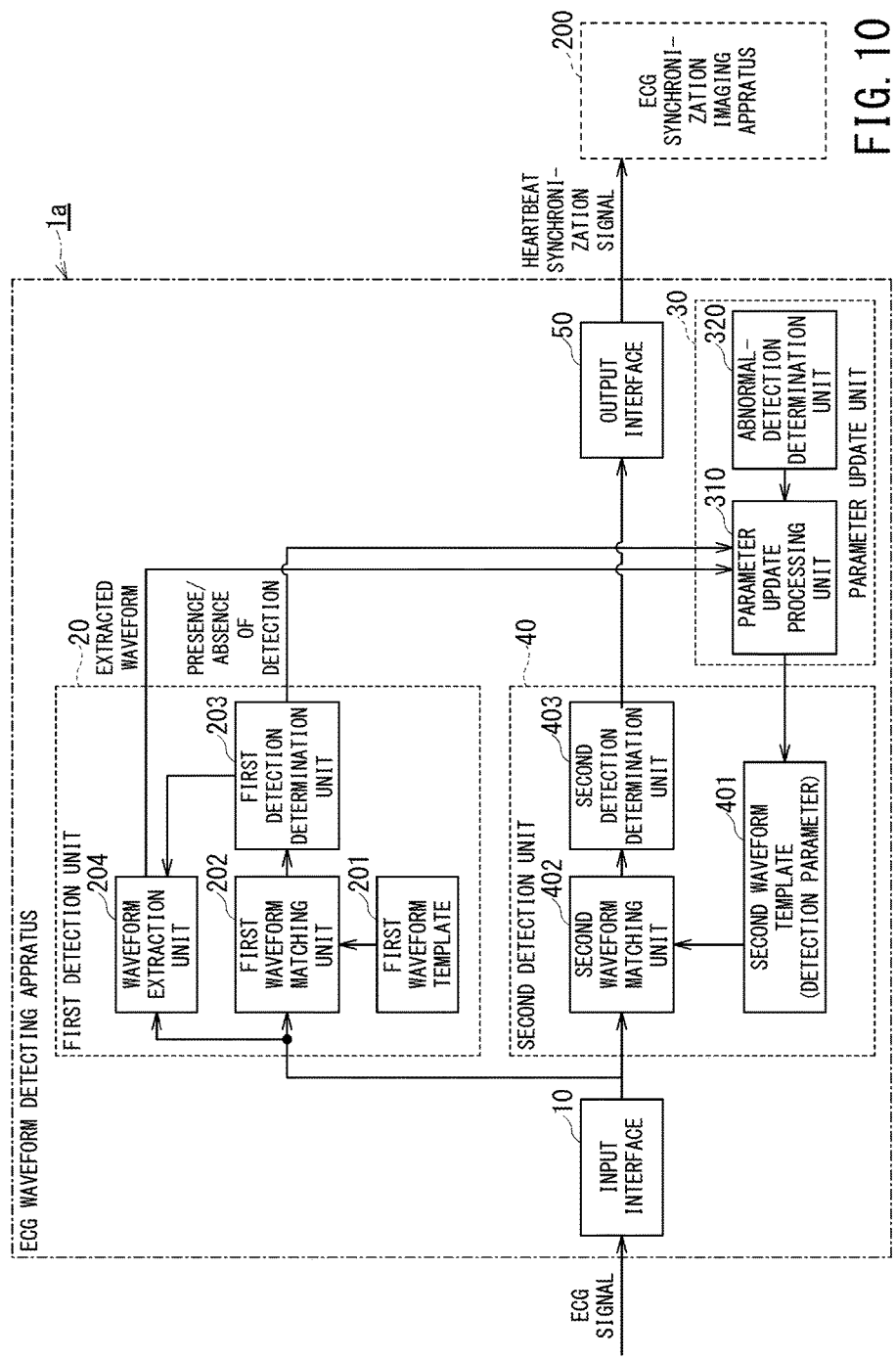
FIG. 10 is an example of configuration of the ECG waveform detecting apparatus according to the first modification of the first embodiment.

FIG. 10 is a block diagram showing an example of configuration of the ECG waveform detecting apparatus 1a according to the first modification of the first embodiment. The difference between this first modification and the ECG waveform detecting apparatus 1a (FIG. 6) of the above-mentioned first embodiment lies in that the parameter update unit 30 includes an abnormal-detection determination unit 320 in addition to the parameter update processing unit 310.

The abnormal-detection determination unit 320 determines whether the detection condition in the first detection unit 20 is abnormal or not. An abnormal detection indicates a condition where frequency of false detection (i.e. detecting a waveform other than a target waveform, i.e., an R-wave) is higher than a predetermined reference. When the detection condition is abnormal, the second detection unit 40 does not perform update of the detection parameter. In other words, the second detection unit 40 stops update processing of the second waveform template.

Figure 11:
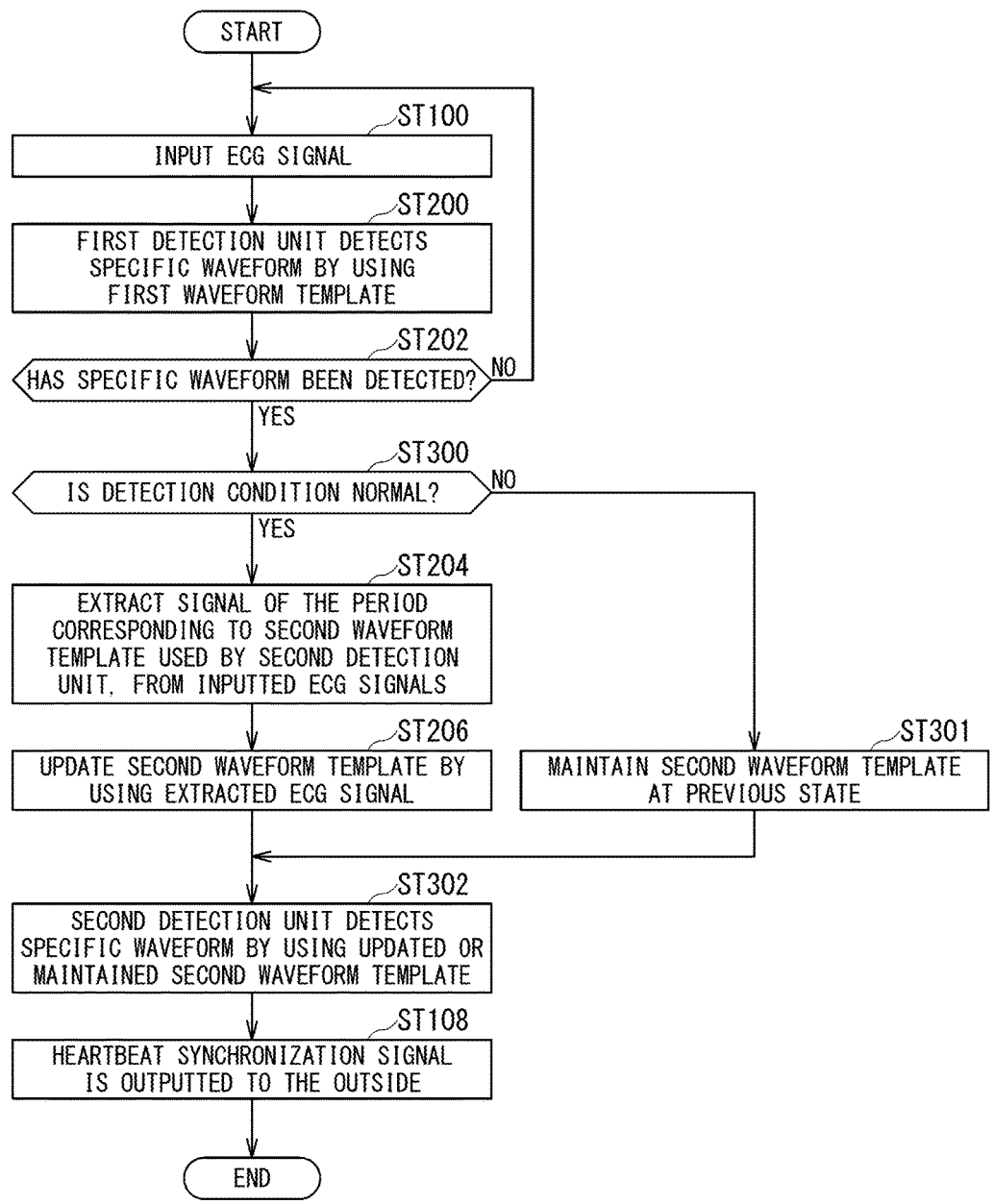
FIG. 11 is a flowchart showing an example of processing performed by the ECG waveform detecting apparatus of the first modification of the first embodiment.

FIG. 11 is a flowchart showing an example of processing performed by the ECG waveform detecting apparatus 1a of the first modification of the first embodiment. FIG. 11 is different from the flowchart of the ECG waveform detecting apparatus 1a of the first embodiment (FIG. 7) in that processing of the step ST300 and the step ST301 is added.

In the step ST300, the abnormal-detection determination unit 320 determines whether the detection condition in the first detection unit 20 is normal or abnormal. When the detection condition is normal, the process proceeds to the step ST204 and the second waveform template is updated. On the other hand, when the detection condition is abnormal, update processing of the second waveform template is stopped and the previous state is maintained as to the second waveform template.

In the step ST302, the second detection unit 40 detects an R-wave by using either the updated second waveform template or the maintained second waveform template.

Figure 12:
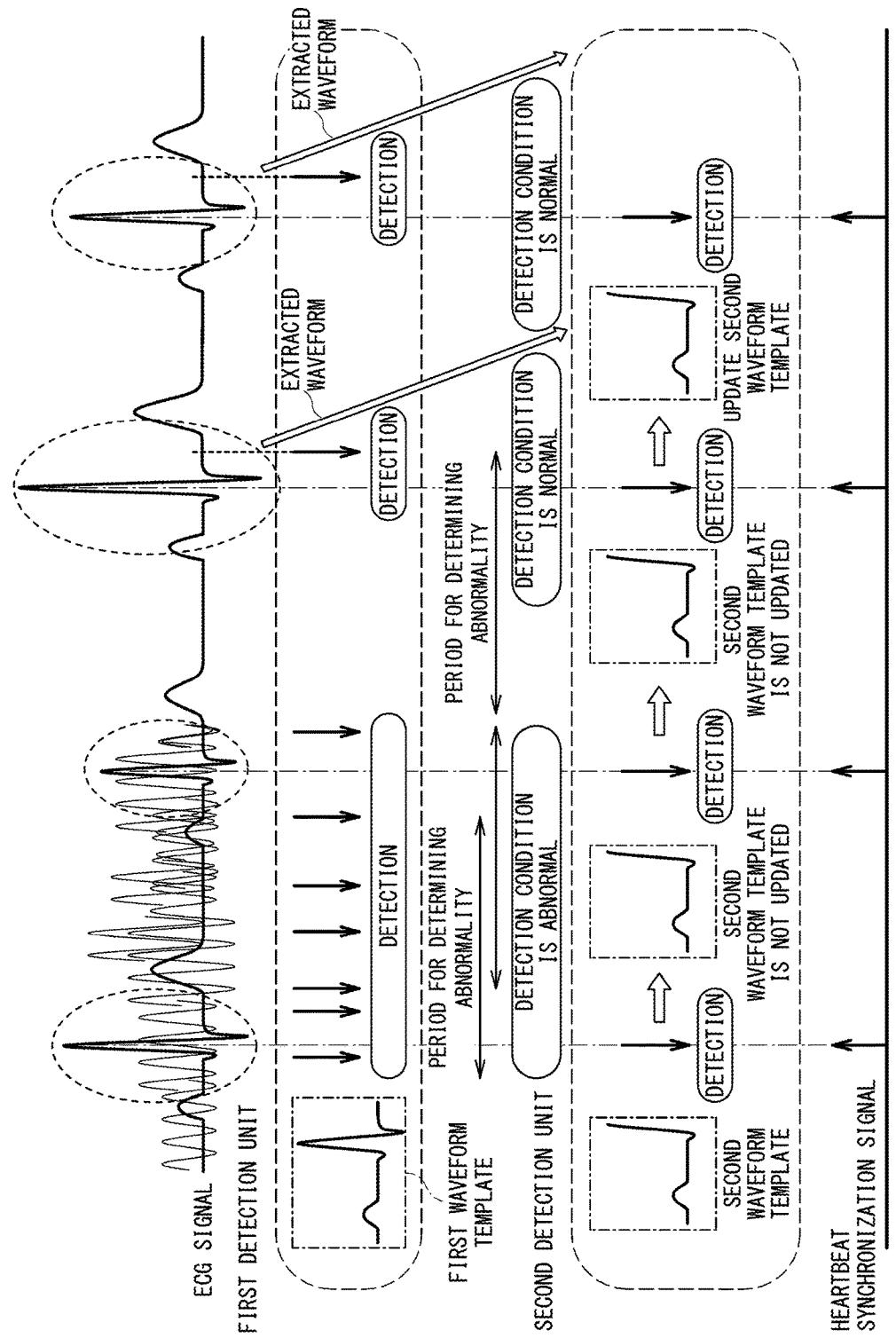
FIG. 12 is a diagram explaining operational conception of the ECG waveform detecting apparatus of the first modification of the first embodiment.

FIG. 12 is a diagram explaining operational concept of the ECG waveform detecting apparatus 1a of the first modification of the first embodiment. When the ECG synchronization imaging apparatus 200 is an MRI apparatus, the ECG synchronization imaging apparatus 200 applies RF pulses and gradient magnetic field pulses to an object. External disturbance and noise caused by application of these pulses are superimposed on ECG signals. The left side of the top part of FIG. 12 shows an example in which a disorder arises in the waveform of an ECG signal. In addition, the waveform of an ECG signal is sometimes disturbed also in the case of moving a bed on which a patient is loaded.

If the second waveform template is updated by using an ECG signal whose waveform is disturbed, the second detection unit 40 cannot normally perform detection in some cases. For the above reasons, the ECG waveform detecting apparatus 1a determines whether the waveform of ECG signals is disturbed or not, on the basis of the detection condition of the first detection unit 20. When the detection condition of the first detection unit 20 is abnormal, the ECG waveform detecting apparatus 1a stops update processing of the second waveform template.

For example, when the detection number of a waveform performed by the first detection unit 20 within a predetermined period for determining abnormality is larger than a predetermined reference number, the detection condition is determined to be abnormal. For example, when the predetermined period for determining abnormality is set to 1 second and the detection number within 1 second is 5 times or more, the detection condition is determined to be abnormal.

In addition to the above determination method, the detection condition may be determined on the basis of increase of the detection number. For example, the detection number within the predetermined period for determining abnormality is stored for a predetermined span. The detection condition may be determined to be abnormal, when the detection number within the current period for determining abnormality is increasing at a predetermined rate or more rapidly with respect to the average value of the detection number in the past periods for determining abnormality.

When the detection condition is determined to be abnormal as shown in the left part of FIG. 12, update processing of the second waveform template is stopped. On the other hand, when the detection condition is restored to a normal state as shown in the right part of FIG. 12, update processing of the second waveform template is resumed.

The second detection unit 40 continues detection of an R-wave by using the maintained second waveform template, even in the period during which the detection condition of the first detection unit 20 is determined to be abnormal. Even if the waveform of ECG signal is temporally disturbed, highly reliable detection is possible as shown in FIG. 9D as long as the similarity between the waveform of an ECG signal itself from which external disturbance is eliminated and the shape of the second waveform template immediately before the stop of the update processing.

(The Second Modification of the First Embodiment)

Figure 13:
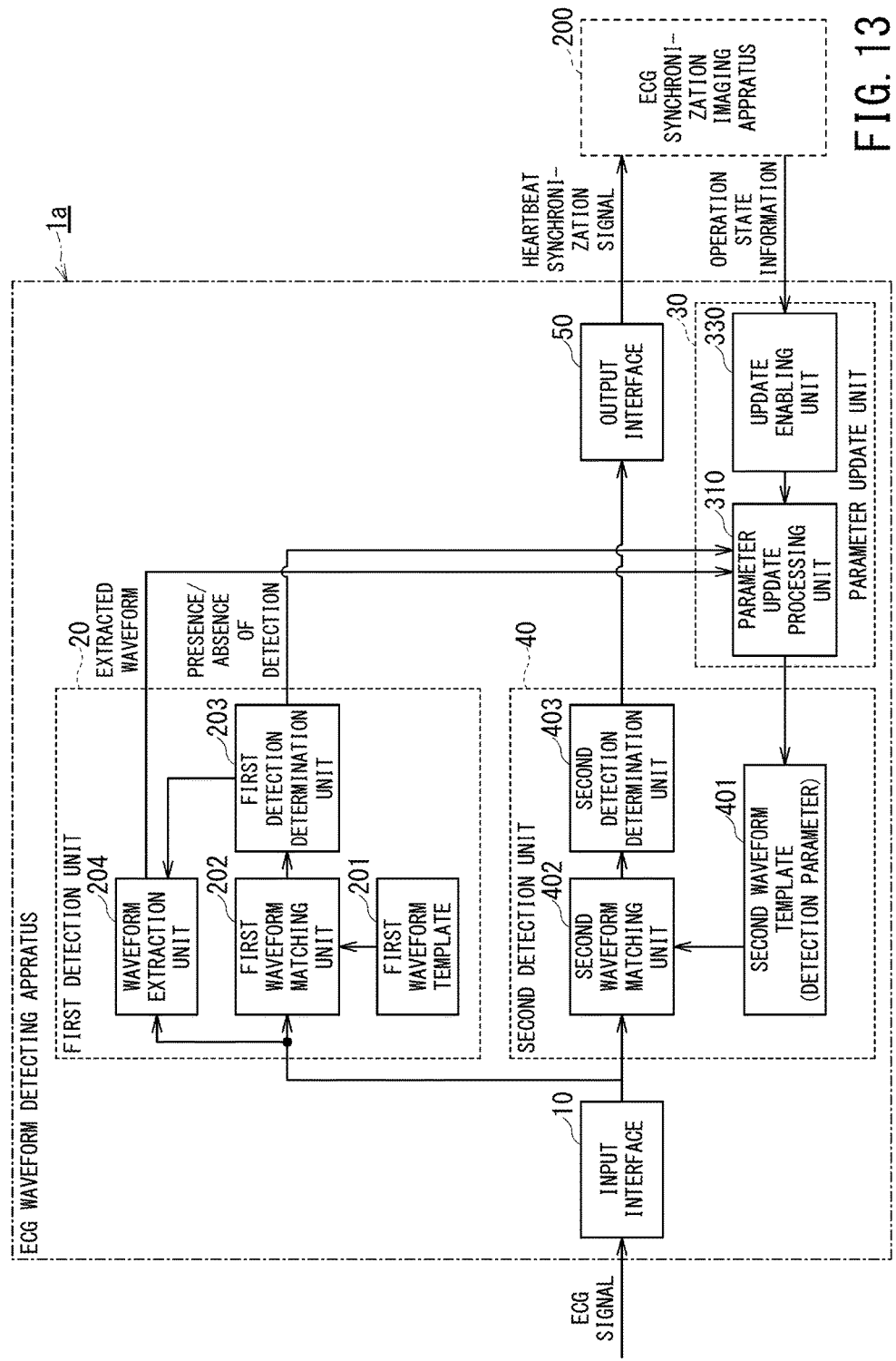
FIG. 13 is a block diagram showing an example of configuration of the ECG waveform detecting apparatus of the second modification of the first embodiment.

FIG. 13 is a block diagram showing an example of configuration of the ECG waveform detecting apparatus 1a according to the second modification of the first embodiment. The difference between this second modification and the first modification of the first embodiment lies in that the ECG waveform detecting apparatus 1a of the second modification includes an update enabling unit 330 instead of the abnormal-detection determination unit 320 of the parameter update unit 30.

The update enabling unit 330 acquires operation state information on the ECG synchronization imaging apparatus 200. The operation state information is, for example, information indicating that the ECG synchronization imaging apparatus 200 is currently applying an RF pulse and/or a gradient magnetic field pulse, information indicating that a bed is moving. The update enabling unit 330 determines whether the update processing of the second waveform template (the detection parameter of the second detection unit 40) is to be permitted or not, on the basis of the operation state information. When the ECG synchronization imaging apparatus 200 is an MRI apparatus, the waveform of ECG signals is likely to be perturbed during an application period of RF pulses and/or gradient magnetic field pulses. In addition, the waveform of ECG signals is sometimes perturbed while the bed loading a patient thereon is moving. The perturbation of the waveform of ECG signals during a moving period of the bed may be caused also when the ECG synchronization imaging apparatus 200 is a CT apparatus.

The update enabling unit 330 temporarily stops the update processing of the second waveform template in the period during which the ECG synchronization imaging apparatus 200 is applying an RF pulse and/or a gradient magnetic field pulse and in the period during which the ECG synchronization imaging apparatus 200 is moving the bed. In the period except the above two sorts of periods, the update enabling unit 330 permit the parameter update processing unit 310 to update the second waveform template by using an ECG signal.

For example, when the ECG synchronization imaging apparatus 200 is an MRI apparatus, the ECG synchronization imaging apparatus 200 sequentially performs plural protocols in one examination according to imaging conditions inputted by an operator in the imaging planning phase in some cases (for example, plural protocols for acquiring plural type of images such as T1 weighted images, T2 weighted images, and so on). In addition, though the ECG synchronization imaging apparatus 200 continuously performs the plural protocols, an interruption time is sometimes inserted between a protocol and its next protocol. The update enabling unit 330 receives information indicating start of protocols, information indicating that protocols are in progress, and information indicating stop of protocols, as the operation state information from the ECG synchronization imaging apparatus 200, for example. On the basis of the received operation state information, the update enabling unit 330 performs control such as updating the second waveform template in an interruption period between protocols and stopping the update processing while the protocols are in progress.

According to the second modification of the first embodiment, the second waveform template is prevented from being updated based on an ECG signal whose waveform is disturbed, by using simpler processing.

(The Second Embodiment)

Figure 14:
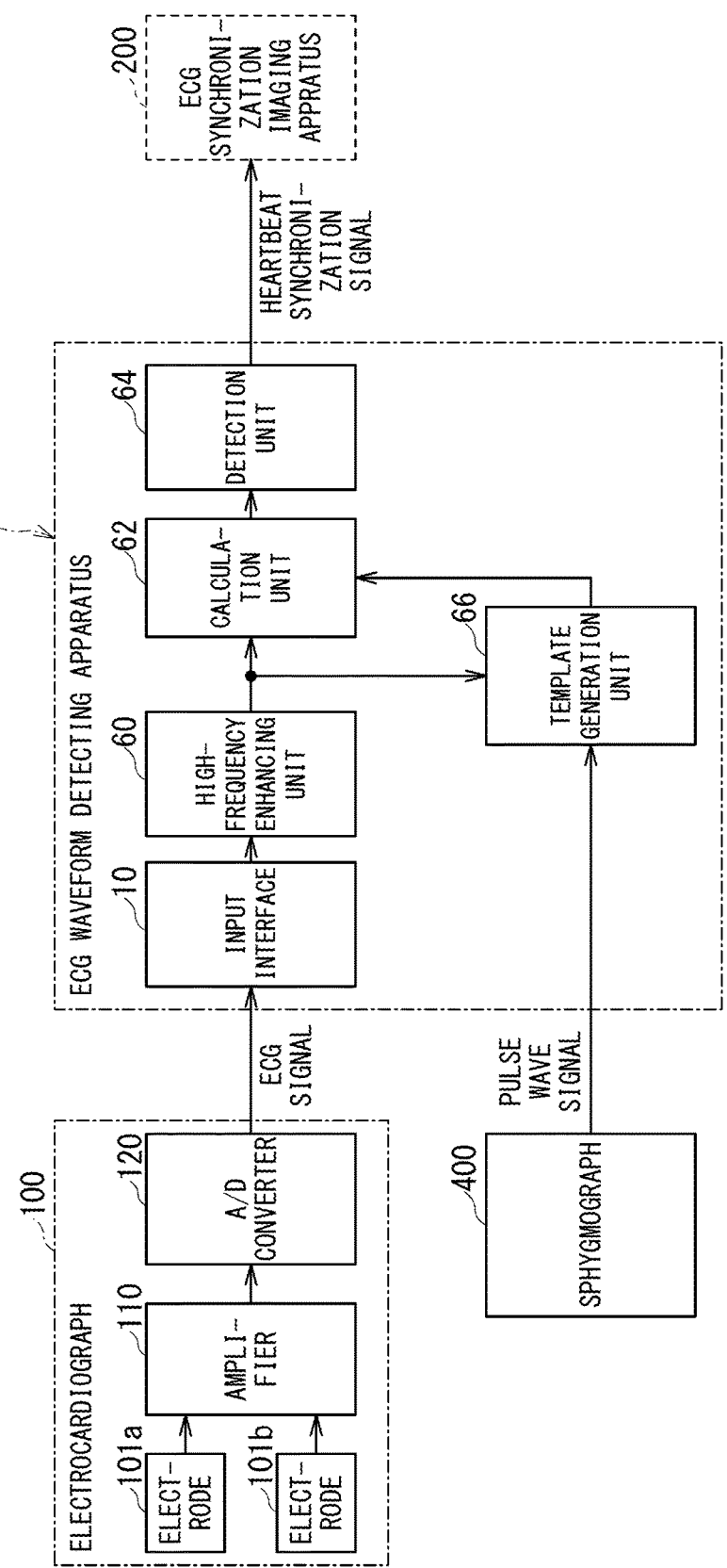
FIG. 14 is a block diagram showing an example of configuration of the ECG waveform detecting apparatus of the second embodiment.

FIG. 14 is a block diagram showing configuration of an ECG waveform detecting apparatus 1b of the second embodiment and configuration of an apparatus connected to the ECG waveform detecting apparatus 1b. The electrocardiograph 100 generates ECG signals and transmits the generated ECG signals to the ECG waveform detecting apparatus 1b. The sphygmograph 400 generates pulse wave signals and transmits the generated pulse wave signals to the ECG waveform detecting apparatus 1b. The ECG waveform detecting apparatus 1b generates heartbeat synchronization signals from the ECG signals and transmits the heartbeat synchronization signals to the ECG synchronization imaging apparatus 200.

The electrocardiograph 100 and the ECG synchronization imaging apparatus 200 are the same as the first embodiment, and duplicated explanation is omitted.

The ECG waveform detecting apparatus 1b includes the input interface 10, a high-frequency enhancing unit 60, a calculation unit 62, a detection unit 64, and a template generation unit 66.

The input interface 10 acquires ECG signals from the A/D converter 120. The high-frequency enhancing unit 60 performs high-frequency enhancement processing on ECG signals so as to generate ECG signals whose high-frequency component is emphasized (i.e. high-frequency enhanced ECG signals). The calculation unit 62 calculates an evaluation value by matching the high-frequency enhanced ECG signal with a high-frequency enhanced template. Here, the high-frequency enhanced template is a template corresponding to a waveform obtained by performing the high-frequency enhancement processing on a specific target waveform. In this example, the high-frequency enhanced template is a template corresponding to a waveform of an R-wave subjected to the high-frequency enhancement processing. Hereinafter, the high-frequency enhanced template is sometimes simply referred to as the template.

The template generation unit 66 generates the above high-frequency enhanced template on the basis of the high-frequency enhanced ECG signal generated by the high-frequency enhancing unit 60. The detection unit 64 detects R-waves on the basis of the evaluation value and generates heartbeat synchronization signals. In addition, the detection unit 64 transmits the generated heartbeat synchronization signals to the ECG synchronization imaging apparatus 200.

Each of the units of the ECG waveform detecting apparatus 1b may be configured of hardware such as ASIC, or an FPGA like the first embodiment, or each function of the units may be achieved by software processing. Alternatively or additionally, each function of the units may be achieved by combination of hardware and software processing. In the case of achieving them by software processing, the operation of each unit of the ECG waveform detecting apparatus 1b can be realized by causing the computer 300 illustrated in FIG. 3 to execute predetermined programs in the way similar to the first embodiment.

The ECG waveform detecting apparatus 1b of the second embodiment detects an R-wave by matching the high-frequency enhanced ECG signal with the high-frequency enhanced template. Hereinafter, the reason for this will be explained.

An R-wave, which is a target waveform in an ECG signal, has a waveform peculiar to each of objects. However, when it is observed within measurement target time, temporal variation between the respective R-waves is small. Thus, in order to improve a detection rate of R-waves, a peculiar waveform for each of the objects may be used as a template. Meanwhile, in the ECG signal, there exist waveforms similar to the waveform of R-waves, or there exist waveforms of external disturbance signals superimposed on the ECG signal. For example, depending on conditions such as a position of each electrode, a T-wave may show a waveform similar to that of an R-wave, and thus resulting in erroneously detecting the T-wave instead of the R-wave. In addition, an external disturbance signal similar to an R-wave may be often superimposed on the ECG signal due to electromagnetic induction inside an MRI apparatus. In such a case, there is a possibility that an external disturbance signal is erroneously detected as an R-wave.

When the difference in waveform between an R-wave and an external disturbance signal or a waveform except the detection target is small, it becomes difficult to stably detect R-waves. Thus, in order to further improve a detection rate of R-waves, it is desirable to make the difference between an R-wave and other waveforms except an R-wave as large as possible.

Figure 15:
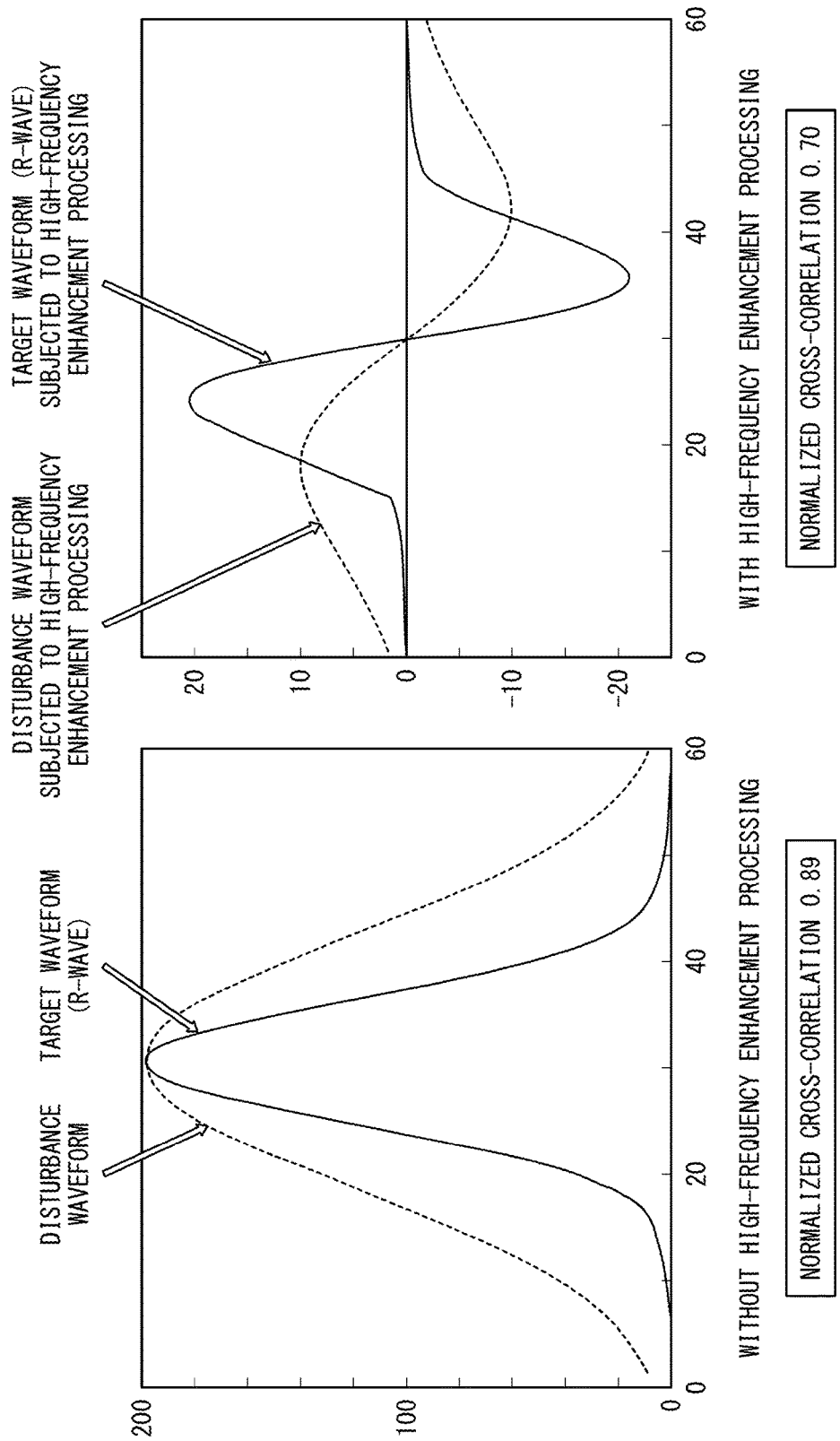
FIG. 15A is a diagram schematically illustrating a waveform of an R-wave (solid line) obtained without performing high-frequency enhancement processing and a waveform of an external disturbance signal (broken line) similar to an R-wave.
FIG. 15B is a diagram showing waveforms obtained by performing the high-frequency enhancement processing respectively on the R-wave and the external disturbance signal shown in FIG. 15A.

FIG. 15A is a diagram schematically illustrating a waveform of R-wave (solid line) obtained without performing high-frequency enhancement processing and a waveform of an external disturbance signal (broken line) similar to an R-wave.

The calculated value of the normalized cross-correlation between the R-wave and the external disturbance signal shown in FIG. 15A is 0.89. Although this value is smaller than the normalized cross-correlation value of 1.0 for a perfectly identical waveform, this is a rather large value close to 1.0.

Conventionally, inputted ECG signals are matched with a template corresponding to a waveform of an R-wave by using matching processing such as cross-correlation calculation. Then, an R-wave is detected by comparing a cross-correlation value obtained as the matched result with a predetermined threshold value. In this case, in order to avoid erroneous detection of the external disturbance signal shown in FIG. 15A, it is necessary to set the threshold value to a value larger than 0.89. However, when setting the threshold value to such a large value, it becomes difficult to stably detect R-waves if a waveform of an R-wave as the detection target is changed. On the other hand, when setting the threshold value to a small value for the purpose of stably detecting R-waves, frequency of erroneous detection of an external disturbance signal increases.

By contrast, the ECG waveform detecting apparatus 1b of the second embodiment performs the high-frequency enhancement processing prior to the matching processing. By the high-frequency enhancement processing, the target waveform subjected to the matching processing is converted into a waveform which is more sensitive to width and inclination of waveforms.

FIG. 15B is a diagram showing waveforms obtained by performing the high-frequency enhancement processing on the R-wave and the external disturbance signal shown in FIG. 15A. In each waveform subjected to the high-frequency enhancement processing, the positive peak position and the positive peak value respectively correspond to the position of the positive maximum inclination and the maximum value of the positive inclination in the waveform before the high-frequency enhancement processing. In addition, in each waveform subjected to the high-frequency enhancement processing, the negative peak position and the negative peak value respectively correspond to the position of the negative maximum inclination and the negative value of the positive inclination in the waveform before the high-frequency enhancement processing.

When the high-frequency enhancement processing is not performed, despite close resemblance in waveform between the R-wave and the external disturbance signal, both are different in width, rising inclination, and falling inclination of waveform from each other in many cases as shown in FIG. 15A. Therefore, in the waveforms subjected to the high-frequency enhancement processing (FIG. 15B), both or either of each position and each value of the positive and negative peaks are different between the R-wave and the external disturbance signal. In other words, the difference between the R-wave and the external disturbance signal is increased by performing the high-frequency enhancement processing. For example, though the normalized cross-correlation value between the R-wave and the external disturbance signal is 0.89 before the high-frequency enhancement processing, the normalized cross-correlation value is reduced to 0.70 after the high-frequency enhancement processing.

As the result, when the cross-correlation value between the template corresponding to the waveform of the R-wave subjected to the high-frequency enhancement processing and the ECG waveform subjected to the high-frequency enhancement processing is calculated and R-waves are detected by comparing the calculated cross-correlation value with the threshold value, the probability of correctly detecting an R-wave (correct detection rate) can be enhanced. In addition, the probability of erroneously detecting an external disturbance signal (incorrect detection rate) can be suppressed also in the case of an external disturbance signal whose waveform is similar to an R-wave.

Figure 16:
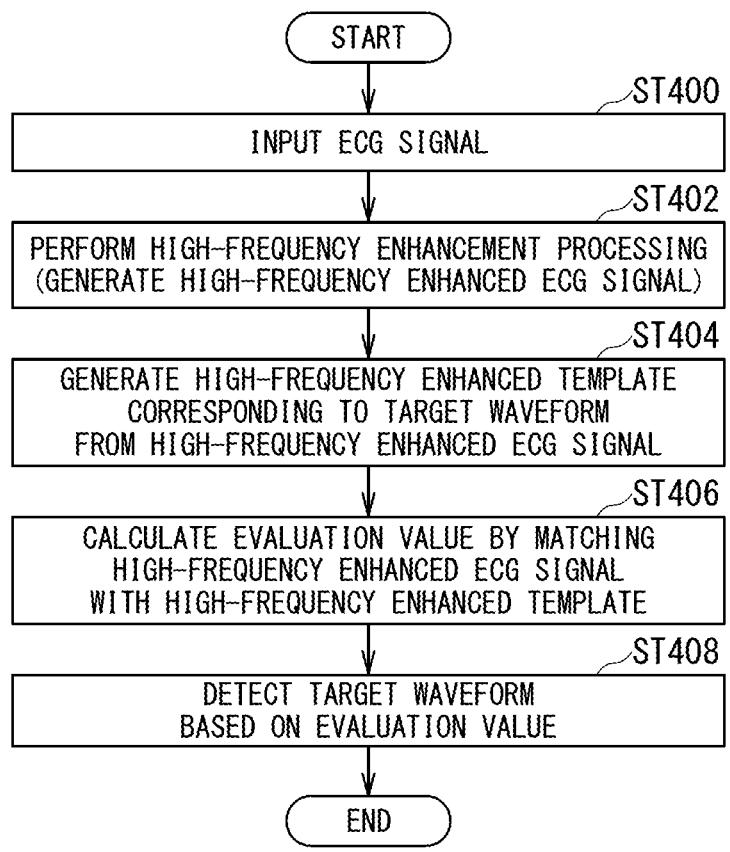
FIG. 16 is a flowchart showing an example of processing performed by the ECG waveform detecting apparatus of the second embodiment.

FIG. 16 is a flowchart showing an example of the outline of the processing performed by the ECG waveform detecting apparatus 1b. In the step ST400, the input interface 10 of the ECG waveform detecting apparatus 1b inputs an ECG signal as a time-series signal. An ECG signal is, for instance, a signal sampled at a constant interval (for example, a sampling interval of 1 millisecond).

Figure 17:
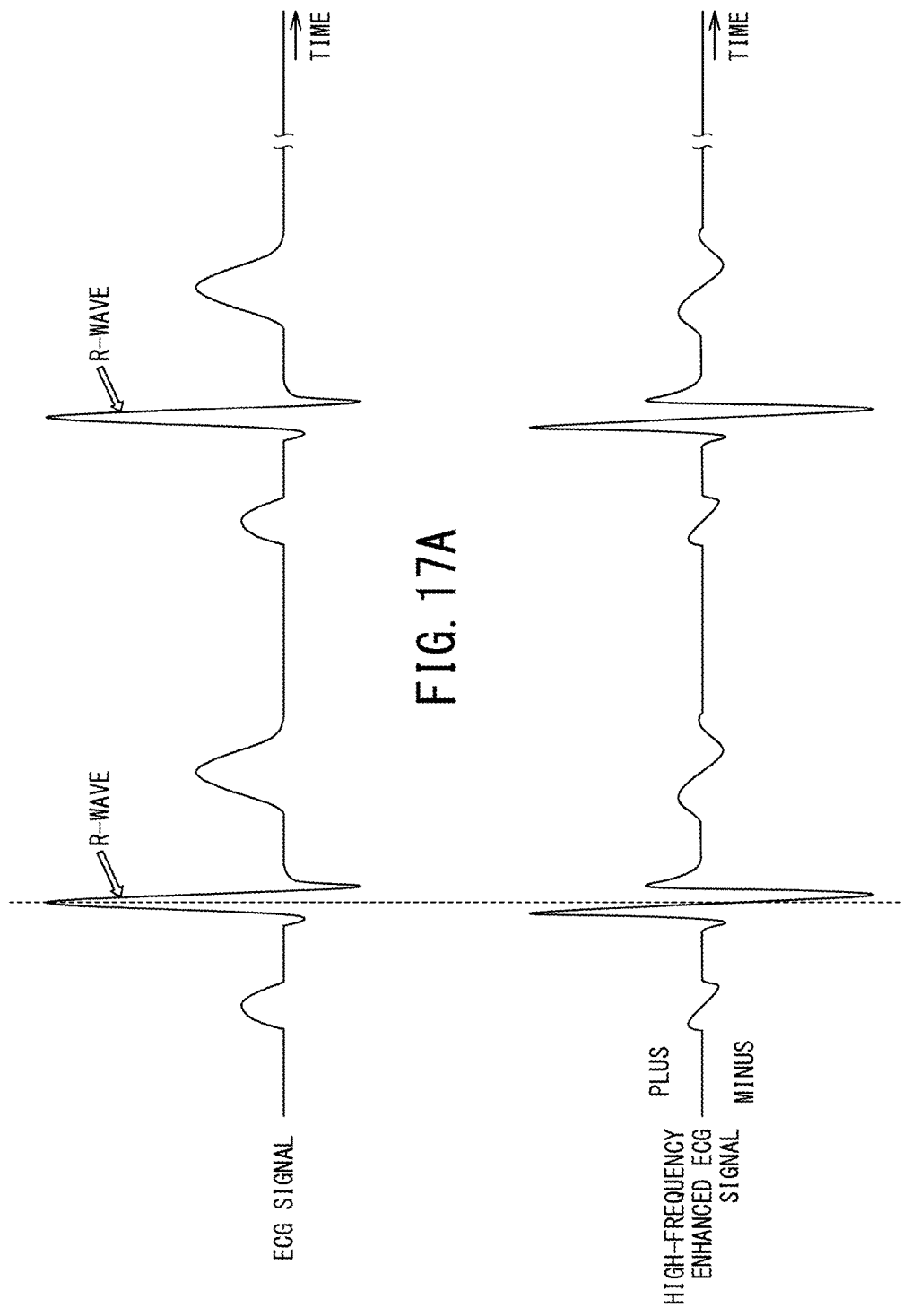
FIG. 17A is a diagram illustrating an example of an ECG waveform inputted to a high-frequency enhancing unit.
FIG. 17B is a diagram illustrating an example of a high-frequency enhanced ECG signal outputted from the high-frequency enhancing unit.

In the step ST402, the high-frequency enhancing unit 60 performs the high-frequency enhancement processing on the inputted ECG signal. The high-frequency enhancing unit 60 outputs the ECG signal whose high-frequency band is emphasized, i.e. the high-frequency enhanced ECG signals. FIG. 17A is a diagram illustrating an example of an ECG waveform inputted to the high-frequency enhancing unit 60. FIG. 17B is a diagram illustrating an example of the high-frequency enhanced ECG signal outputted from the high-frequency enhancing unit 60. The positive maximum peak and the negative maximum peak are generated at the position corresponding to an R-wave of the high-frequency enhanced ECG waveform. The positive peak is generated at the position of the maximum inclination in the rising part of an R-wave. In addition, the negative peak is generated at the position of the maximum inclination in the falling part of an R-wave. The zero-cross position of the positive maximum peak and the negative maximum peak corresponds to the peak position of an R-wave.

Figure 18:
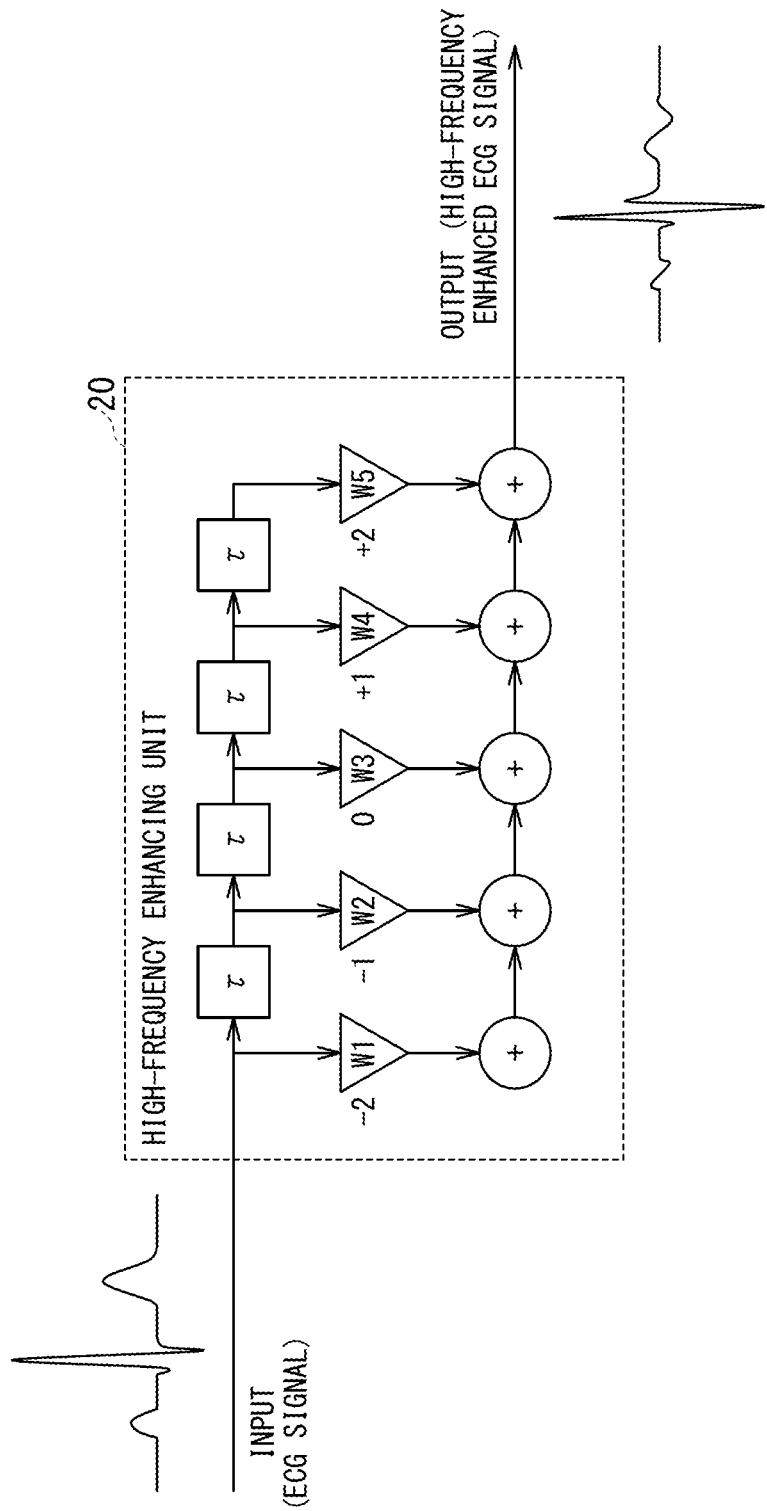
FIG. 18 is a diagram showing an example of configuration of an FIR filter of the high-frequency enhancing unit.

Although the high-frequency enhancement processing performed by the high-frequency enhancing unit 60 is not limited to a specific method, for example, differential processing achieved by an FIR (Finite Impulse Response) filter with plural taps may be used. FIG. 18 is a diagram showing an example of configuring the high-frequency enhancing unit 60 by using a five-tap FIR filter. In the FIR filter shown in FIG. 18, "τ" is a delay element, W1 to W5 are filter coefficients, and "+" is an addition element.

When the FIR filter shown in FIG. 18 is configured as a filter for the high-frequency enhancement processing (differential processing), the coefficients of a 5-tap filter (W1, W2, W3, W4, W5) are, for example, set as follows.

(W1, W2, W3, W4, W5)=(−1, −2, 0, 2, 1)

The number of taps of the FIR filter may be another number except five. As another example, the coefficients of a 4-tap filter (W1, W2, W3, W4) are, for instance, set as follows.

(W1, W2, W3, W4)=(−1, −2, 2, 1)

The coefficients of a 3-tap filter (W1, W2, W3) are, for example, set as follows.

(W1, W2, W3)=(−1, 0, 1)

In addition, the coefficients of a 2-tap filter (W1, W2) are, for example, set as follows.

(W1, W2)=(−1, 1)

The coefficients of the FIR filter may be determined by machine learning. As shown in FIG. 15A and FIG. 15B, in order to reduce erroneous detection of an external disturbance signal, it is preferable that the normalized cross-relation between an the R-wave as a detection target signal and the external disturbance signal is as small as possible. Accordingly, waveform data of R-waves and waveform data of external disturbance signals are preliminarily prepared as learning data, and the filter coefficients are calculated for an FIR filter, whose tap number is preliminarily determined, by the machine learning so as to make the average normalized cross-correlation small. Then, by using the filter coefficients calculated in the above manner for the FIR filter, the FIR filter configured to perform the high-frequency enhancement processing is realized.

Returning to FIG. 16, in the step ST404, the template generation unit 66 generates the template corresponding to an R-wave as a detection target signal, i.e. the high-frequency enhanced template, from the high-frequency enhanced ECG signals generated by the high-frequency enhancing unit 60.

Figure 19:
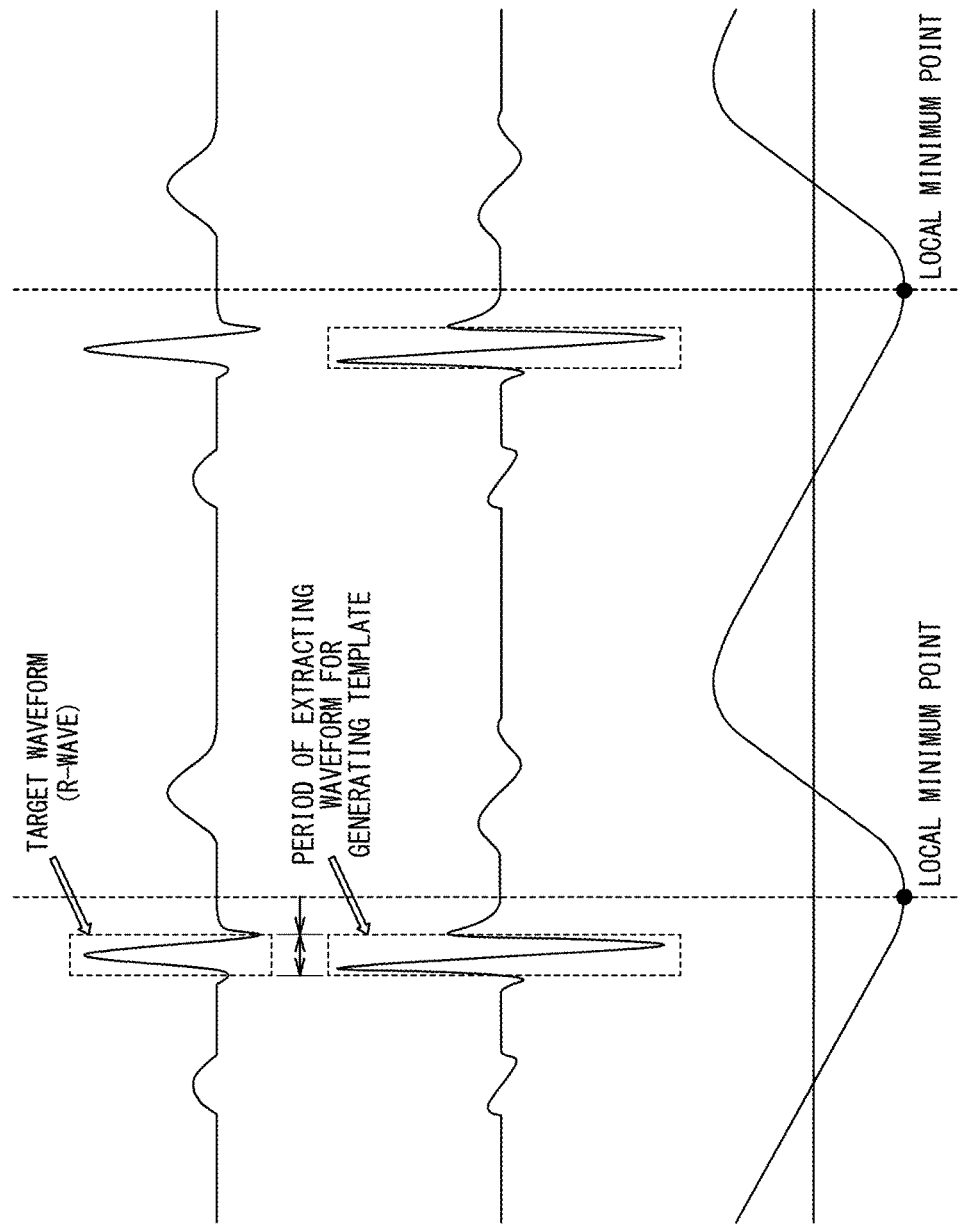
FIG. 19A to FIG. 19C are diagrams explaining an example of a method of generating a high-frequency enhanced template.

FIG. 19A to FIG. 19C are diagrams explaining an example of a method of generating the high-frequency enhanced template. The template generation unit 66 generates the high-frequency enhanced template by the extracting the high-frequency enhanced ECG signal in the period corresponding to an R-wave, as shown in FIG. 19A and FIG. 19B. The template generation unit 66 determines the extraction position of the high-frequency enhanced template, on the basis of the pulse wave signal inputted from the sphygmograph 400.

The pulse wave signal is a signal which the sphygmograph 400 obtains by measuring motion of peripheral blood vessels. As shown in FIG. 19C, in the pulse wave signal, each local minimum point generally appears at the position slightly later than each R-wave. Thus, the high-frequency enhanced template corresponding to an R-wave can be generated by cutting off (extracting) the high-frequency enhanced ECG signal positioned slightly earlier than a local minimum point.

However, the time width from an R-wave to a local minimum point of the pulse wave signal is different from individual to individual. Then, the searching range of R-waves is set to a period earlier than a local minimum point of the pulse wave signal, and the position within the searching range at which the absolute value of intensity of the ECG signal is the maximum is determined as the peak position of the R-wave. Afterward, the high-frequency enhanced template corresponding to an R-wave may be generated by extracting the high-frequency enhanced ECG signal corresponding to a predetermined time width whose center is the determined peak position of the R-wave. Incidentally, the time width of the extracted high-frequency enhanced template can be preliminarily determined on the basis of estimated time width of the R-wave.

The high-frequency enhanced template may be generated by using external signals except the pulse wave signal. For example, the searching range of an R-wave may be set by detecting cardiac sound with the use of a phonocardiograph and using this detection result.

The template generation unit 66 may update the high-frequency enhanced template on the basis of the latest high-frequency enhanced ECG signal inputted as a time-series signal. For example, the high-frequency enhanced template may be generated each time an R-wave arrives, and the past high-frequency enhanced template may be replaced with the latest high-frequency enhanced template. Alternatively, the update interval of the high-frequency enhanced template may be set to a longer period covering plural R-waves, and the past high-frequency enhanced template may be replaced with the latest high-frequency enhanced template at every update interval. Alternatively, the high-frequency enhanced template may be generated by calculating the simple moving average or weighted moving average of plural immediate high-frequency enhanced ECG signals extracted each time an R-wave arrives.

Figure 20:
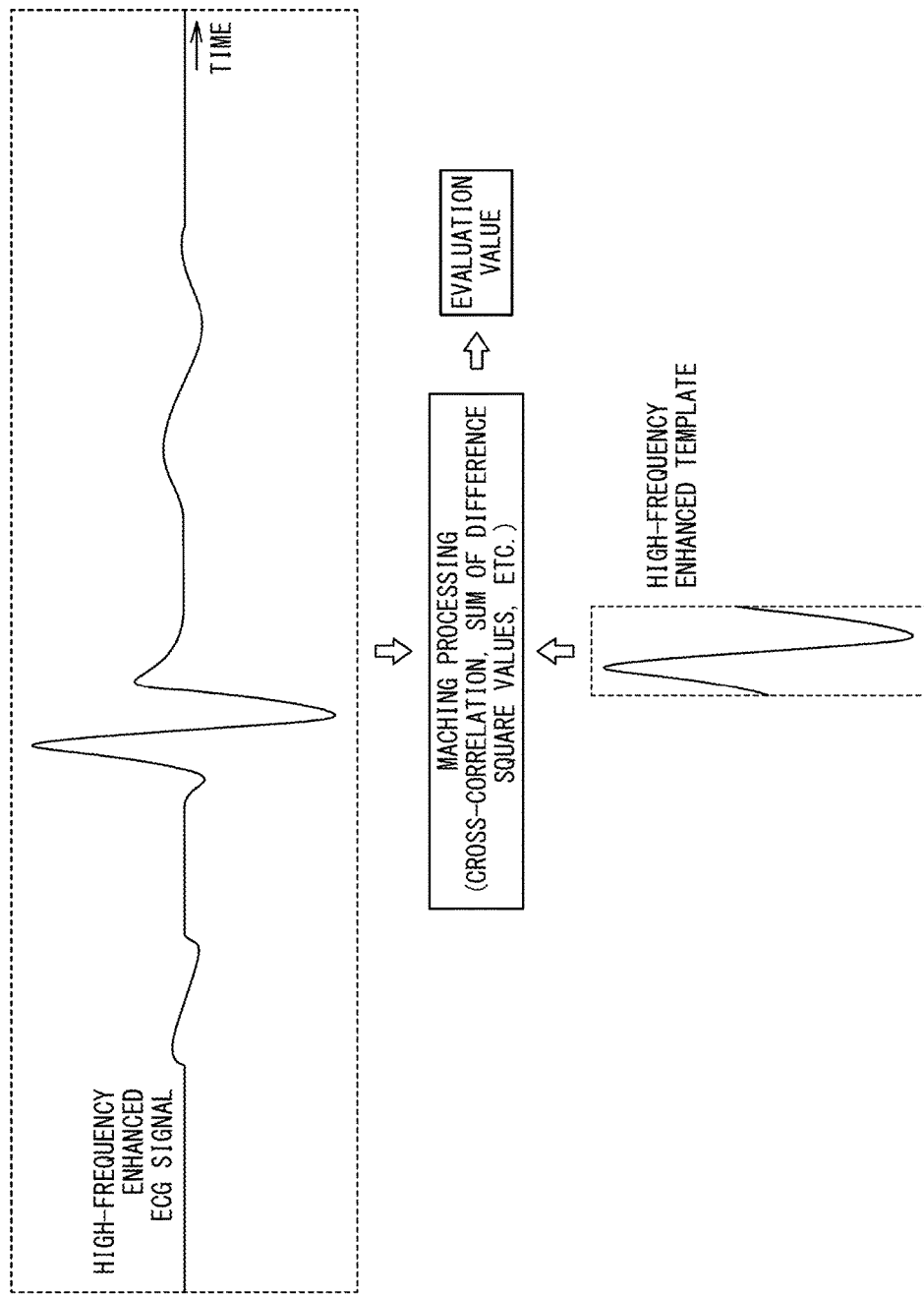
FIG. 20 is a diagram showing concept of matching processing between the high-frequency enhanced ECG signal and the high-frequency enhanced template.

After the high-frequency enhanced template is generated in the above manner, in the next step ST406, the calculation unit 62 calculates the evaluation value by matching the high-frequency enhanced ECG signal with the high-frequency enhanced template. FIG. 20 is a diagram showing concept of the matching processing between the high-frequency enhanced ECG signal and the high-frequency enhanced template performed by the calculation unit 62.

Hereinafter, some examples of the matching processing performed by the calculation unit 62 will be explained. In the following explanation, T(i) indicates the high-frequency enhanced template, S(i) indicates the high-frequency enhanced ECG signal, and E indicates the evaluation value. In addition, N indicates the length of the high-frequency enhanced template and i indicates an index.

In the first example of the matching processing, a Matched Filter is used. In other words, the cross-correlation between the high-frequency enhanced template T(i) and the high-frequency enhanced ECG signal S(i) is calculated and the cross-correlation value is defined as the evaluation value E. In this case, the more the high-frequency enhanced template T(i) and the high-frequency enhanced ECG signal S(i) resemble each other in shape, the larger the evaluation value E becomes. In addition, the stronger the strength of the high-frequency enhanced ECG signal S(i) is, the larger the evaluation value E becomes. The evaluation value E is given by the formula below.

$$E = \sum_{i=0}^{N-1} T(i) \cdot S(i)$$

In the second example of the matching processing, the normalized cross-correlation between the high-frequency enhanced template T(i) and the high-frequency enhanced ECG signal S(i) is calculated, and the normalized cross-correlation value is defined as the evaluation value E. The evaluation value E is normalized by intensity of the high-frequency enhanced template T(i) and the high-frequency enhanced ECG signal S(i). In this case, the more the high-frequency enhanced template T(i) and the high-frequency enhanced ECG signal S(i) resemble each other in shape, the larger the evaluation value E becomes. The evaluation value E is given by the formula below.

$$E = \frac{\sum_{i=0}^{N-1} T(i) \cdot S(i)}{\sqrt{\sum_{i=0}^{N-1} T(i)^2} \sqrt{\sum_{i=0}^{N-1} S(i)^2}}$$

Instead of the above formula, a zero-mean normalized cross-correlation obtained by subtracting the average of T(i) from each T(i) and subtracting the average of S(i) from each S(i) may be used.

In the third example of the matching processing, a total sum of the difference square values or its square root is used as the evaluation value E. In these cases, the more the high-frequency enhanced template T(i) and the high-frequency enhanced ECG signal S(i) resemble each other in shape, the smaller the evaluation value E becomes. In the case of the total sum of the difference square values, the evaluation value E is given by the formula below.

$$E = \sum_{i=0}^{N-1} (T(i) \cdot S(i))^2$$

In addition, in the case of the square root of the total sum of the difference square values, the evaluation value E is given by the formula below.

$$E = \left( \sum_{i=0}^{N-1} (T(i) \cdot S(i))^2 \right)^{\frac{1}{2}}$$

In the fourth example of the matching processing, a total sum of difference absolute values, or more generally, the (1/p)-th power of the total sum of L−p norms of difference values (p>0) is used. The total sum of the difference absolute values corresponds to p=1. If p<2 in L−p norms, an effect of making the processing robust by reducing influence of an outlier is obtained even if an outlier due to a measurement error partly exist in the high-frequency enhanced ECG signal S(i) or the high-frequency enhanced template T(i). The formula using the total sum of the difference square values and the formula using the (1/p)-th power of the total sum of L−p norms of difference values are respectively given as follows. In both cases, the more the high-frequency enhanced template T(i) and the high-frequency enhanced ECG signal S(i) resemble each other in shape, the smaller the evaluation value E becomes.

$$E = \sum_{i=0}^{N-1} |T(i) \cdot S(i)|$$

$$E = \left( \sum_{i=0}^{N-1} |T(i) \cdot S(i)|^p \right)^{\frac{1}{p}}$$

Incidentally, 1/p power operation may be omitted as follows, because it does not influence on magnitude relation.

$$E = \sum_{i=0}^{N-1} |T(i) \cdot S(i)|^p$$

In the fifth example of the matching processing, an error function is used for calculating the evaluation value E. An error function is a function which returns a value smaller than the square of an input value as a function value in a case of a large input value. By using the error function, the effect of making the processing robust, in other words, reduction of influence of an outlier can be obtained. When a value of an error function of x is indicated as R(x), the evaluation value E can be calculated by the following formula with the use of the error function R(x). Also in this case, the more the high-frequency enhanced template T(i) and the high-frequency enhanced ECG signal S(i) resemble each other in shape, the smaller the evaluation value E becomes.

$$E = \sum_{i=0}^{N-1} R(T(i) \cdot S(i))$$

Three examples of error functions R(x) are shown as follows. Incidentally, the aspect of the error function is not limited to the following aspects. The parameter p of the error function may be determined beforehand by performing a preliminary experiment so as to obtain a satisfactory result.

$$R(x) \begin{cases} x^2 & -p < x < p \\ p^2 & \text{otherwise} \end{cases}$$

$$R(x) = \frac{x^2}{x^2 + p^2}$$

$$R(x) = \begin{cases} -2px - p^2 & x \le -p \\ x^2 & -p < x < p \\ 2px - p^2 & \text{otherwise} \end{cases}$$

After the evaluation value is calculated in the above manner, in the step ST408, the detection unit 64 detects an R-wave on the basis of the evaluation value and outputs a heartbeat synchronization signal to the ECG synchronization imaging apparatus 200.

FIG. 21A and FIG. 21B are diagrams explaining the concept of the operation of the detection unit 64. As mentioned above, in the first and second examples of the matching processing, the evaluation value is calculated as cross-correlation or normalized cross-correlation. In these cases, as shown in FIG. 21A, the more the high-frequency enhanced ECG signal and the high-frequency enhanced template resemble each other in shape, the larger the evaluation value becomes.

On the other hand, in the third to fifth examples of the matching processing, the evaluation value is calculated on the basis of differences. In these cases, as shown in FIG. 21B, the more the high-frequency enhanced ECG signal and the high-frequency enhanced template resemble each other in shape, the smaller the evaluation value becomes.

In both cases of FIG. 21A and FIG. 21B, the threshold value is determined and then the position at which the evaluation value exceeds the threshold value or the position at which the evaluation value falls below the threshold value can be determined as the detection position of an R-wave. Although the threshold value may be a fixed value, it can be adaptively changed. For example, in the cases of the third to fifth examples of the matching processing (the case of FIG. 21B), the minimum value and the median value of the evaluation values in a predetermined period immediately before detection are obtained, and the weighted sum of the minimum value and the median value obtained by using separately determined weighting coefficients may be determined as the threshold value.

The detection processing by the detection unit 64 is not limited to the methods of using a threshold value. For example, a local minimum point of evaluation values are calculated and the position of the local minimum point may be determined as the detection position of an R-wave.

Figure 22A:
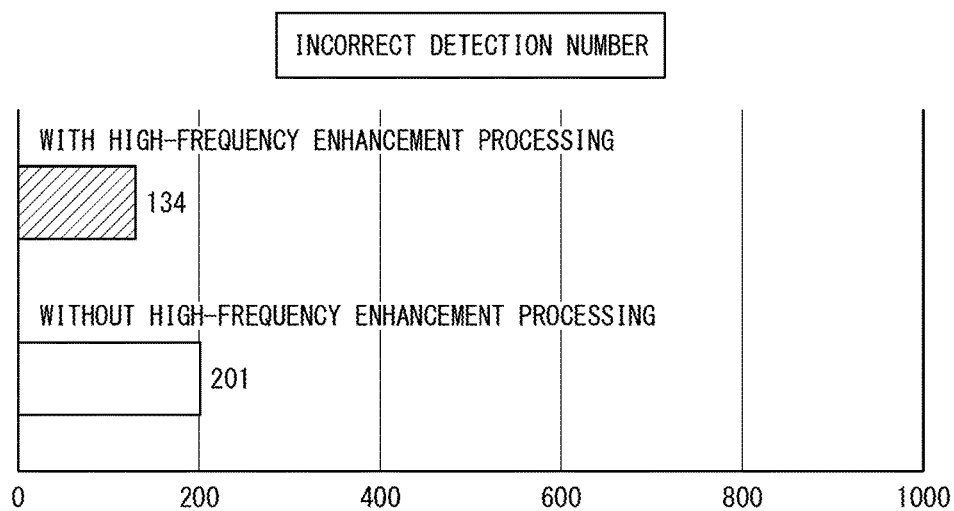
FIG. 22A and FIG. 22B are diagrams showing an example of an evaluation result for confirming the effectiveness of the ECG waveform detecting apparatus of the second embodiment.
Figure 22B:
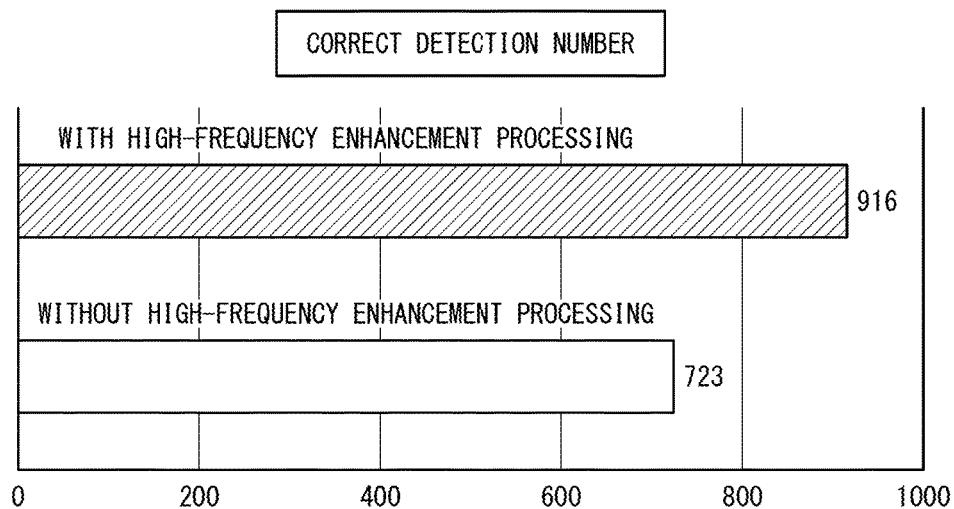

Incidentally, regardless of whether the threshold value is used or not, a false detection of a waveform similar to an R-wave may be prevented by excluding a predetermined period in an R-R interval from a period for detecting the R-wave, after the R-wave has been once detected. FIG. 22A and FIG. 22B are diagrams showing an example of an evaluation result for confirming the effectiveness of the above-mentioned ECG waveform detecting apparatus 1b. ECG signals disturbed by gradient magnetic fields of an MRI apparatus were acquired and R-waves were detected from these ECG signals. In the acquired ECG signals, 1108R-waves were included. The number of correctly detecting an R-wave (correct detection number) and the number of erroneously detecting something other than an R-wave as an R-wave (incorrect detection number) are compared between the case without using the high-frequency enhancement processing and the case where the high-frequency enhancement processing is performed.

As shown in FIG. 22A, the incorrect detection number is 201 in the case without using the high-frequency enhancement processing, but it was reduced to 134 in the case where the high-frequency enhancement processing is performed. On the other hand, as shown in FIG. 22B, the correct detection number is 723 in the case without using the high-frequency enhancement processing, but it was increased to 916 in the case where the high-frequency enhancement processing is performed. As just described, it has been confirmed that the incorrect detection number is reduced and the correct detection number is increased in the ECG waveform detecting apparatus 1b using the high-frequency enhancement processing.

(The First Modification of the Second Embodiment)

Figure 23:
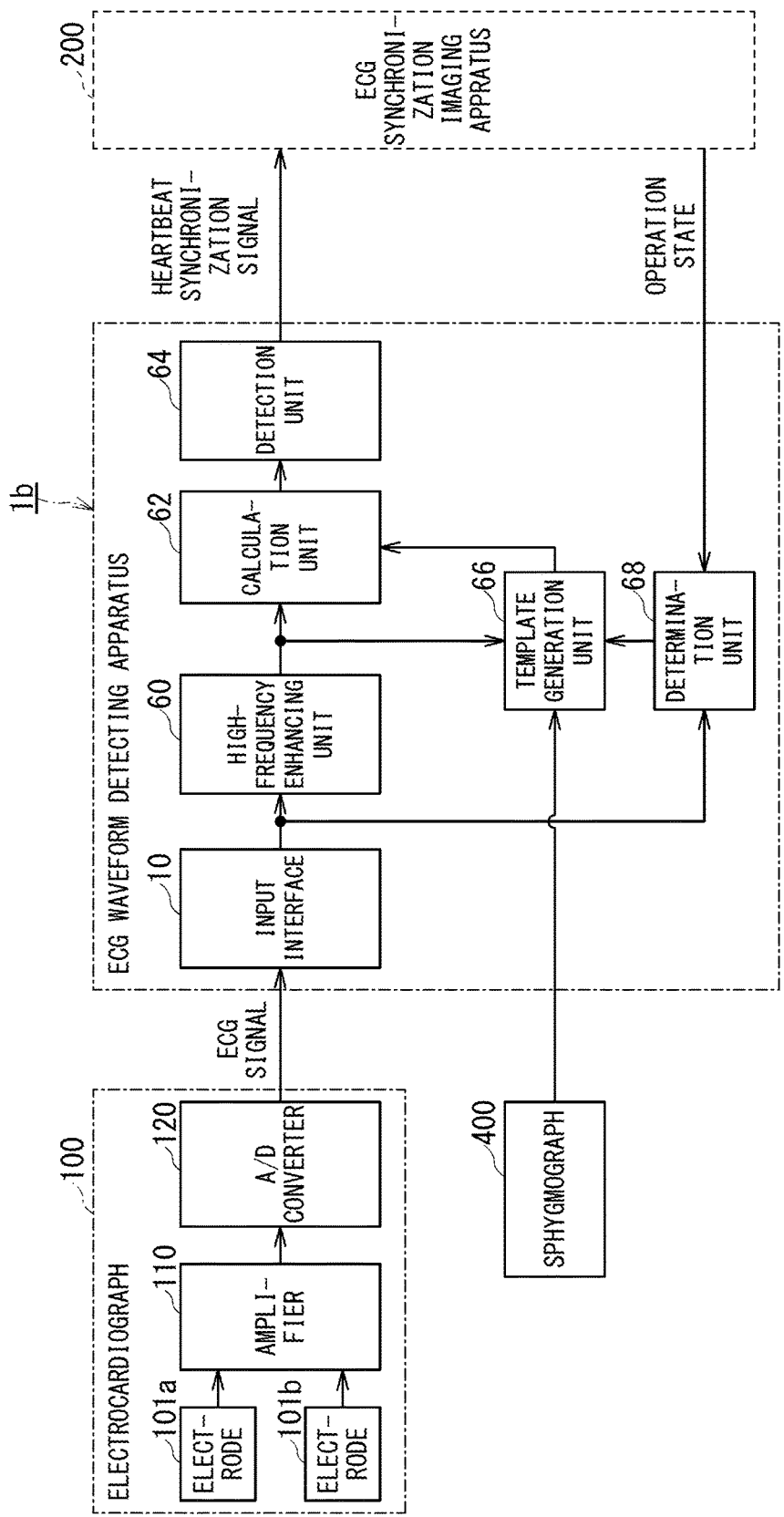
FIG. 23 is a block diagram showing an example of configuration of the ECG waveform detecting apparatus of the first modification of the second embodiment.

FIG. 23 is a block diagram showing an example of configuration of the ECG waveform detecting apparatus 1b of the first modification of the second embodiment. The difference between this first modification and the ECG waveform detecting apparatus 1b (FIG. 14) of the second embodiment lies in that first modification further includes a determination unit 68.

The determination unit 68 determines whether an external disturbance signal is superimposed on an ECG signal outputted from the electrocardiograph 100 or not. Then, the determination unit 68 outputs the determination result to the template generation unit 66. In each period during which an external disturbance signal is superimposed on an ECG signal according to the determination result of the determination unit 68, the template generation unit 66 temporarily stops the processing of generating or updating the high-frequency enhanced template. By contrast, only in each period during which an external disturbance signal is not superimposed on an ECG signal according to the determination result of the determination unit 68, the template generation unit 66 performs the processing of generating or updating the high-frequency enhanced template. As a result, generation of a high-frequency enhanced template whose shape is disturbed due to an external disturbance signal can be prevented.

Whether an external disturbance signal is superimposed on an ECG signal or not can be determined by monitoring a waveform of the ECG signal outputted from the input interface 10, for example. For instance, it may be determined on the basis of the number of detections exceeding a predetermined threshold value within a predetermined determination period.

In addition, whether an external disturbance signal is superimposed on the ECG signal or not can be determined on the basis of the operating state of the ECG synchronization imaging apparatus 200 by monitoring the operating state of the ECG synchronization imaging apparatus 200, instead of monitoring the ECG signal or in parallel with monitoring the ECG signal.

When the ECG synchronization imaging apparatus 200 is an MRI apparatus, the possibility that the waveform of the ECG signal is disturbed is high in a period during which RF pulses and gradient magnetic field pulses are applied. In addition, the waveform of the ECG signal is may be disturbed in a period during which a bed with a patient is moved. Disturbance due to the movement of the bed may occur also when the ECG synchronization imaging apparatus 200 is a CT apparatus.

The determination unit 68 determines that an external disturbance signal is superimposed on an ECG signal in each period at which the ECG synchronization imaging apparatus 200 applies an RF pulse and/or a gradient magnetic field pulse and in each period it moves the bed. By contrast, the determination unit 68 determines that an external disturbance signal is not superimposed on an ECG signal in each period during which the ECG synchronization imaging apparatus 200 does not perform application of an RF pulse and/or a gradient magnetic field or movement of the bed. Then, the template generation unit 66 performs the processing of generating or updating the high-frequency enhanced template in each period during which an external disturbance signal is not superimposed on an ECG signal according to the determination result.

For example, when the ECG synchronization imaging apparatus 200 is an MRI apparatus, the ECG synchronization imaging apparatus 200 sequentially performs plural protocols in one examination according to imaging conditions inputted by an operator in the imaging planning phase in some cases (for example, plural protocols for acquiring plural type of images such as T1 weighted images, T2 weighted images, and so on). In addition, though the ECG synchronization imaging apparatus 200 continuously performs the plural protocols, an interruption time is sometimes inserted between a protocol and its next protocol. The determination unit 68 receives information indicating start of protocols, information indicating that protocols are in progress, and information indicating stop of protocols, as the operation state information from the ECG synchronization imaging apparatus 200, for example. On the basis of the received operation state information, the determination unit 68 determines that an external disturbance signal is not superimposed on an ECG signal in each interruption time between protocols, and determines that an external disturbance signal is superimposed on an ECG signal in each period during which protocols are in progress.

(The Second Modification of the Second Embodiment)

Figure 24:
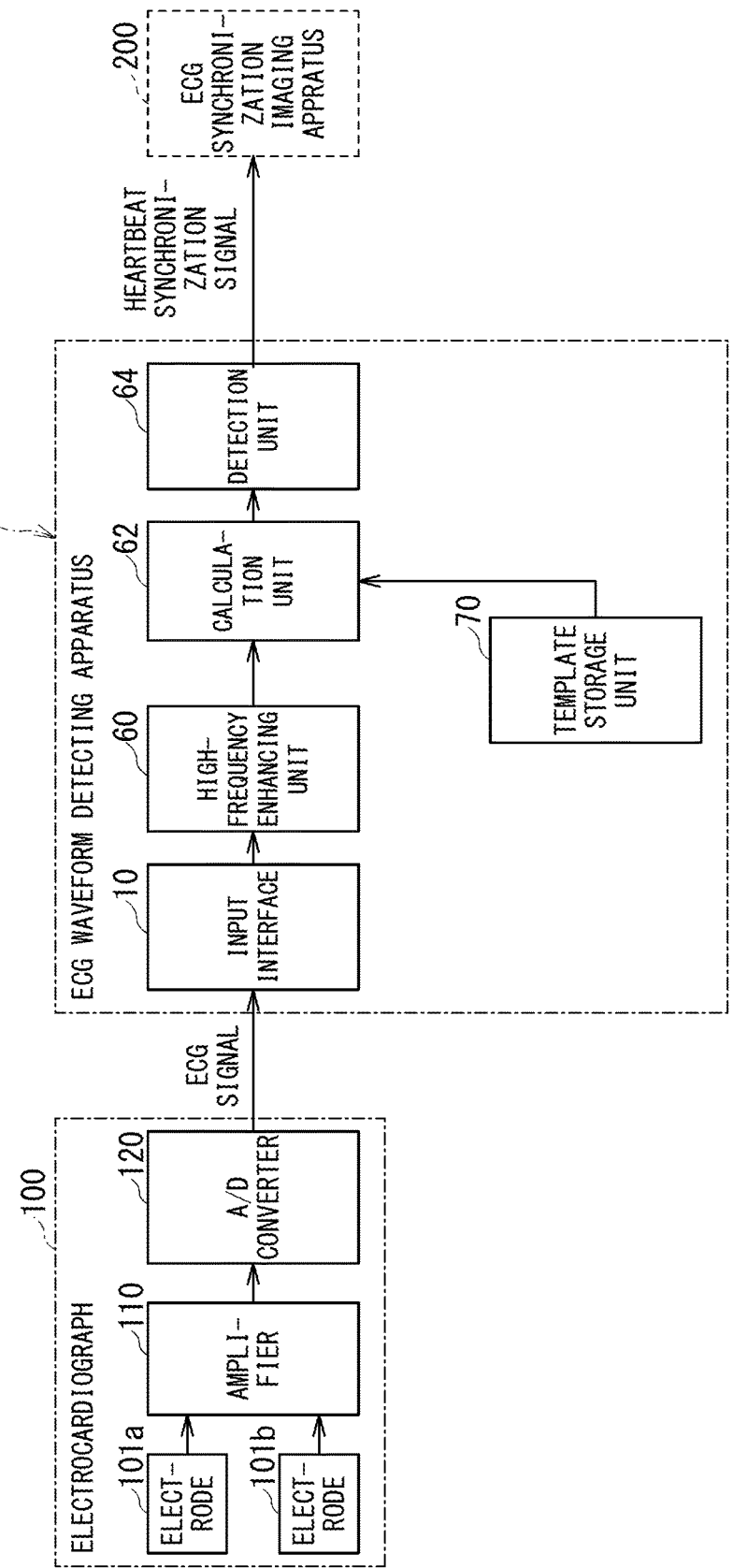
FIG. 24 is a block diagram showing an example of configuration of the ECG waveform detecting apparatus of the second modification of the second embodiment.

FIG. 24 is a block diagram showing an example of configuration of the ECG waveform detecting apparatus 1b of the second modification of the second embodiment. The difference between this second modification and the ECG waveform detecting apparatus 1b (FIG. 14) of the second embodiment lies in that the second modification includes a template storage unit 70 instead of the template generation unit 66.

In the second embodiment and its first modification, apart of the high-frequency enhanced ECG signal outputted from the high-frequency enhancing unit 60 on a real-time basis is extracted, and thereby the high-frequency enhanced template is generated or updated. By contrast, the ECG waveform detecting apparatus 1b of the second modification of the second embodiment preliminarily generates the high-frequency enhanced template prior to imaging of an object, and stores the high-frequency enhanced template in the template storage unit 70. Thus, the high-frequency enhanced template, which is not influenced by an external disturbance signal caused by application of an RF pulse and/or a gradient magnetic field pulse, can be provided to the calculation unit 62, even if the ECG synchronization imaging apparatus 200 is an MRI apparatus as an example. This is because the high-frequency enhanced template is generated before imaging.

(The Third Modification of the Second Embodiment)

In the above-mentioned second embodiment, and its first and second modifications, ECG signals outputted from the electrocardiograph 100 to the ECG waveform detecting apparatus 1b is one-dimensional (the number of ECG signal is one at any timing).

On the other hand, for example, a twelve-lead electrocardiograph outputs twelve (twelve-dimensional) ECG signals such as I, II, III, aVR, aVL, aVF, and V1 to V6. In addition, for example, in the case of an electrocardiograph of four terminals used for ECG synchronization, two or three ECG signals are outputted (two-dimensional or three-dimensional). Moreover, for instance, a vectorcardiogram uses three (three-dimensional) ECG signals generated from plural electrode signals (these three signals are referred to as X, Y, and Z).

Figure 25:
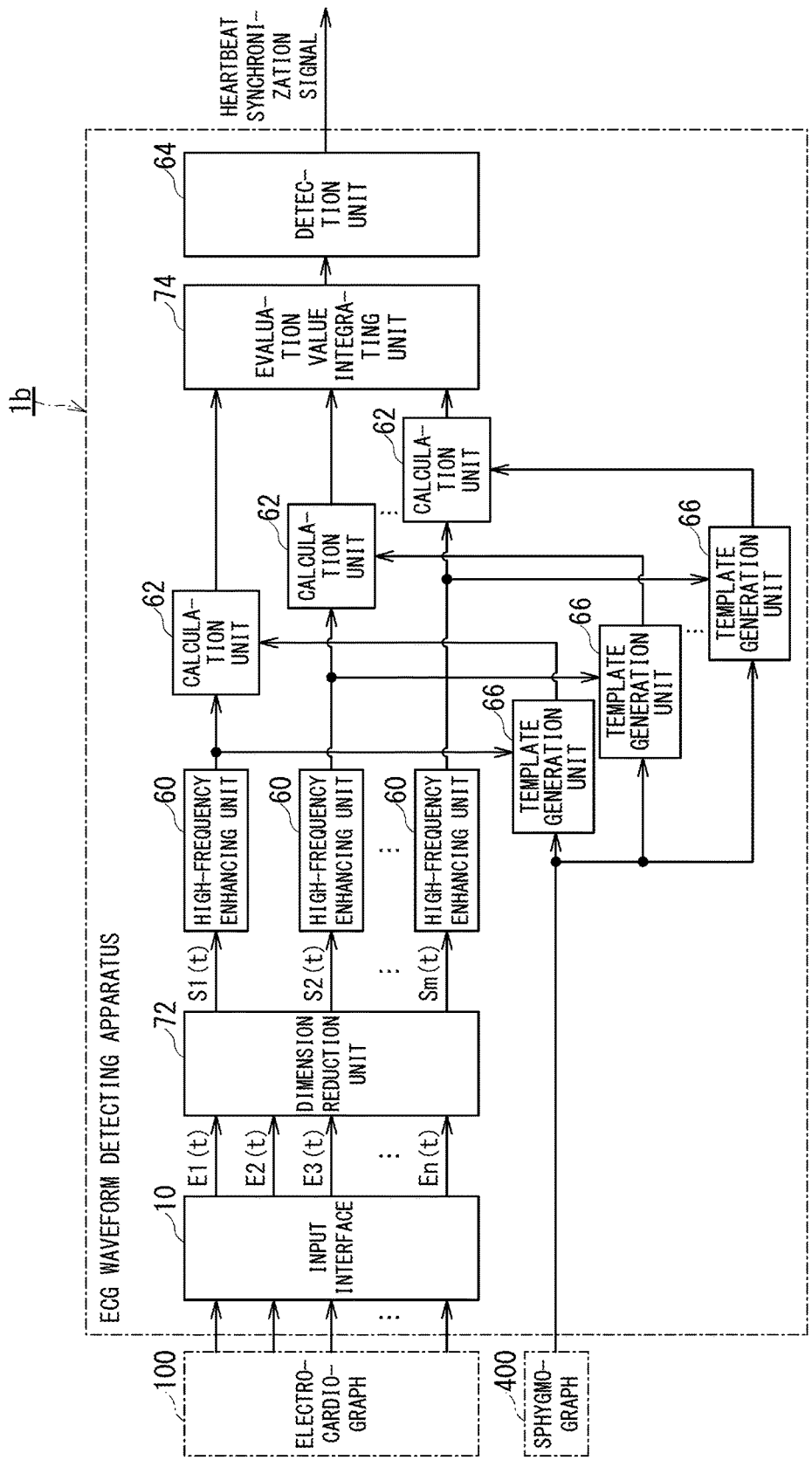
FIG. 25 is a block diagram showing an example of configuration of the ECG waveform detecting apparatus of the third modification of the second embodiment.

In the third modification of the second embodiment, R-waves are detected from these multi-dimensional ECG signals outputted from the electrocardiograph 100. FIG. 25 is a block diagram showing an example of configuration of the ECG waveform detecting apparatus 1b of the third modification of the second embodiment. The ECG waveform detecting apparatus 1b includes a dimension reduction unit 72 and an evaluation value integrating unit 74. In addition, the ECG waveform detecting apparatus 1b includes plural high-frequency enhancing units 60 and plural calculation units 62. The dimension reduction unit 72 reduces the number of ECG signals (i.e. dimension number) outputted from the electrocardiograph 100. For example, when the number of ECG signals outputted from the electrocardiograph 100 is n (n-dimensional signals), the outputted ECG signals are converted into m-dimensional signals whose dimension number is smaller than n (m<n). For example, principal component analysis is performed on the n-dimensional ECG signals of a predetermined period inputted in the past so as to calculate principal component vectors. After this, the dimension number can be reduced from n-dimension to m-dimension by projecting the inputted n-dimensional ECG signals onto a partial space generated from m (m<n) principal component vectors whose contribution rate is large.

ECG signals whose dimension number is reduced, i.e. ECG signals whose signal number is reduced from n to m are inputted to the respective m high-frequency enhancing units 60 one by one. Incidentally, the plural ECG signals outputted from the electrocardiograph 100 may be inputted to the high-frequency enhancing units 60 without reducing the dimension of ECG signals. In this case, the dimension reduction unit 72 is unnecessary.

Each of the high-frequency enhancing unit 60 performs the high-frequency enhancement processing similar to the first embodiment on each of the inputted ECG signals. Here, if m ECG signals are indicated by an m-dimensional vector signal S(t), the vector signal S(t) is given as follows.

$$S(t)=(S1(t),S2(t),S3(t), \ldots ,Sm(t))$$

Each of the high-frequency enhancing units 60 generates the high-frequency enhanced ECG signal by separately applying the FIR filter having the above-mentioned filter coefficients to S1(t), S2(t), S3(t), . . . , and Sm(t), for example. In this case, each of the high-frequency enhancing units 60 is configured as a single-input single-output FIR filter. Then, m high-frequency enhancing units 60 output m high-frequency enhanced ECG signals as a whole.

For example, in the case of a vectorcardiogram, the above-mentioned three signals X, Y, and Z are respectively inputted to three high-frequency enhancing units 60 as S1(t), S2(t), and S3(t). Then, three high-frequency enhanced signals are outputted from the respective high-frequency enhancing units 60.

Incidentally, the high-frequency enhancing unit 60 may be configured as a multi-dimensional FIR filter of multi-input multi-output type. For example, when input signals are three-dimensional signals of X, Y, and Z corresponding to a vectorcardiogram, the high-frequency enhancing unit 60 may be configured as a three-dimensional FIR filter of three-input three-output type.

The high-frequency enhanced ECG signals, whose number is m, and which are generated in the respective high-frequency enhancing units 60, are inputted to the respective template generation units 66 whose number is m. Each of the template generation units 66 generates the high-frequency enhanced template. The template generation units 66 inputs the generated high-frequency enhanced templates to the respective calculation units 62 whose number is m. The operation of each template generation unit 66 is the same as the second embodiment, and its first and second modifications.

Each of the calculation units 62 calculates an evaluation value such as the cross-relation, or the total sum of the difference square values, on the basis of the high-frequency enhanced ECG signals outputted from the respective high-frequency enhancing units 60 and the high-frequency enhanced templates outputted from the respective template generation units 66. The operation of each of the calculation unit 62 is the same as the second embodiment and its first and second modifications.

The evaluation value integrating unit 74 calculates one synthetic evaluation value by integrating totally m evaluation values outputted from m calculation units 62. For example, one synthetic evaluation value may be calculated by simply adding m evaluation values. Alternatively, by appropriately weighting m evaluation values so as to obtain a weighted sum value, the weighted sum value may be determined as the synthetic evaluation value.

The detection unit 64 detects R-waves on the basis of the synthetic evaluation value inputted from the evaluation value integrating unit 74. The operation of the detection unit 64 is the same as the second embodiment and its first and second modifications.

According to the ECG waveform detecting apparatus 1b of third modification of the second embodiment, detection of R-waves with the use of information on multi-dimensional ECG signals outputted from the electrocardiograph 100 is enabled.

(The Third Embodiment)

Figure 26:
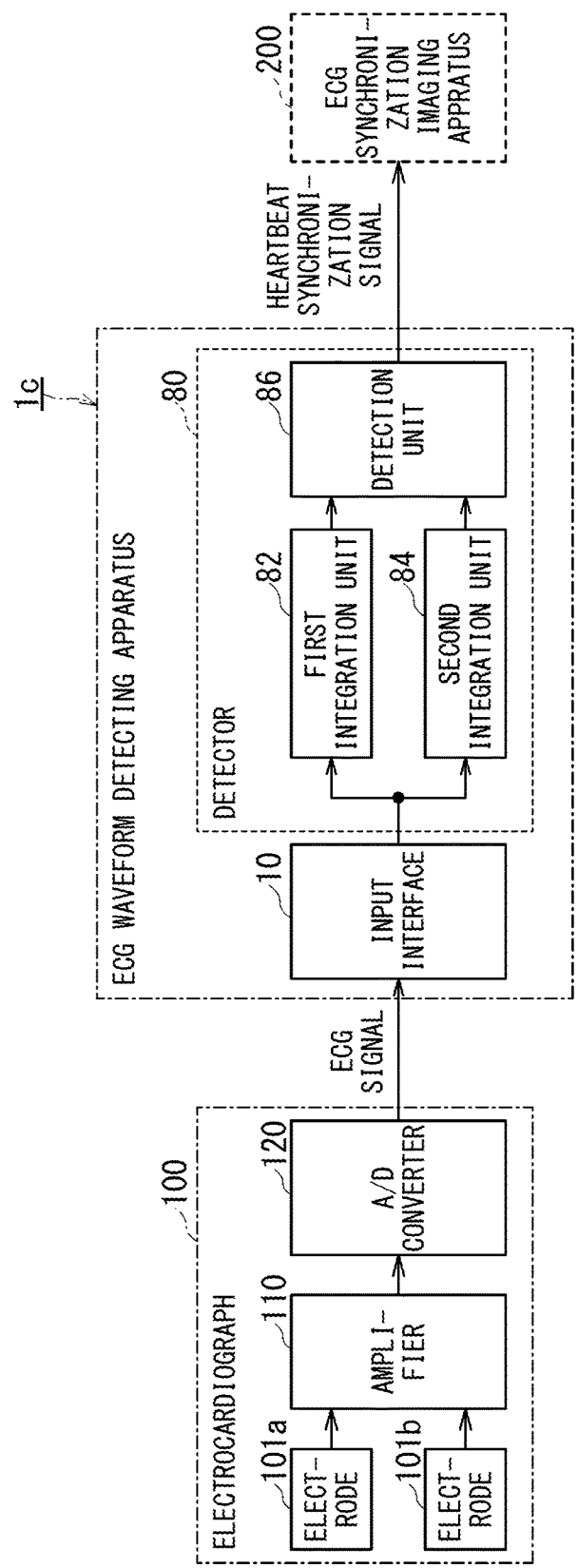
FIG. 26 is a block diagram showing an example of configuration of the ECG waveform detecting apparatus of the third embodiment.

FIG. 26 is a block diagram showing an example of configuration of the ECG waveform detecting apparatus 1c of the third embodiment and configuration of each apparatus connected to the ECG waveform detecting apparatus 1c. The electrocardiograph 100 generates an ECG signal, and transmits the generated ECG signal to the ECG waveform detecting apparatus 1c. The ECG waveform detecting apparatus 1c generates a heartbeat synchronization signal from the ECG signal, and transmits the generated heartbeat synchronization signal to the ECG synchronization imaging apparatus 200.

The electrocardiograph 100 and the ECG synchronization imaging apparatus 200 are each the same as the first embodiment, and duplicated explanation is omitted.

The ECG waveform detecting apparatus 1c includes the input interface 10, a first integration unit 82, a second integration unit 84, and a detection unit 86. The entirety of the first integration unit 82, the second integration unit 84, and the detection unit 86 configures a detector 80.

The input interface 10 acquires the ECG signal from the A/D converter 120. The first integration unit 82 calculates an integrated value of the acquired ECG signal during a first period, as the first integrated value. The second integration unit 84 calculates an integrated value the acquired ECG signal during a second period, as the second integrated value. The detection unit 86 detects a specific target waveform in the ECG signals by using the first integrated value and the second integrated value. More specifically, the detection unit 86 calculates the difference between the first integrated value and the second integrated value and detects the target waveform by comparing the difference with a predetermined reference value (threshold value).

The length of each of the first period and the second period, the interval between the first period and the second period, and the reference value are preliminarily determined to appropriate values.

The appropriate values for the length of the first period, the length of the second period, the interval between the first and second periods, and the reference value can be determined by performing simulation based on multiple ECG signals actually acquired from human bodies, for example, while parametrically changing the above values. For example, a detection period corresponding to the target waveform is set with respect to the ECG signal, and within this detection period, the length of the first period, the length of the second period, the interval between the first and second periods, and the reference value are parametrically changed. Afterward, each value is determined in such a manner that the target waveform is detected with as high detection performance as possible. In other words, the length of the first period, the length of the second period, the interval between the first and second periods, and the reference value are tuned (or adjusted) so as to detect the target waveform with high detection performance. The above high detection performance means that the probability of correctly detecting the target waveform (correct detection rate) is high and the probability of detecting a waveform other than the target waveform (incorrect detection rate) is low.

Figure 27:
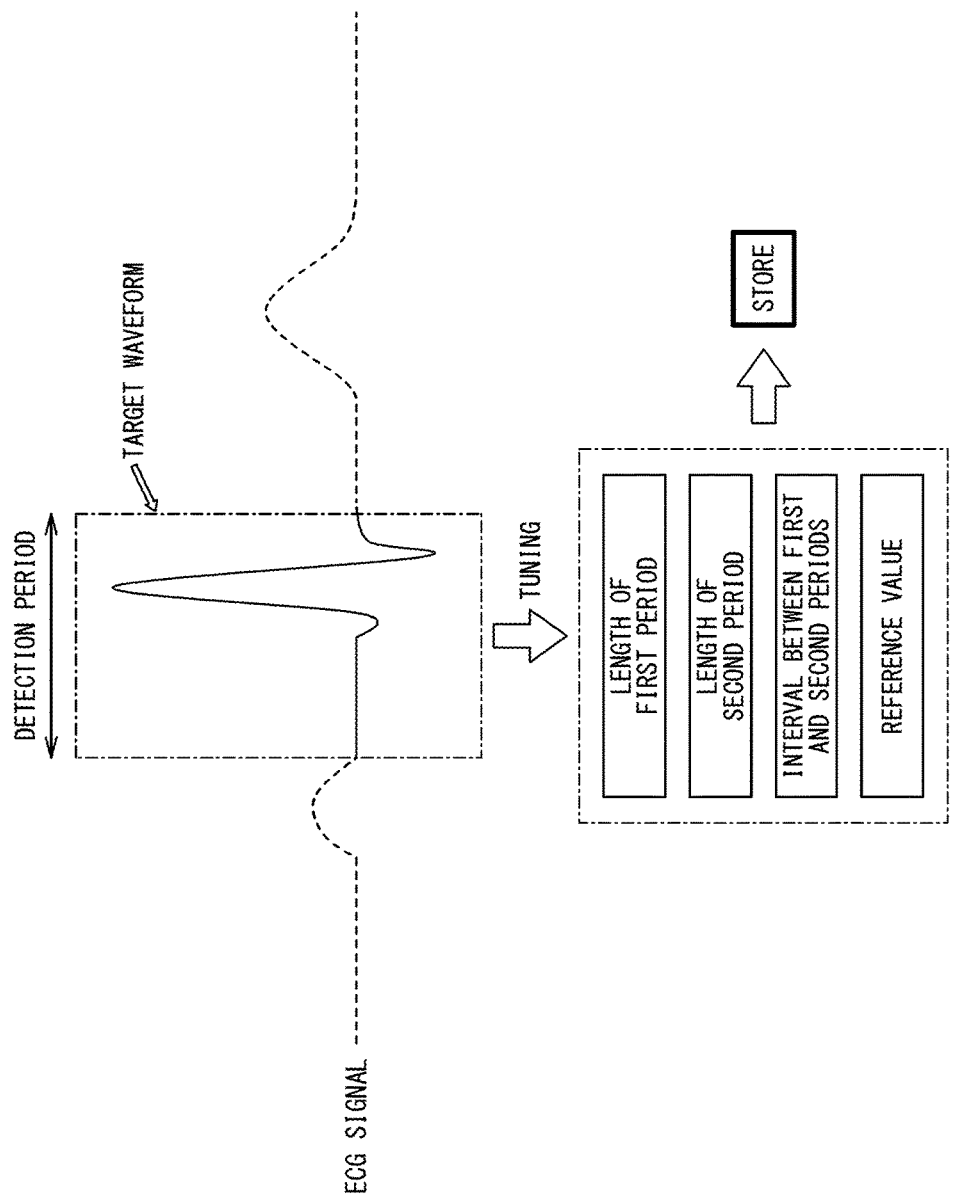
FIG. 27 is a diagram explaining an example of a method of determining a parameter used for detection processing in the third embodiment.

For example, under the assumption that the target waveform in an ECG waveform is the solid line in FIG. 27, (a) the detection period corresponding to this target waveform is set, (b) the length of the first period, the length of the second period, the interval between the first and second periods, and the reference value are parametrically varied, and then (c) each value is determined as the result of tuning so that the target waveform can be detected as accurately as possible.

The length of the first period, the length of the second period, the interval between the first and second periods, and the reference value each determined in the above manner are stored in an appropriately installed storage circuit of this apparatus and then respectively provided to the first integration unit 82, the second integration unit 84, and the detection unit 86.

When the detection unit 86 detects the target waveform, it generates the ECG synchronization signal. In addition, the detection unit 86 transmits the generated ECG synchronization signal to the ECG synchronization imaging apparatus 200.

Each unit of the ECG waveform detecting apparatus 1c may be configured as hardware such as ASIC, an FPGA, or each function of the units may be achieved by software processing. Alternatively, each unit or each function of the units of the ECG waveform detecting apparatus 1c may be achieved by combination of hardware and software processing. When it is achieved by software processing, operations of the respective units of the ECG waveform detecting apparatus 1c can be realized by causing the computer 300 illustrated in FIG. 3 to execute predetermined programs in the way similar to the first and second embodiments.

Figure 28:
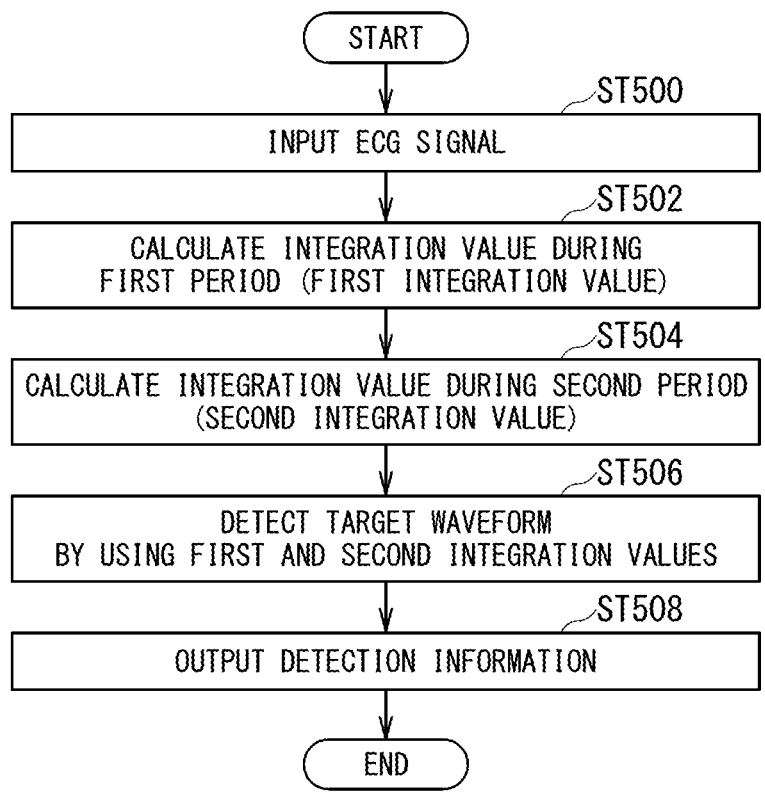
FIG. 28 is a flowchart showing an example of a general outline of processing performed by the ECG waveform detecting apparatus of the third embodiment.

FIG. 28 is a flowchart showing an example of a general outline of the processing performed by the ECG waveform detecting apparatus 1c. In the step ST500, the input interface 10 of the ECG waveform detecting apparatus 1c inputs an ECG signal as a time-series signal. The ECG signal is, for example, a signal sampled at a constant interval (for example, a sampling interval of 1 millisecond).

In the step ST502, the first integration unit 82 calculates an integrated value (the first integrated value) during the first period. In the step ST504, the second integration unit 84 calculates an integrated value (the second integrated value) during the second period. The order of the step ST502 and the step ST504 may be reversed. In addition, the processing of the step ST502 and the processing of the step ST504 may be performed in parallel.

In the step ST506, the detection unit 86 calculates the difference value between the first integrated value and the second integrated value. Moreover, the detection unit 40 detects the target waveform by comparing the calculated difference value with the preliminarily stored reference value.

In the step ST508, the detection unit 86 outputs detection information. The detection information is, for example, "+1" or "−1". If the target waveform has been detected, "+1" is outputted. Otherwise, "−1" is outputted. In addition, if the target waveform has been detected, the detection unit 86 inputs the heartbeat synchronization signal to the ECG synchronization imaging apparatus 200.

Figure 29:
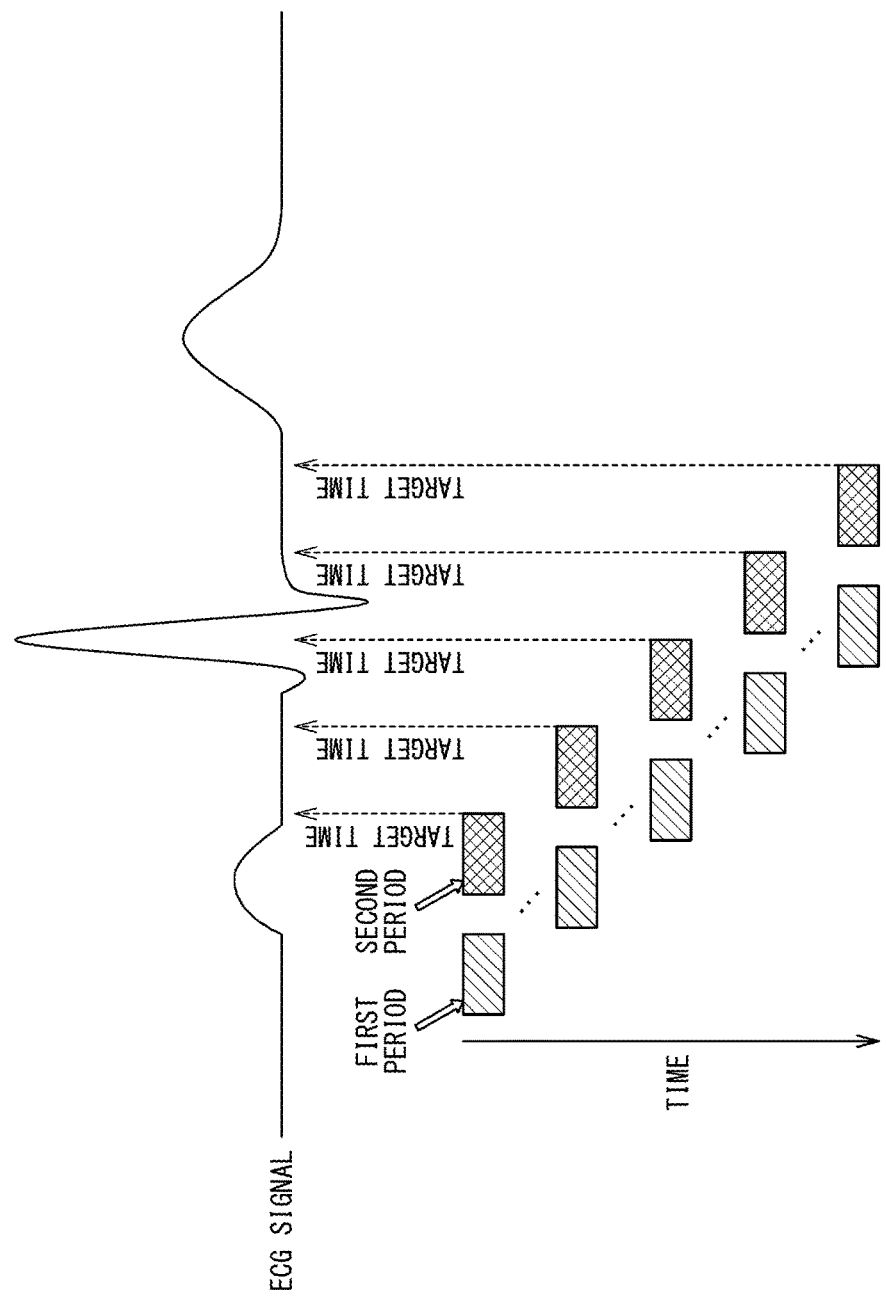
FIG. 29 is a diagram showing an example of comparison of target time on an ECG signal between the first period as the integration period of the first integration unit and the second period as the integration period of the second integration unit.

FIG. 29 is a diagram showing the comparison of target time on the ECG signal between the first period as the integration period of the first integration unit 82 and the second period as the integration period of the second integration unit 84. If the time required for the detection processing by the detection unit 86 is ignored, the detection result of the detection unit 86 for the target waveform is obtained at the time when both of the first integrated value and second integrated value are obtained (the ending time of the second period in FIG. 29). Thus, the ending time of the second period is the target time.

In order to detect each target waveform from the time-sequentially inputted ECG signal, the processing from the step ST502 to the step ST508 in FIG. 28 may be repeated by shifting the target time with respect to the temporal sequence of ECG signal, as shown in FIG. 29.

As mentioned above, the ECG waveform detecting apparatus 1c of the third embodiment detects the target waveform by performing two integration calculations, one subtraction calculation, and one comparison process. In other words, the target waveform can be detected with extremely small computation amount.

(The First Modification of the Third Embodiment)

Figure 30:
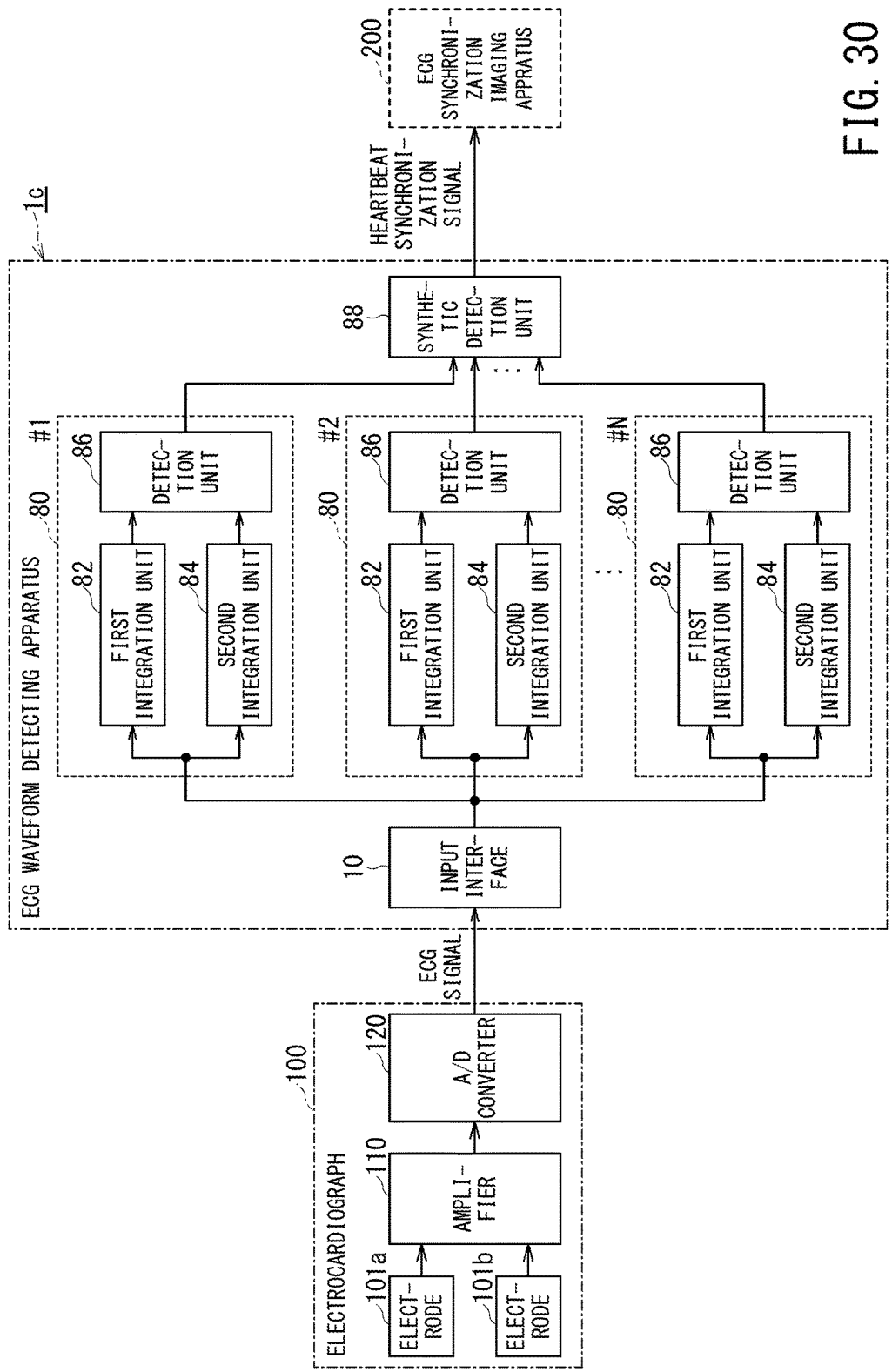
FIG. 30 is a block diagram showing an example of configuration of the ECG waveform detecting apparatus of the first modification of the third embodiment.

FIG. 30 is a block diagram showing an example of configuration of the ECG waveform detecting apparatus 1c of the first modification of the third embodiment. The ECG waveform detecting apparatus 1c of the first modification of the third embodiment includes plural detectors 80 and a synthetic detection unit 88 which integrates detection information outputted from each of the detectors 80.

In the example of FIG. 30, the ECG waveform detecting apparatus 1c includes N detectors 80 from #1 to #N, and in association with this, each number of the first integration units 82, the second integration units 84, and the detection units 86 is set to N.

The operation of each of the detectors 80 is the same as the above-mentioned third embodiment. In other words, each of the detection units 86 compares the reference value with the difference value between the first integrated value outputted from the first integration unit 82 and the second integrated value outputted from the second integration unit 84. Then, for example, "+1" is outputted as the detection information of the target waveform if the difference value exceeds the reference value, and "−1" is outputted as the detection information if the difference value does not exceed the reference value.

The synthetic detection unit 88 applies predetermined weights to the detection information of "+1" or "−1" outputted from each of the detectors 80. Then, the synthetic detection unit 88 generates a weighted sum value of "+1" and "−1" by summing up the weighted detection information of each detector 80. Moreover, the synthetic detection unit 88 calculates the conclusive integrated detection information by comparing the weighted sum value with a predetermined integrated reference value. Here, the integrated reference value is a threshold value applied to the weighted sum value. For example, the integrated reference value as the threshold value may be set to zero, and it may be determined that a predetermined target waveform has been detected when a positive weighted sum value is obtained.

The above value of weighting and the integrated reference value used in the synthetic detection unit 88 are preliminarily determined and stored in the synthetic detection unit 88, in the way similar to the length of integration period, the interval between integration periods, and the reference value used by the respective detectors 80. The value of weighting and the integrated reference value are determined by performing simulation based on multiple ECG signals actually acquired from human bodies while parametrically changing these values in the simulation, and are tuned so that the target waveform is detected with as high detection performance as possible.

Figure 31:
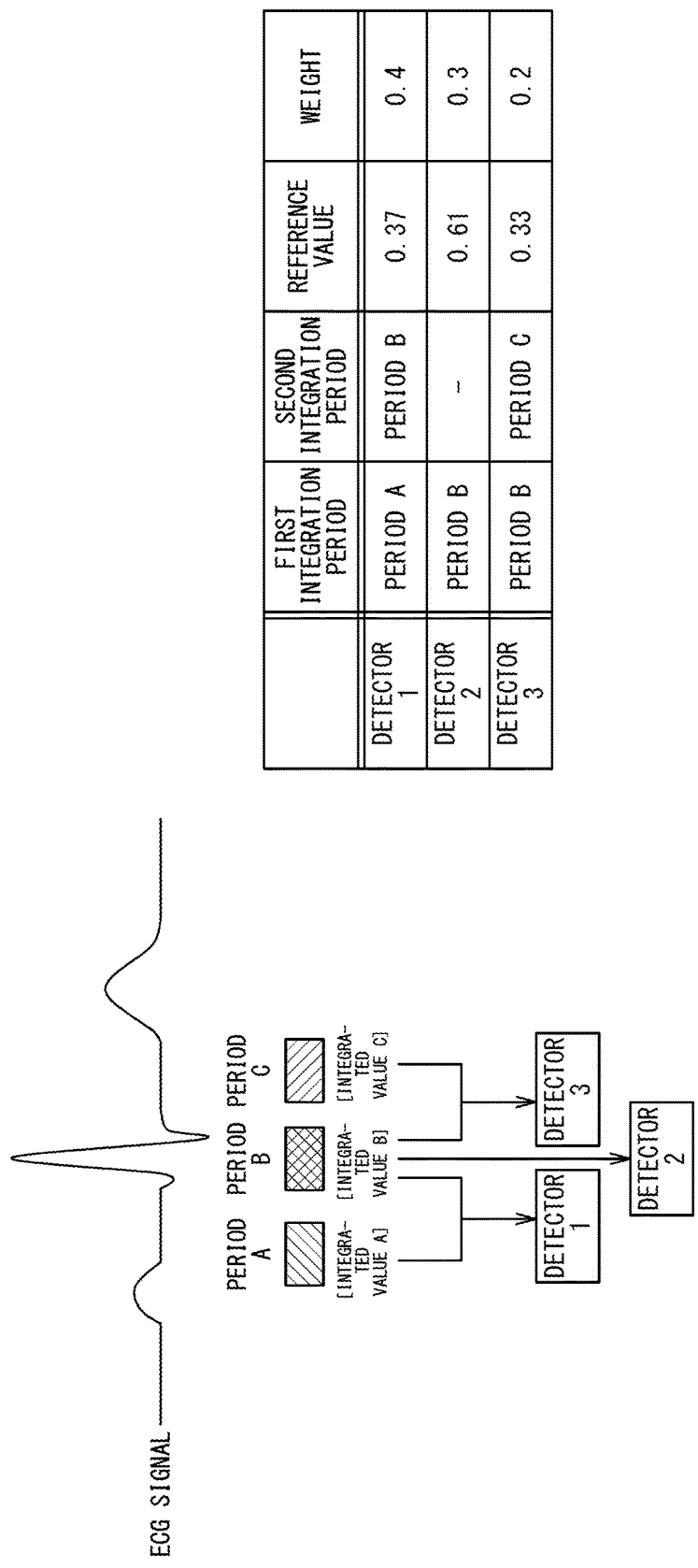
FIG. 31A and FIG. 31B are diagrams explaining operation of the ECG waveform detecting apparatus configured to include three detectors as an example.

FIG. 31A and FIG. 31B are diagrams explaining operation of the ECG waveform detecting apparatus 1c configured to include a detector 1, a detector 2, and a detector 3 as the plural detectors 80 as an example. In the example of FIG. 31A, three periods: a period A, a period B, and a period C are set in the order of earlier time.

The detector 1 is a detector which calculates a difference between the integrated value A during the period A and the integrated value B during the period B. A large difference value is obtained if an R-wave arrives in the period B, otherwise, a small difference value is obtained. Thus, by comparing the difference value with a predetermined reference value (i.e. threshold value, which is set to 0.37 in the example of FIG. 31B), it can be determined that an R-wave has been detected if the difference value exceeds the reference value.

The detector 3 is a detector which calculates a difference between the integrated value B during the period B and the integrated value C during the period C. In the way similar to the detector 1, a large difference value is obtained if an R-wave arrives in the period B. If this is not the case, a small difference value is obtained. Thus, by comparing the difference value with an predetermined reference value (i.e. threshold value, which is set to 0.33 in the example of FIG. 31B), it can be determined that an R-wave has been detected if the difference value exceeds the reference value. Incidentally, the difference result is obtained after completion of the period B in the detector 1. By contrast, the difference result is obtained after completion of the period C in the detector 3. Therefore, the time at which the detection result of an R-wave is obtained in the detector 3 becomes later than that of the detector 1.

The detector 2 uses only the integrated value of the period B. The detector 2 can be used, for example, as a supplementary detector for adjusting the reference values of the respective detectors 1 and 3. For example, the detector 2 is made to operate with the target time shifted gradually. Then, when the integrated value exceeds a predetermined reference value (0. 61 in the example of FIG. 31B) stored in the detector 2 in a separately determined period, the peak value in excess of the reference value is held. In this case, the peak value is considered to indicate the magnitude of an R-wave. Thus, by setting the respective reference values of the detectors 1 and 3 in proportion to this peak value, the respective reference values of the detectors 1 and 3 can be adaptively varied in accordance with an intensity of a target biological signal.

In an example as shown in FIG. 31B, the synthetic detection unit 88 respectively sets the weight of 0.4 to the detection information of the detector 1, the weight of 0.3 to the detection information of the detector 2, and the weight of 0.2 to the detection information of the detector 3. Then, the synthetic detection unit 88 applies weighted addition on the detection information outputted from each of the detectors 1, 2, and 3 (for example, to the value of "+1" or "−1") with the above weights, so as to calculate the weighted sum value. Afterward, the synthetic detection unit 88 obtains the conclusive integrated detection information by comparing the weighted sum value with the integrated reference value.

In the ECG waveform detecting apparatus 1c of the first modification of the third embodiment, at least one of the first period and the second period with respect to ECG signals is/are different for each detector. For instance, in the above example, the first period of the detector 1 is the period A and the second period of the detector 1 is the period B. In addition, the first period of the detector 3 is the period B and the second period of the detector 3 is the period C. Accordingly, (a) by causing each of the detectors to detect the target waveform using information obtained from each different integration period and (b) by integrating the respective detection results with the use of weighted addition, the target waveform can be detected with higher detection performance as compared with a case of detecting by one detector. In other words, the probability of correctly detecting the target waveform (correct detection rate) can be improved and the probability of erroneously detecting a waveform other than the target waveform (incorrect detection rate) can be reduced.

Figure 32:
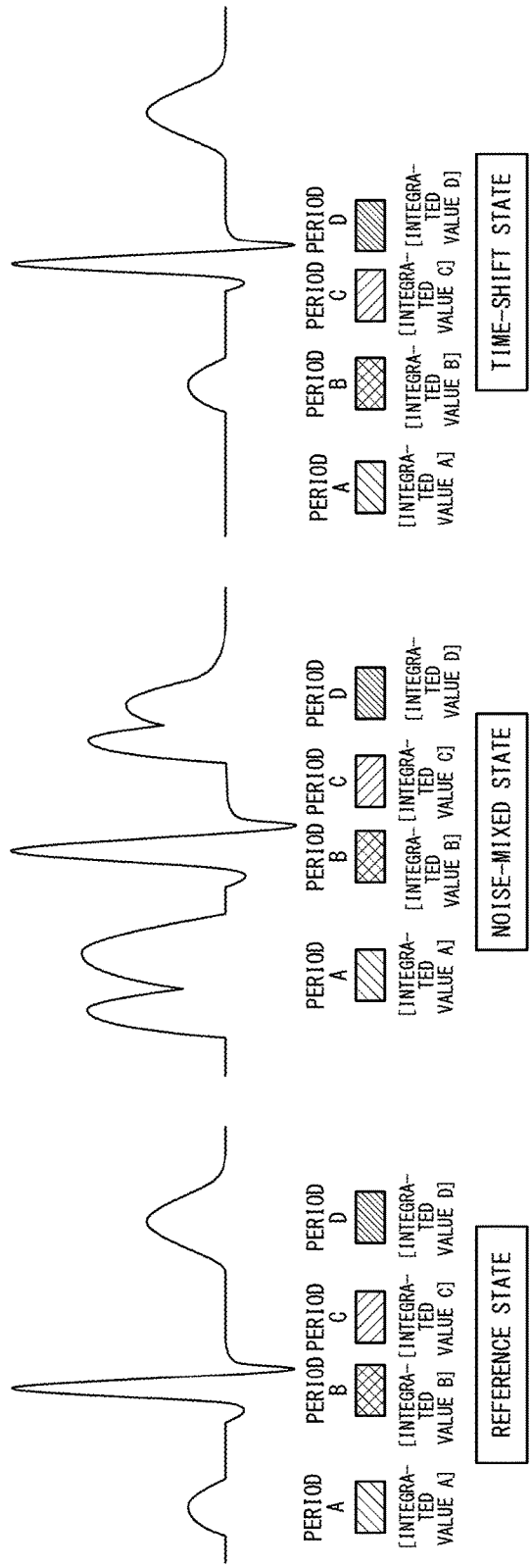
FIG. 32A to FIG. 32D are diagrams explaining operation of the ECG waveform detecting apparatus configured to include six detectors as an example.

The detection performance can be further improved by increasing the number of detectors. FIG. 32 is a diagram explaining operation of the ECG waveform detecting apparatus 1C configured to include detectors 1 to 6 as the plural detectors 80 as an example. As integration periods, four periods A, B, C and D are set.

Here, the respective integrated values of the periods A to D are defined as an integrated value A, an integrated value B, an integrated value C, and an integrated value D. As shown in the difference processing in the middle column of the table of FIG. 32D, for example, the detector 1 calculates the difference between the integrated value A and the integrated value B, the detector 2 calculates the difference between the integrated value A and the integrated value C, the detector 3 calculates the difference between the integrated value A and the integrated value D. In addition, for example, the detector 4 calculates the difference between the integrated value B and the integrated value C, the detector 5 calculates the difference between the integrated value B and the integrated value D. Furthermore, for example, the detector 6 calculates the difference between the integrated value C and the integrated value D.

FIG. 32A to FIG. 32C show a relative positional relationship of the periods A to D with respect to the ECG signal. The relative positional relationship of the periods A to D with respect to the ECG signal in FIG. 32A is the same as FIG. 32B. In both of FIG. 32A and FIG. 32B, the R-wave is at the position of the period B, the period A is earlier than the R-wave, and the period C and the period D are at the positions temporally later than the R-wave. Note that FIG. 32A is a diagram corresponding to a state where noise is not mixed into the ECG signal and FIG. 32B is a diagram corresponding to a state where noise is mixed into the ECG signal.

On the other hand, in FIG. 32C, the relative positional relationship of the periods A to D with respect to the ECG signal is different from that of FIG. 32A and FIG. 32B. In other words, the relative positions of the periods A to D with respect to the ECG signal in FIG. 32C are shifted temporally forward with reference to FIG. 32A and FIG. 32B.

Hereinafter, the state of FIG. 32A is referred to as the reference state, the state of FIG. 32B is referred to as the noise-mixed state, and the state of FIG. 32C is referred to as the time-shift state. The intensity of the difference outputs of the respective detectors 1 to 6 in each of the states are indicated in the three columns in the right side of the table of FIG. 32D. Here, "++" means that the difference output is a positive large value and "−−" means that the difference output is a negative large value. In addition, "+" means that the difference output is a positive small value and "−" means that the difference output is a negative small value.

In the example of FIG. 32D, the difference outputs of the respective detectors 1 to 6 with respect to the reference state are −−, +, −, ++, +, and − in the order from the detector 1 to 6. In the ECG waveform detecting apparatus 1c of the first modification of the third embodiment, the reference value (threshold value) is preliminarily tuned and determined for each detector, on the basis of the preliminarily acquired many ECG signals so that the respective detectors can detect these difference outputs. Then, the detection information of, for example, +1 (detected) or −1 (undetected) is obtained by performing comparative determination on each difference output with the use of the determined reference value (threshold value). Afterward, the detection information outputted from the respective detectors is further subjected to weighted addition in the synthetic detection unit 88, and comparative determination between this weight sum value and the integrated reference value is performed. The weights and the integrated reference value used by the synthetic detection unit 88 are values tuned on the basis of preliminarily acquired many ECG signals.

As just described, higher detection performance can be obtained by integrating the results of the respective outputs of plural detectors than a case of determining by using only one detector.

Meanwhile, the difference outputs of the respective detectors 1 to 6 in the noise-mixed state are −, +, −, +, +, and − in the order from the detector 1 to the detector 6. When these difference outputs are compared with the respective difference outputs in the reference state, though absolute values of the difference outputs are different between these two states, the sign of plus or minus of each of the detectors 1 to 6 indicates similar tendency between these two states. This means that the integrated detection information in the noise-mixed state and the integrated detection information in the reference state indicate mutually similar tendency if the detection information of the respective detectors is integrated. In other words, detection processing insusceptible to noise is enabled by integrating the detection information respectively outputted from of plural detectors.

By contrast, the difference outputs of the respective the detectors 1 to 6 in the time-shift state are −, −, +, +, +, and + in the order from the detector 1 to the detector 6. In other words, each difference output indicates significantly different tendency from the reference state not only in its absolute value but also in its sign. More concretely, if the output of only one specific detector is compared between the time-shift state and the reference state, the sign of the output is sometimes the same between the two states (for example, the output of the detector 1 is the same between the two states). However, if the sign of outputs of the entire six detectors is compared between these two states, the sign is different as a whole between the time-shift state and the reference state.

This means that in the case of the time-shift state (i.e. when target time of the target waveform is different and the waveform of an ECG signal at the target time is different from the target waveform in the reference state), the probability of erroneously detecting this different waveform is more reduced than a case of determining by using only one detector.

(The Second Modification of the Third Embodiment)

According to the above first modification of the third embodiment in which plural detectors are used, the entire detection performance is improved. On the other hand, the amount of the entire integral computations is increased because two integral computations are performed in each detector.

Figure 33:
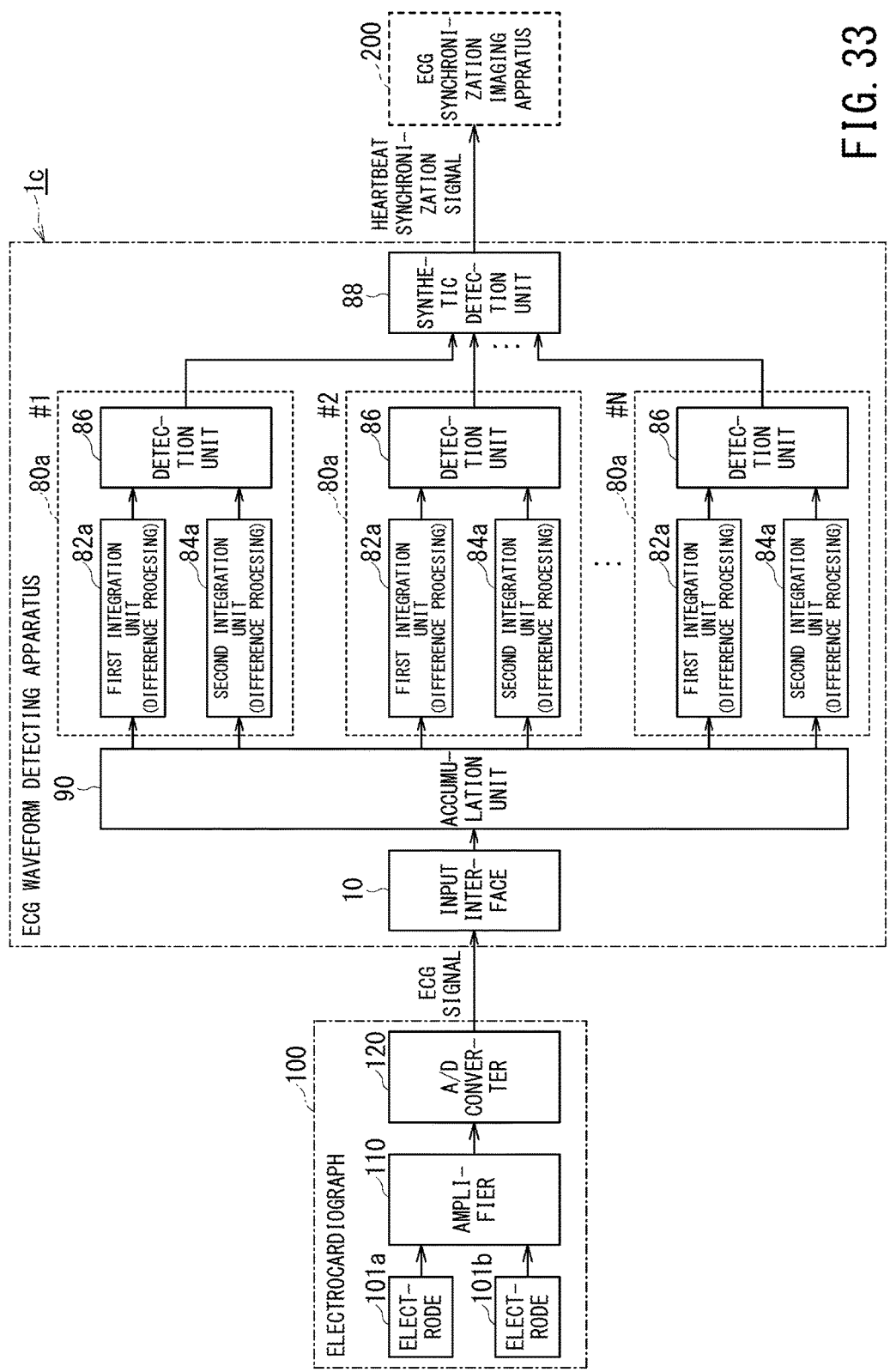
FIG. 33 is a block diagram showing an example of configuration of the ECG waveform detecting apparatus of the second modification of the third embodiment.

Accordingly, the ECG waveform detecting apparatus 1c of the second modification of the third embodiment is provided with a means of reducing the amount of the entire integral computations. FIG. 33 is a block diagram showing an example of configuration of the ECG waveform detecting apparatus 1c of the second modification of the third embodiment. The difference between this second modification and the first modification (FIG. 30) of the third embodiment lies in that an accumulation unit 90 is disposed between the input interface 10 and the respective detectors 80a. In addition, the processing respectively performed in the first integration unit 82a and the second integration unit 84a of each detector 80a is different between this second modification and the first modification.

The accumulation unit 90 calculates an accumulated value by time-sequentially accumulating ECG signals time-sequentially acquired from an object. The first integration unit 82a refers to the accumulation unit 90, and calculates the difference between the accumulated value at the start time of the first period and the accumulated value at the ending time of the first period as the first integrated value. Similarly, the second integration unit 84a refers to the accumulation unit 90, and calculates the difference between the accumulated value at the start time of the second period and the accumulated value at the ending time of the second period as the second integrated value.

Figures 34A, 34B:
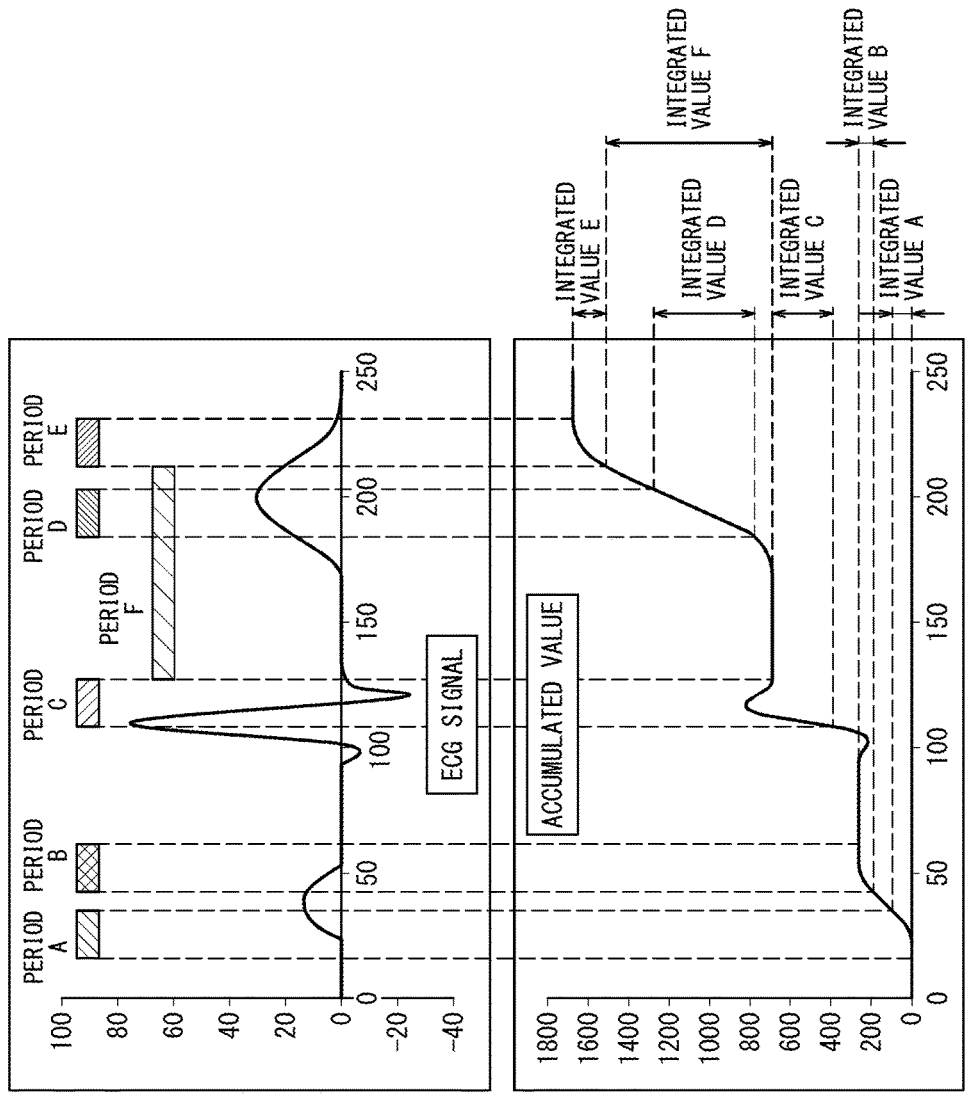
FIG. 34A and FIG. 34B are diagrams explaining operational concept of the ECG waveform detecting apparatus of the second modification of the third embodiment.

FIG. 34 is a diagram explaining operational concept of the second modification of the third embodiment. FIG. 34A illustrates a time-sequentially acquired ECG signal and plural integration target periods for the ECG signal as the periods A, B, C, D, E, and F. FIG. 34B illustrates the accumulated value of the ECG signal calculated by the accumulation unit 90. The accumulated value continues to increase while the polarity of intensity of the ECG signal is positive like the respective regions of a P-wave, an R-wave, and a T-wave. By contrast, the accumulated value slightly decreases while the polarity of intensity of the ECG signal is negative in some negative regions such as a Q-wave and an S-wave.

When the integrated value B during the period B is calculated as an example, the first integration unit 82a or the second integration unit 84a calculates the difference between the accumulated value at the start time of the period B and the accumulated value at the ending time of the period B and defines the calculated difference as the integrated value B. The respective integrated values for the other periods can be calculated in the similar manner.

As mentioned above, in the second modification of the third embodiment, the integrated values can be obtained by simply calculating the difference between two values obtained by referring to the respective accumulated values (at the start time and the ending time of the integration period) without performing actual integration computation in the first integration unit 82a and the second integration unit 84a. Therefore, the amount of computations required for integration computation can be reduced. This effect of reduction in computation amount becomes more remarkable as the number of detector increases.

In addition, processing content of integration computation does not need to be changed, even if the length of the first and second integration periods, and interval between integration periods are different between the respective detectors.

Incidentally, the above-mentioned second modification of the third embodiment may be applied to configuration of including only one detector 80a (like the third embodiment).

(The Third Modification of the Third Embodiment)

Figure 35:
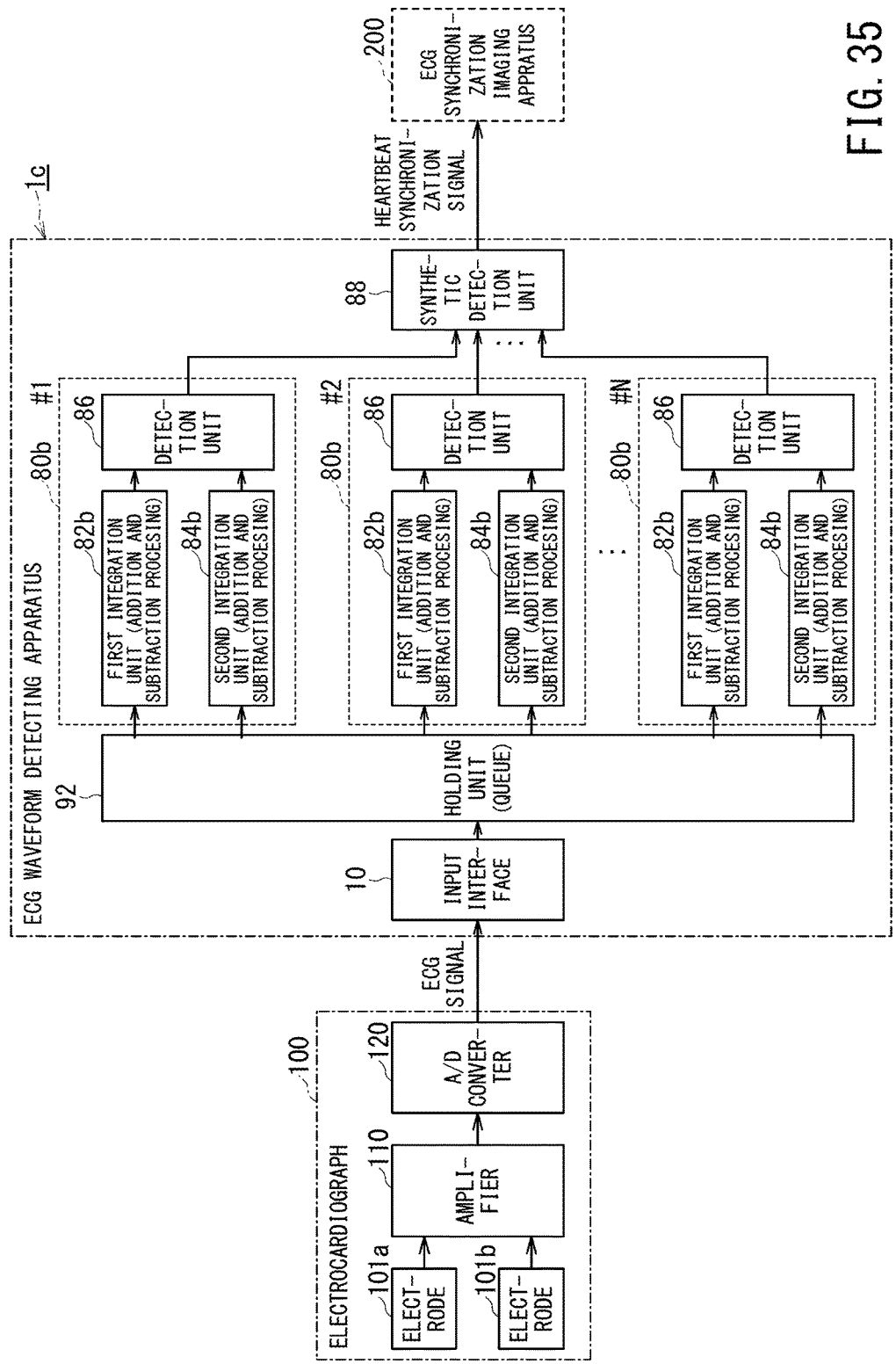
FIG. 35 is a block diagram showing an example of configuration of the ECG waveform detecting apparatus of the third modification of the third embodiment.

The ECG waveform detecting apparatus 1c of the third modification of the third embodiment includes a means of reducing the amount of the entire integral computations which is different from the second modification. FIG. 35 is a block diagram showing an example of configuration of the ECG waveform detecting apparatus 1c of the third modification of the third embodiment. The difference between this third modification and the second modification (FIG. 33) lies in that a holding unit 92 is disposed between the input interface 10 and the respective detectors 80b instead of the accumulation unit 90. In addition, the processing respectively performed by the first integration unit 82b and the second integration unit 84b of each detector 80b is slightly different from the second modification.

The holding unit 92 operates as a so-called queue circuit, and temporarily holds time-sequential sample values of ECG signals. In addition, when the first integration unit 82b of the third modification acquires a new sample value for the first period, the first integration unit 82b subtracts the sample value at the start time of the first period held in the holding unit 92 from the current first integrated value and then updates the first integrated value by adding the acquired new sample value to the first integrated value subjected to the above subtraction. Similarly, when the second integration unit 84b of the third modification acquires a new sample value for the second period, the second integration unit 84b subtracts the sample value at the start time of the second period held in the holding unit 92 from the current second integrated value and then updates the second integrated value by adding the acquired new sample value to the second integrated value subjected to the above subtraction.

Figure 36:
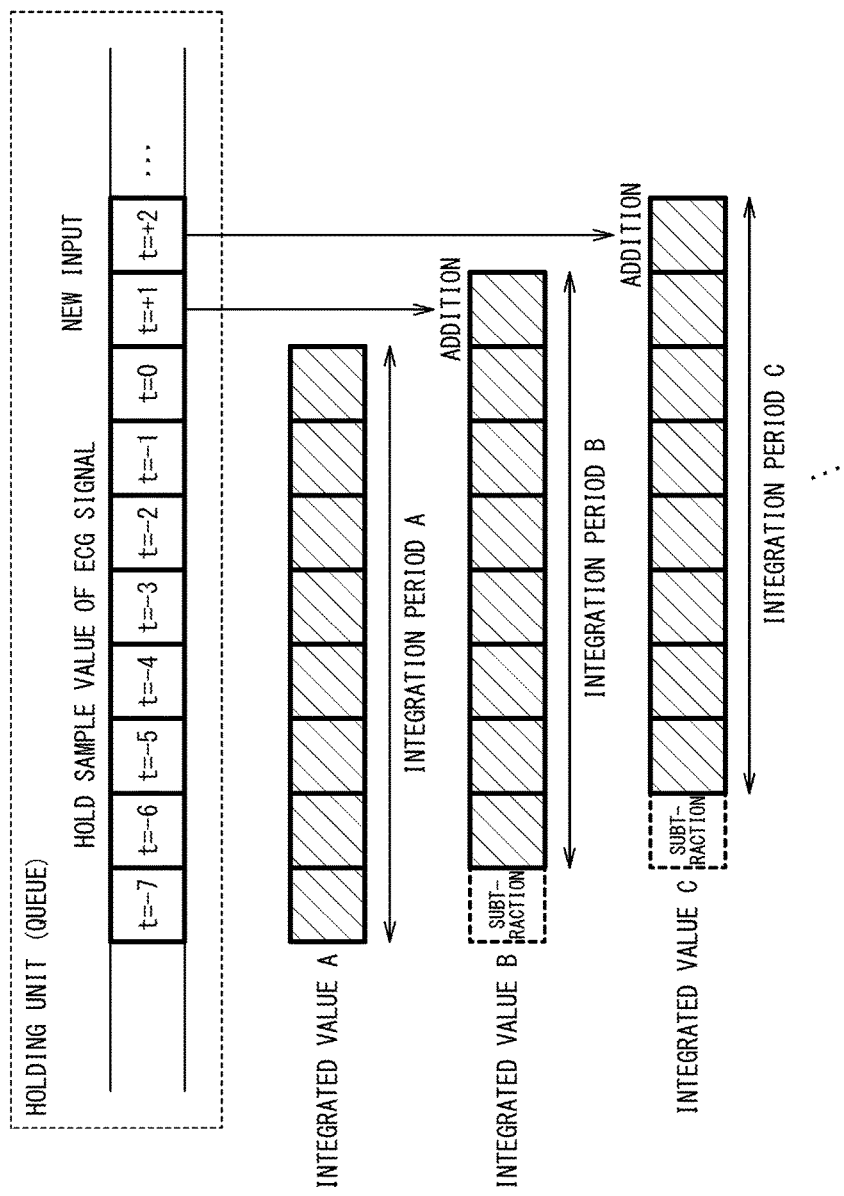
FIG. 36 is a diagram explaining the operational concept of the ECG waveform detecting apparatus of the third modification of the third embodiment.

FIG. 36 is a diagram explaining the operational concept of the ECG waveform detecting apparatus 1c of the third modification of the third embodiment. Here, it is assumed that the integration period A is a period from sample time t=−7 to t=0 and the integrated value A corresponding to this period is the total sum of the eight sample values in this period. In this case, the holding unit 92 is assumed to store at least sample values from t=−7 as the start time of the integration period A to t=0 as the current time.

Here, when a new sample value of an ECG signal at a new sampling time t=+1 is inputted, the holding unit 92 adds this new sample value to its queue.

Meanwhile, when the first integration unit 82b (or the second integration unit 84b) calculates the integrated value B corresponding to the integration period B shifted by one sampling span with respect to the integration period A, it subtracts the sample value at the start time of the integration period A (i.e. the sample value at t=−7) from the integrated value A and then obtains the integrated value B by adding the newly acquired sample value at t=+1 to the integrated value A which is subjected to the above subtraction. In other words, the integrated value B can be obtained not by integrating all the sample values during the integration period but by adding one sample value and subtracting one sample value to/from the integrated value A one before.

By repeating such processing each time a new sample value is inputted, many integrated values respectively corresponding to many integration periods whose positional relationships with respect to ECG signals are mutually different can be calculated with small computation amount.

Incidentally, even if mutually different integration units like the first integration unit 82b and the second integration unit 84b are included or even if each of the plural detectors 80b is provided with the plural first integration units 82b and the plural second integration units 84b, one holding unit (queue circuit) 92 can be commonly used for storage of sample values for all the integration units.

As mentioned above, in the third modification of the third embodiment, the computation amount required for integration computation can be reduced and this effect of reduction in the computation amount becomes more remarkable as the number of detector increases.

Incidentally, the above-mentioned third modification of the third embodiment may be applied to configuration of including only one detector 80b (like the third embodiment).

(The Fourth Embodiment)

Figure 37:
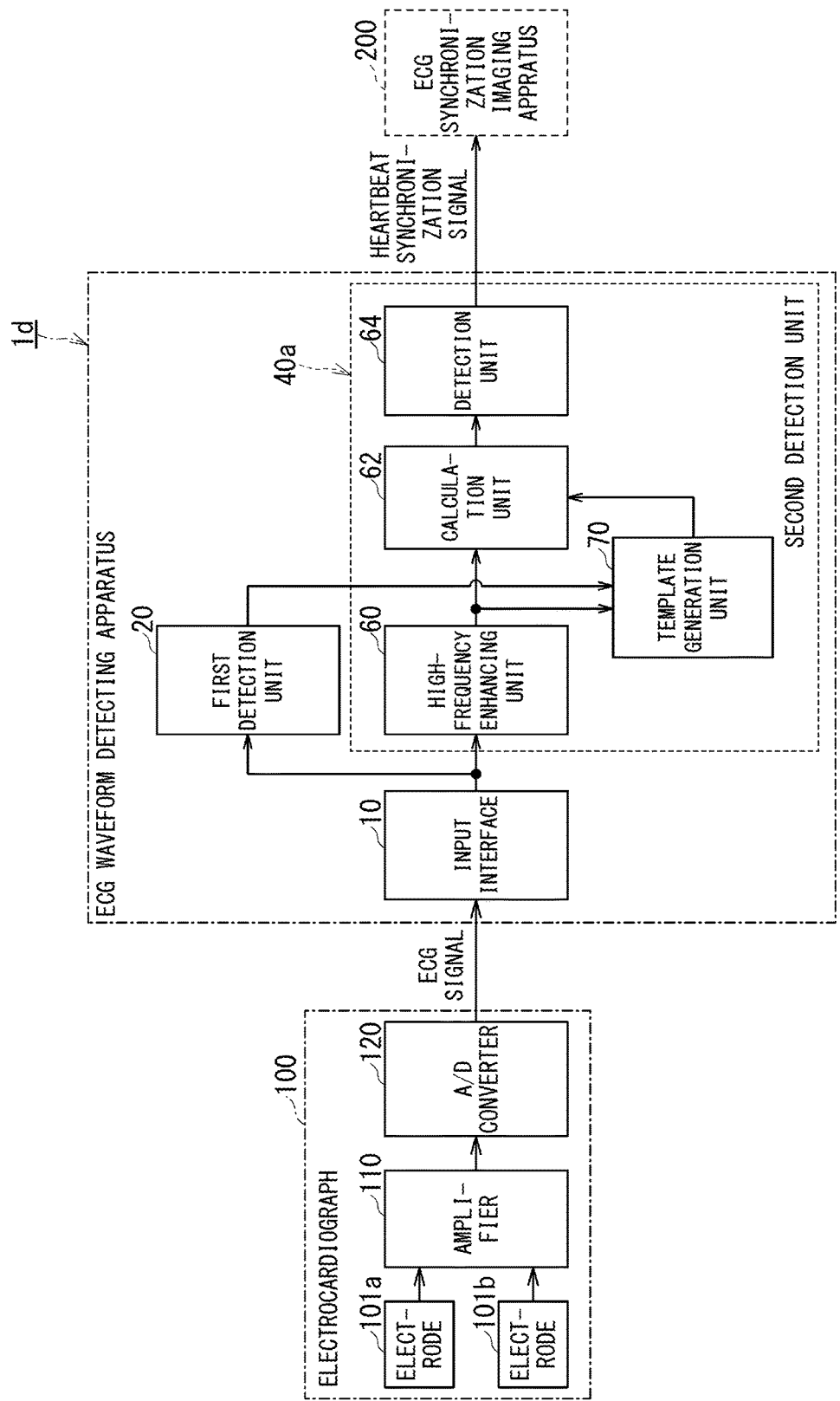
FIG. 37 is a block diagram showing an example of configuration of the ECG waveform detecting apparatus of the fourth embodiment.

The ECG waveform detecting apparatus 1d of the fourth embodiment is substantially an embodiment equivalent to combination of the ECG waveform detecting apparatus 1a of the first embodiment and the ECG waveform detecting apparatus 1b of the second embodiment. FIG. 37 is a block diagram showing an example of configuration of the ECG waveform detecting apparatus 1d of the fourth embodiment. The ECG waveform detecting apparatus 1d includes the input interface 10, the first detection unit 20, and a second detection unit 40a. The second detection unit 40a includes the high-frequency enhancing unit 60, the calculation unit 62, the template generation unit 66, and the detection unit 64.

The first detection unit 20 detects R-waves included in ECG signals. Although the first detection unit 20 may detects R-waves by using the template matching, the detection method is not limited to this aspect and various known detection methods can be used in the first detection unit 20.

By contrast, configuration of the second detection unit 40a is substantially the same as the ECG waveform detecting apparatus 1b of the second embodiment (FIG. 14). The second detection unit 40a generates the template corresponding to an R-wave as the detection target signal, i.e. the high-frequency enhanced template, on the basis of the high-frequency enhanced ECG signal generated in the high-frequency enhancing unit 60. The template generation unit 66 generates the high-frequency enhanced template by extracting the high-frequency enhanced ECG signal of the period corresponding to an R-wave, as shown in FIG. 19A and FIG. 19B. Incidentally, though the extraction position of the high-frequency enhanced template is assumed to be determined on the basis of the pulse wave signal inputted from the sphygmograph 400 in the second embodiment, it is assumed to be determined on the basis of the position of an R-wave detected by the first detection unit 20 in the fourth embodiment.

According to the ECG waveform detecting apparatus 1d of the fourth embodiment, frequency of erroneous detection caused by noise and unnecessary signals except R-waves can be reduced without requiring external devices such as the sphygmograph 400, and thus highly reliable detection of R-waves can be achieved.

Incidentally, each modification of the second embodiment can be applied to the second detection unit 40a. In addition, as explained with FIG. 8 in the first embodiment, the high-frequency enhanced template substantially equivalent to the second waveform template can be sequentially updated so as to correspond to the time-sequentially inputted ECG signals.

In each of the above-mentioned embodiments and their modifications, examples in which each of the ECG waveform detecting apparatuses 1a to 1d is a component separated from the ECG synchronization imaging apparatus 200 have been explained. By contrast, the same configuration as the ECG waveform detecting apparatuses 1a to 1d is defined as the ECG waveform detecting unit 500, and this ECG waveform detecting unit 500 may be installed in the ECG synchronization imaging apparatus 200.

Figure 38:
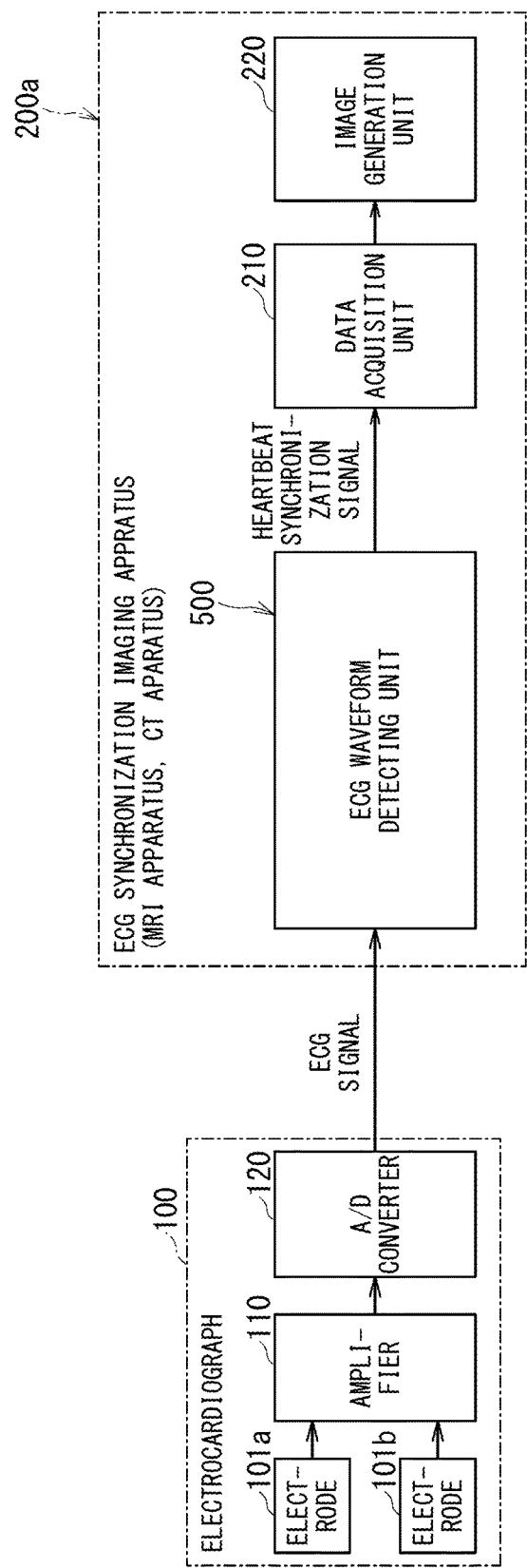
FIG. 38 is a block diagram showing an example of configuration in which the ECG synchronization imaging apparatus includes an ECG waveform detecting unit.

FIG. 38 is a block diagram showing an example of configuration in which the ECG synchronization imaging apparatus 200a includes the ECG waveform detecting unit 500. The ECG synchronization imaging apparatus 200a includes a data acquisition unit 210 configured to acquire imaging data from an object in synchronization with a heartbeat synchronization signal, and an image generation unit 220 configured to generate images of the object from the acquired imaging data, in addition to the ECG waveform detecting unit 500 that generates heartbeat synchronization signals.

In addition, examples in which each of the ECG waveform detecting apparatuses 1a to 1d is a component separated from the electrocardiograph 100 have been explained in each of the above-mentioned embodiments and their modifications. By contrast, the electrocardiograph 100 and the ECG waveform detecting unit 500 corresponding to the ECG waveform detecting apparatuses 1a to 1d may configure an ECG waveform detecting apparatus 1e.

Figure 39:
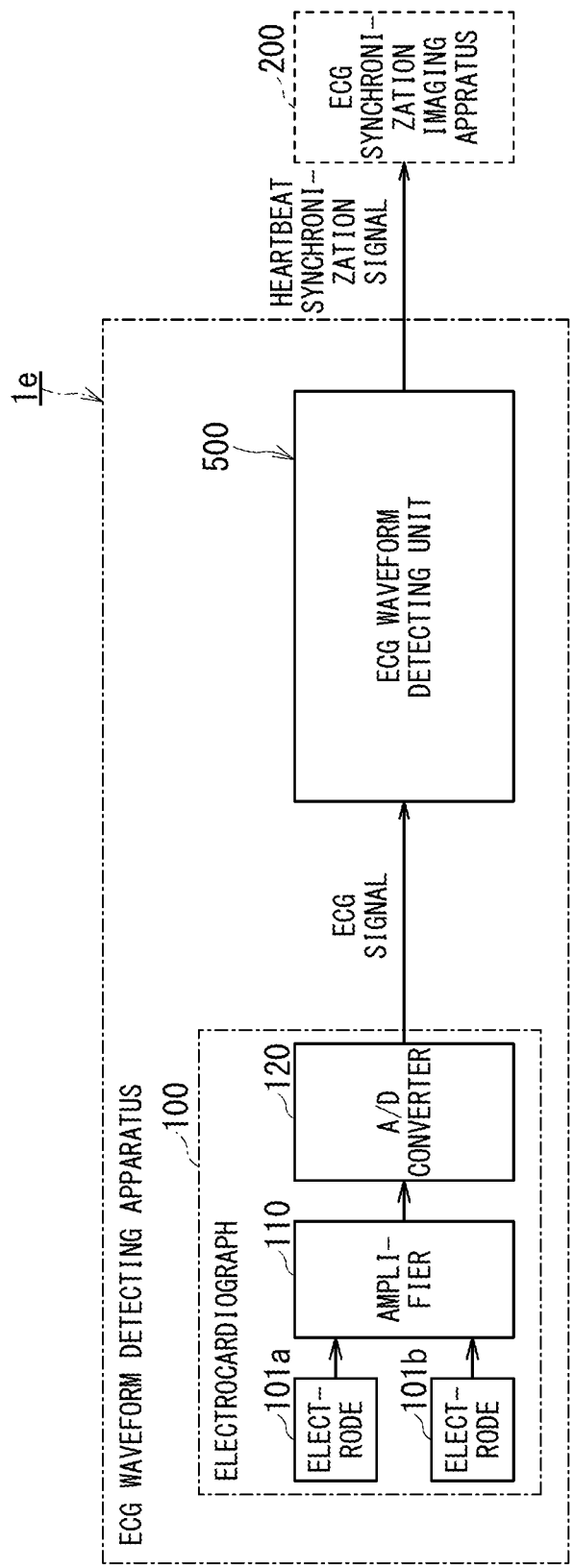
FIG. 39 is a block diagram showing an example in which an ECG waveform detecting apparatus includes an electrocardiograph and an ECG waveform detecting unit.
Figure 40:
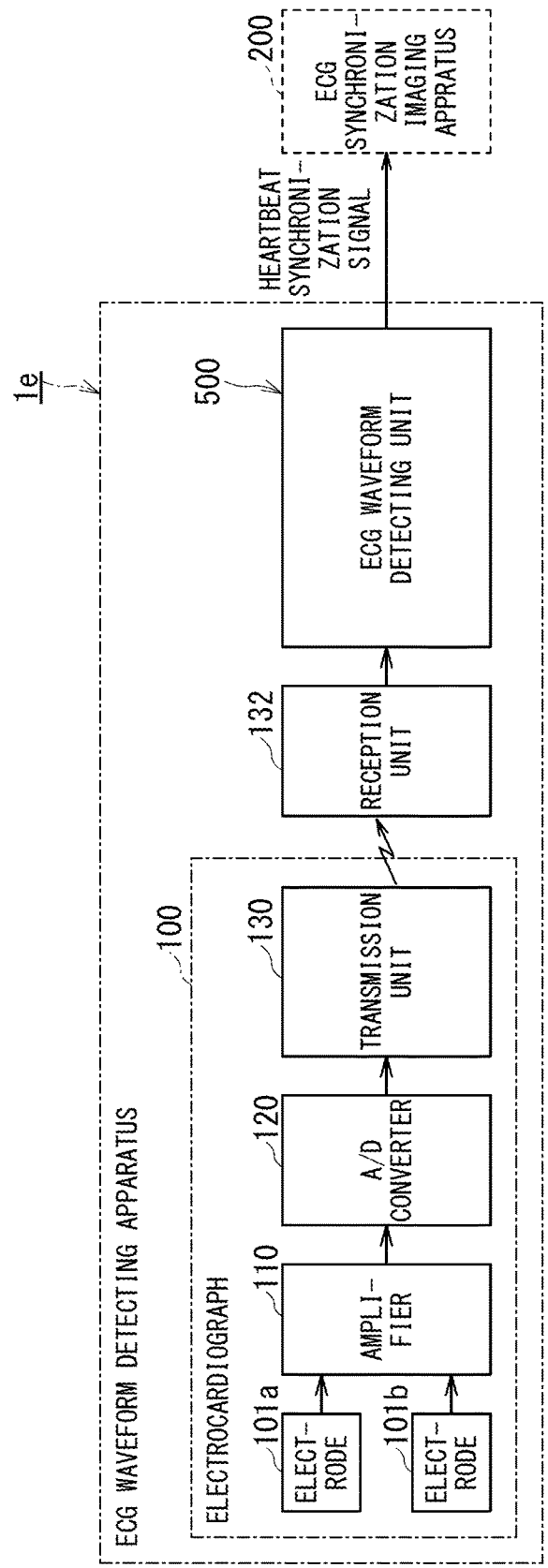
FIG. 40 is a block diagram showing another example in which the ECG waveform detecting apparatus includes the electrocardiograph and the ECG waveform detecting unit.
Figure 41:
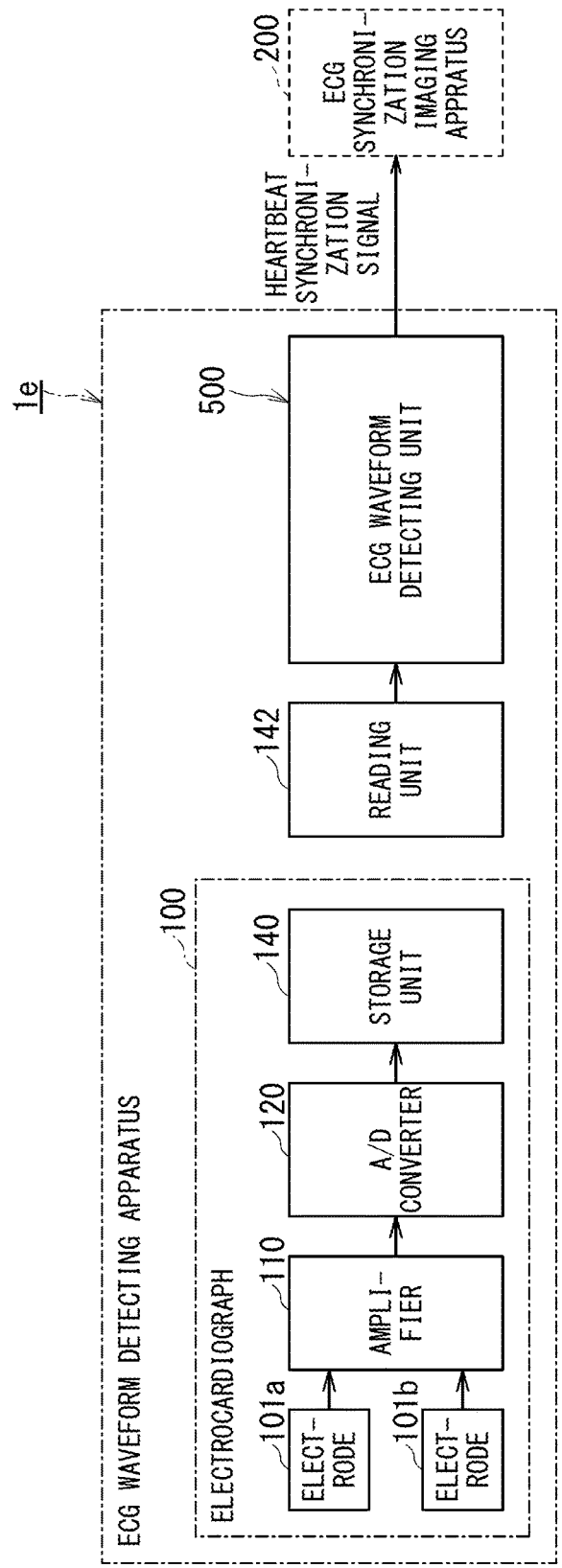
FIG. 41 is a block diagram showing still another example in which the ECG waveform detecting apparatus includes the electrocardiograph and the ECG waveform detecting unit.

FIG. 39 to FIG. 41 are block diagrams showing examples in which the ECG waveform detecting apparatus 1e includes the electrocardiograph 100 and the ECG waveform detecting unit 500.

In the ECG waveform detecting apparatus 1e shown in FIG. 39, ECG signals received from the A/D converter 120 are inputted to the ECG waveform detecting unit 500 by wire.

The ECG waveform detecting apparatus 1e shown in FIG. 40 further includes a transmission unit 13 and a reception unit 132. The transmission unit 130 and the reception unit 132 are capable of mutual wireless communication. The reception unit 132 receives ECG signals wirelessly transmitted from the transmission unit 130, and inputs the received ECG signals to the ECG waveform detecting unit 500. According to this configuration, hard-wiring extended to the outside can be omitted from the electrocardiograph 100 loaded on a patient lying inside the bore of the ECG synchronization imaging apparatus 200.

The ECG waveform detecting apparatus 1e shown in FIG. 41 further includes a storage unit 140 and a reading unit 142. The storage unit 140 stores ECG signals in a portable recording medium such as a CD, a DVD, a USB memory, The reading unit 142 reads in data of ECG signals stored in the recording medium. The reading unit 142 transmits the read ECG signals to the ECG waveform detecting unit 500.

Incidentally, the orders of the above-mentioned various types of processes (for example, FIG. 5, FIG. 7, FIG. 11, FIG. 16, and FIG. 28) are not necessarily limited to the illustrated orders. Processes which can be performed in parallel may be performed in parallel, and a processing procedure which does not depend on its order may be performed by changing its order.

As explained above, according to each of the above embodiments and their modifications, a specific waveform in ECG signals can be detected while achieving both high detection reliability and short delay time.

Incidentally, the processing circuitry 302 in the above embodiments and their modifications is an example of the processing circuitry described in the claims. In addition, the input interface 10 in the above embodiments and their modifications is an example of the input circuit described in the claims.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

Hereinafter, examples of various aspects of ECG waveform detecting apparatuses, ECG waveform detecting programs and ECG synchronization imaging apparatuses according to each of the above-mentioned embodiments and their modifications will be explained.

<Aspect A1>

An ECG waveform detecting apparatus including:

a first detection unit configured to detect a specific waveform included in an acquired ECG signal;

an update unit configured to update a detection parameter for detecting the specific waveform, based on a part of the specific waveform detected by the first detection unit;

a second detection unit configured to detect the specific waveform from the ECG signal by using the updated detection parameter; and a generation unit configured to generate a synchronization signal based on information related to detection of the specific waveform performed by the second detection unit.

<Aspect A2>

The ECG waveform detecting apparatus according to the Aspect A1, wherein the specific waveform is one of a P-wave, an R-wave, a QRS complex wave, and a T-wave.

<Aspect A3>

The ECG waveform detecting apparatus according to the Aspect A1, wherein the first detection unit is configured to detect the specific waveform based on the ECG signal included in a first detection period; and the second detection unit is configured to detect the specific waveform based on the ECG signal included in a second detection period which is shorter than the first detection period.

<Aspect A4>

The ECG waveform detecting apparatus according to the Aspect A3, wherein the specific waveform is an R-wave;

the first detection period is composed of a span of the R-wave, a span which starts earlier than the R-wave by a predetermined time and ends immediately before the R-wave, and a span which starts immediately after the R-wave and lasts for a predetermined time; and the second detection period is a period which starts earlier than a peak of the R-wave by a predetermined time and lasts to the peak.

<Aspect A5>

The ECG waveform detecting apparatus according to the Aspect A3, wherein the second detection unit is configured to hold a waveform of the ECG signal corresponding to the second detection period as a template, and to detect the specific waveform by matching the template with a waveform of the ECG signal to be inputted.

<Aspect A6>

The ECG waveform detecting apparatus according to the Aspect A1, wherein the specific waveform is an R-wave; and the second detection unit is configured to hold a waveform of the ECG signal corresponding to a period, which starts earlier than a peak of the R-wave by a predetermined time and lasts to the peak, as a template, and to detect the specific waveform by matching the template with a waveform of the ECG signal to be inputted.

<Aspect A7>

The ECG waveform detecting apparatus according to the Aspect A5 or the Aspect A6, wherein the detection parameter is a shape of the template; and the update unit is configured to update the shape of the template held in the second detection unit by using the specific waveform detected by the first detection unit.

<Aspect A8>

The ECG waveform detecting apparatus according to one of the Aspects A1 to A7, wherein an execution interval of processing of detecting the specific waveform by the second detection unit is shorter than an execution interval of processing of detecting the specific waveform by the first detection unit.

<Aspect A9>

The ECG waveform detecting apparatus according to one of the Aspects A1 to A8, wherein the update unit is configured to determine whether a detection condition in the first detection unit is abnormal or not, and to stop update of the detection parameter when the detection condition is abnormal.

<Aspect A10>

The ECG waveform detecting apparatus according to the Aspect A9, wherein the update unit is configured to determine the detection condition to be abnormal when number of detection by the first detection unit within a predetermined abnormality determination period is larger than a predetermined reference number.

<Aspect A11>

The ECG waveform detecting apparatus according to one of the Aspects A1 to A8, wherein the update unit is configured to receive information on operation state of an ECG synchronization imaging apparatus which is an output destination of the synchronization signal, and to determine whether the detection parameter can be updated or not, based on the information on operation state.

<Aspect A12>

An imaging apparatus including:

a first detection unit configured to detect a specific waveform included in an acquired ECG signal;

an update unit configured to update a detection parameter for detecting the specific waveform, based on a part of the specific waveform detected by the first detection unit;

a second detection unit configured to detect the specific waveform from the ECG signal by using the updated detection parameter;

a generation unit configured to generate a synchronization signal based on information related to detection of the specific waveform performed by the second detection unit;

a data acquisition unit configured to acquire imaging data from an object in synchronization with the synchronization signal; and an image generation unit configured to generate an image of the object based on the imaging data.

<Aspect A13>

The imaging apparatus according to the Aspect A12 configured as an MRI apparatus.

<Aspect A14>

A computer-readable storage medium storing an ECG waveform detecting program for causing a computer to execute a process, including steps of:

detecting a specific waveform included in an acquired ECG signal, as a first detection step;

updating a detection parameter for detecting the specific waveform based on a part of a waveform of the specific waveform detected in the first detection step, as an update step;

detecting the specific waveform from the ECG signal by using the updated detection parameter, as a second detection step; and generating a synchronization signal based on information related to detection of the specific waveform in the second detection, as a generation step.

<Aspect B1>

An ECG waveform detecting apparatus including:

an enhancing unit configured to generate a second ECG signal by enhancing a high-frequency band of at least one first ECG signal acquired from an object;

a calculation unit configured to calculate an evaluation value by matching the second ECG signal with a template corresponding to a specific target waveform; and a detection unit configured to detect the specific target waveform based on the evaluation value.

<Aspect B2>

The ECG waveform detecting apparatus according to the Aspect B1, further including a generation unit configured to generate the template based on the second ECG signal.

<Aspect B3>

The ECG waveform detecting apparatus according to the Aspect B2, further including a determination unit configured to determine whether the template should be generated or not, wherein the generation unit is configured to generate the template based on a determination result of the determination unit.

<Aspect B4>

The ECG waveform detecting apparatus according to the Aspect B3, wherein the determination unit is configured to acquire information on operation state of an MRI apparatus, to determine that the template should not be generated in a period during which the MRI apparatus is acquiring magnetic resonance signals from the object, and to determine that the template should be generated in a period during which the MRI apparatus is not acquiring the magnetic resonance signals.

<Aspect B5>

The ECG waveform detecting apparatus according to the Aspect B2, wherein the generation unit is configured to extract a signal of a predetermined period from the first ECG signal based on a pulse wave signal of the object, and to generate the template based on the signal of a predetermined period.

<Aspect B6>

The ECG waveform detecting apparatus according to one of the Aspects B1 to B5, wherein the calculation unit is configured to calculate the evaluation value as cross-correlation between the second ECG signal and the template.

<Aspect B7>

The ECG waveform detecting apparatus according to one of the Aspects B1 to B6, wherein the calculation unit is configured to calculate the evaluation value based on at least one of (a) a total sum of difference square values between the second ECG signal and the template, (b) a total sum of difference absolute values between the second ECG signal and the template, (c) L-p norms of difference values between the second ECG signal and the template where p>0, and (d) a total sum of function values obtained by applying a function, which returns a value smaller than a square of a difference between the second ECG signal and the template in a case of the difference larger than a predetermined value, to the difference.

<Aspect B8>

The ECG waveform detecting apparatus according to one of the Aspects B1 to B7, further including a integrating unit, wherein the enhancing unit is configured to generate a plurality of second ECG signals by enhancing respective high-frequency bands of a plurality of first ECG signals simultaneously acquired from the object as high-frequency enhancement processing;

the calculation unit is configured to calculate a plurality of evaluation values respectively corresponding to the plurality of second ECG signals;

the integrating unit is configured to calculate a synthetic evaluation value by adding the plurality of evaluation values or calculating a weighted sum of the plurality of evaluation values; and the detection unit is configured to detect the target waveform base on the synthetic evaluation value.

<Aspect B9>

The ECG waveform detecting apparatus according to the Aspect B8, wherein the plurality of first ECG signals are signals of generating a vectorcardiogram.

<Aspect B10>

The ECG waveform detecting apparatus according to the Aspect B8, further including a dimension reduction unit configured to perform dimension reduction processing of reducing number of the first ECG signals to number smaller than N before the high-frequency enhancement processing, when the number of the first ECG signals is originally N and the first ECG signals are N-dimensional time-series signals, wherein the dimension reduction unit is configured to calculate principal component vectors by performing principal component analysis on the N-dimensional time-series signals, and to reduce the number of the first ECG signals to the number smaller than N by projecting the N-dimensional time-series signals onto a partial space generated from the principal component vectors each of which has a contribution rate larger than a predetermined value.

<Aspect B11>

The ECG waveform detecting apparatus according to the Aspect B1, further including a storage unit configured to store the template, wherein the generation unit is configured to generate the template before acquisition of the first ECG signal; and the storage unit is configured to store the template before the acquisition of the first ECG signal.

<Aspect B12>

An imaging apparatus including:

an enhancing unit configured to generate a second ECG signal by enhancing a high-frequency band of at least one first ECG signal acquired from an object;

a calculation unit configured to calculate an evaluation value by matching the second ECG signal with a template corresponding to a specific target waveform;

a detection unit configured to detect the specific target waveform based on the evaluation value, and to generate a synchronization signal based on the specific target waveform;

a data acquisition unit configured to acquire imaging data from the object in synchronization with the synchronization signal; and an image generation unit configured to generate an image of the object based on the imaging data.

<Aspect B13>

The imaging apparatus according to the Aspect B12 configured as an MRI apparatus.

<Aspect B14>

An ECG waveform detecting method including steps of:
generating a second ECG signal by enhancing a high-frequency band of at least one first ECG signal acquired form an object;
calculating an evaluation value by matching the second ECG signal with a template corresponding to a specific target waveform; and
detecting the specific target waveform based on the evaluation value.

<Aspect B15>

A computer-readable storage medium storing an ECG waveform detecting program for causing a computer to execute a process, including steps of:
generating a second ECG signal by enhancing a high-frequency band of at least one first ECG signal acquired form an object;
calculating an evaluation value by matching the second ECG signal with a template corresponding to a specific target waveform; and
detecting the specific target waveform based on the evaluation value.

<Aspect C1>

An ECG waveform detecting apparatus including:
a first integration unit configured to calculate a first integrated value of an acquired ECG signal during a first period;
a second integration unit configured to calculate a second integrated value of the ECG signal during a second period;
at least one detection unit configured to detect a specific target waveform included in the ECG signal by using the first integrated value and the second integrated value.

<Aspect C2>

The ECG waveform detecting apparatus according to the Aspect C1,
wherein the detection unit is configured to detect the specific target waveform by matching a predetermined reference value with a difference between the first integrated value and the second integrated value.

<Aspect C3>

The ECG waveform detecting apparatus according to the Aspect C1 or the Aspect C2, further including an accumulation unit configured to calculate an accumulated value by time-sequentially accumulating ECG signals which are time-sequentially acquired,
wherein the first integration unit is configured to calculate a difference between the accumulated value at start time of the first period and the accumulated value at ending time of the first period, as the first integrated value; and
the second integration unit is configured to calculate a difference between the accumulated value at start time of the second period and the accumulated value at ending time of the second period, as the second integrated value.

<Aspect C4>

The ECG waveform detecting apparatus according to the Aspect C1 or the Aspect C2, further including a holding unit,
wherein the ECG signal is time-series sample values;
the holding unit is configured to hold the time-series sample values;
the first integration unit is configured to subtract a sample value at start time of the first period held in the holding unit from the first integrated value and then update the first integrated value by adding a newly acquired sample value for the first period to the first integrated value subjected to subtraction, when the first integration unit acquires a new sample value for the first period; and
the second integration unit is configured to subtract a sample value at start time of the second period held in the holding unit from the second integrated value and then update the second integrated value by adding a newly acquired sample value for the second period to the second integrated value subjected to subtraction, when the second integration unit acquires a new sample value for the second period.

<Aspect C5>

The ECG waveform detecting apparatus according to one of the Aspects C1 to C4, further including:
a plurality of detection units respectively configured to detect a specific target waveform by using the first integrated value and the second integrated value; and
a synthetic detection unit configured to calculate integrated detection information by using detection information respectively outputted from the plurality of detection units and weighting values respectively set for the plurality of detection units;
wherein at least one of the first period and the second period for the ECG signal is/are different for each of the plurality of detection units.

<Aspect C6>

An imaging apparatus including:
a first integration unit configured to calculate a first integrated value of an acquired ECG signal during a first period;
a second integration unit configured to calculate a second integrated value of the ECG signal during a second period;
a detection unit configured to detect a specific target waveform included in the ECG signal by using the first integrated value and the second integrated value, and to generate a synchronization signal based on the detected specific target waveform;
a data acquisition unit configured to acquire imaging data of an object in synchronization with the synchronization signal; and
an image generation unit configured to generate an image of the object based on the imaging data.

<Aspect C7>

The imaging apparatus according to the Aspect C6 configured as an MRI apparatus.

<Aspect C8>

An ECG waveform detecting method including steps of:
calculating a first integrated value of an acquired ECG signal during a first period;
calculating a second integrated value of the ECG signal during a second period;
detecting a specific target waveform included in the ECG signal by using the first integrated value and the second integrated value.

<Aspect C9>

A computer-readable storage medium storing an ECG waveform detecting program for causing a computer to execute a process, including steps of:
calculating a first integrated value of an acquired ECG signal during a first period;
calculating a second integrated value of the ECG signal during a second period;
detecting a specific target waveform included in the ECG signal by using the first integrated value and the second integrated value.

<Aspect D1>

An ECG waveform detecting apparatus including:

an input circuit configured to receive an ECG signal; and processing circuitry configured to (a) perform first detection of a specific waveform included in the ECG signal, (b) perform update processing of a detection parameter for detecting the specific waveform, based on a part of the specific waveform or result of the first detection, (c) perform second detection of the specific waveform from the ECG signal by using the detection parameter after the update processing, and (d) generate a synchronization signal based on information on the second detection.

What is claimed is:

1. An ECG waveform detecting apparatus comprising:
an input circuit configured to receive an ECG signal; and
processing circuitry configured to
(a) perform first detection of a specific waveform included in the ECG signal,
(b) perform update processing of a detection parameter for detecting the specific waveform, based on a part of the specific waveform or result of the first detection,
(c) perform second detection of the specific waveform from the ECG signal by using the detection parameter after the update processing, and
(d) generate a synchronization signal based on information on the second detection,
wherein the processing circuitry is configured to perform the first detection based on the ECG signal included in a first detection period and perform the second detection based on the ECG signal included in a second detection period which is a period shorter than the first detection period.

2. The apparatus according to claim 1,
wherein the specific waveform is an R-wave;
the first detection period is composed of a span of the R-wave, a span which starts earlier than the R-wave by a predetermined time and ends immediately before the R-wave, and a span which starts immediately after the R-wave and lasts for a predetermined time; and
the second detection period is a period which starts earlier than a peak of the R-wave by a predetermined time and lasts to the peak.

3. An imaging apparatus comprising the ECG waveform detecting apparatus according to claim 2.

4. The apparatus according to claim 1,
wherein the processing circuitry is configured to
(a) generate a high-frequency enhanced ECG signal by enhancing a high-frequency band of the ECG signal,
(b) perform the second detection by holding a waveform corresponding to the high-frequency enhanced ECG signal as a high-frequency enhanced template and then matching the high-frequency enhanced template with a waveform of the high-frequency enhanced ECG signal, and
(c) perform the update processing by extracting the high-frequency enhanced ECG signal corresponding to the specific waveform and then updating the high-frequency enhanced template as the detection parameter, based on result of the first detection.

5. An imaging apparatus comprising the ECG waveform detecting apparatus according to claim 4.

6. The apparatus according to claim 1,
wherein the processing circuitry is configured to perform the first detection and the second detection so that at least one of the first detection and the second detection includes processing of (a) calculating a first integrated value of the ECG signal during a first period, (b) calculating a second integrated value of the ECG signal during a second period, and (c) detecting the specific waveform by using the first integrated value and the second integrated value.

7. An imaging apparatus comprising the ECG waveform detecting apparatus according to claim 6.

8. The ECG waveform detecting apparatus according to claim 1,
wherein the detection parameter is a shape of a template; and
the processing circuitry is configured to perform the update processing by updating the shape of the template by using the specific waveform detected in the first detection.

9. An imaging apparatus comprising the ECG waveform detecting apparatus according to claim 8.

10. The ECG waveform detecting apparatus according to claim 1,
wherein the processing circuitry is configured to perform the update processing by receiving information on operation state of an ECG synchronization imaging apparatus which is an output destination of, the synchronization signal and determining whether the detection parameter can be updated or not based on the information on operation state.

11. An imaging apparatus comprising the ECG waveform detecting apparatus according to claim 10.

12. An imaging apparatus comprising the ECG waveform detecting apparatus according to claim 1.

13. An ECG waveform detecting method comprising:
performing first detection of a specific waveform included in an ECG signal,
performing update processing of a detection parameter for detecting the specific waveform, based on a part of the specific waveform or result of the first detection,
performing second detection of the specific waveform from the ECG signal by using the detection parameter after the update processing, and
generating synchronization signal based on information on the second detection,
wherein the first detection is performed based on the ECG signal included in a first detection period and the second detection is performed based on the ECG signal included in a second detection period which is a period shorter than the first detection period.

14. The method according to claim 13,
wherein the specific waveform is an R-wave;
the first detection period is composed of a span of the R-wave, a span which starts earlier than the R-wave by a predetermined time and ends immediately before the R-wave, and a span which starts immediately after the R-wave and lasts for a predetermined time; and
the second detection period is a period which starts earlier than a peak of the R-wave by a predetermined time and lasts to the peak.

15. The method according to claim 13, further comprising:
generating a high-frequency enhanced ECG signal by enhancing a high-frequency band of the ECG signal,
performing the second detection by holding a waveform corresponding to the high-frequency enhanced ECG signal as a high-frequency enhanced template and then matching the high-frequency enhanced template with a waveform of the high-frequency enhanced ECG signal, and performing the update processing by extracting the high-frequency enhanced ECG signal corresponding to the specific waveform and then updating the high-frequency enhanced template as the detection parameter, based on result of the first detection.

16. The method according to claim 13, wherein the processing circuitry is configured to perform the first detection and the second detection so that at least one of the first detection and the second detection includes processing of (a) calculating a first integrated value of the ECG signal during a first period, (b) calculating a second integrated value of the ECG signal during a second period, and (c) detecting the specific waveform by using the first integrated value and the second integrated value.

17. The method according to claim 13, wherein the detection parameter is a shape of a template; and the shape of the template is updated by using the specific waveform detected in the first detection.

18. The method according to claim 13, further comprising:

receiving information on operation state of an ECG synchronization imaging apparatus which is an output destination of the synchronization signal; and determining whether the detection parameter can be updated or not based on the information on the operation state.

* * * * *